(12) United States Patent
Dosoretz et al.

(10) Patent No.: US 11,591,219 B2
(45) Date of Patent: Feb. 28, 2023

(54) CARBON NANOTUBE LAMINATES

(71) Applicant: TECHNION RESEARCH & DEVELOPMENT FOUNDATION LIMITED, Haifa (IL)

(72) Inventors: Carlos George Dosoretz, Carmiel (IL); Avner Ronen, Amber, PA (US); Chidambaram Thamaraiselvan, Haifa (IL); Sofia Lerman Roytblat, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/902,119

(22) Filed: Feb. 22, 2018

(65) Prior Publication Data

US 2018/0237301 A1  Aug. 23, 2018

Related U.S. Application Data

(60) Provisional application No. 62/462,432, filed on Feb. 23, 2017.

(51) Int. Cl.
*C01B 32/158* (2017.01)
*B01D 69/02* (2006.01)
(Continued)

(52) U.S. Cl.
CPC ........ *C01B 32/158* (2017.08); *B01D 39/2055* (2013.01); *B01D 65/08* (2013.01);
(Continued)

(58) Field of Classification Search
CPC ............. C01B 32/158; C01B 2202/22; C01B 2202/24; G01N 33/5302; G01N 33/6857;
(Continued)

(56) References Cited

U.S. PATENT DOCUMENTS

| 7,211,320 B1 | 5/2007 | Cooper et al. |
| 2007/0084797 A1 | 4/2007 | Cooper et al. |

(Continued)

FOREIGN PATENT DOCUMENTS

| WO | 2005007926 A2 | 1/2005 | |
| WO | WO-2009055831 A1 * | 4/2009 | ............... C09D 7/67 |

(Continued)

OTHER PUBLICATIONS

Avner Ronen et al: "Microbial Attachment Inhibition through Low-Voltage Electrochemical Reactions on Electrically Conducting Membranes", Environ. Sci. Technol., 2015, vol. 49, No. 21, pp. 12741-12750.

(Continued)

*Primary Examiner* — Latosha Hines
(74) *Attorney, Agent, or Firm* — The Roy Gross Law Firm, LLC; Roy Gross

(57) ABSTRACT

Compositions made of laminate comprised of porous carbon nanotube (CNT) are disclosed. Uses of the Compositions, particularly for reducing a formation of a load of a microorganism or of a biofilm, are also disclosed.

11 Claims, 56 Drawing Sheets

(9 of 56 Drawing Sheet(s) Filed in Color)

(51) Int. Cl.
| | |
|---|---|
| C02F 1/44 | (2006.01) |
| H01L 51/44 | (2006.01) |
| B01D 39/20 | (2006.01) |
| C02F 3/12 | (2006.01) |
| C02F 1/46 | (2006.01) |
| B01D 67/00 | (2006.01) |
| B01D 71/02 | (2006.01) |
| B01D 65/08 | (2006.01) |
| B82Y 40/00 | (2011.01) |
| H01L 51/00 | (2006.01) |
| B82Y 5/00 | (2011.01) |
| C02F 101/16 | (2006.01) |
| C02F 101/38 | (2006.01) |
| C02F 101/32 | (2006.01) |
| C02F 101/34 | (2006.01) |
| B82Y 30/00 | (2011.01) |
| C02F 101/30 | (2006.01) |
| C02F 101/36 | (2006.01) |

(52) U.S. Cl.
CPC ..... B01D 67/0041 (2013.01); B01D 67/0072 (2013.01); B01D 69/02 (2013.01); B01D 71/021 (2013.01); C02F 1/44 (2013.01); C02F 1/444 (2013.01); C02F 1/4602 (2013.01); C02F 3/1268 (2013.01); H01L 51/444 (2013.01); B01D 2239/1216 (2013.01); B01D 2321/22 (2013.01); B01D 2323/39 (2013.01); B01D 2325/02 (2013.01); B01D 2325/04 (2013.01); B01D 2325/20 (2013.01); B01D 2325/22 (2013.01); B01D 2325/26 (2013.01); B01D 2325/28 (2013.01); B01D 2325/30 (2013.01); B82Y 5/00 (2013.01); B82Y 30/00 (2013.01); B82Y 40/00 (2013.01); C01B 2202/22 (2013.01); C01B 2202/24 (2013.01); C01P 2004/13 (2013.01); C01P 2006/10 (2013.01); C01P 2006/37 (2013.01); C01P 2006/40 (2013.01); C02F 2101/16 (2013.01); C02F 2101/306 (2013.01); C02F 2101/308 (2013.01); C02F 2101/32 (2013.01); C02F 2101/327 (2013.01); C02F 2101/345 (2013.01); C02F 2101/36 (2013.01); C02F 2101/38 (2013.01); C02F 2101/40 (2013.01); C02F 2303/20 (2013.01); C02F 2305/08 (2013.01); H01L 51/0048 (2013.01); Y02E 10/549 (2013.01)

(58) Field of Classification Search
CPC ............ G01N 33/6893; B01D 39/2055; B01D 65/08; B01D 67/0041; B01D 67/0072; B01D 69/02; B01D 71/021; B01D 2239/1216; B01D 2321/22; B01D 2323/39; B01D 2325/02; B01D 2325/04; B01D 2325/20; B01D 2325/22; B01D 2325/26; B01D 2325/28; B01D 2325/30; C02F 1/44; C02F 1/444; C02F 1/4602; C02F 3/1268; C02F 2101/16; C02F 2101/306; C02F 2101/308; C02F 2101/32; C02F 2101/327; C02F 2101/345; C02F 2101/36; C02F 2101/38; C02F 2101/40; C02F 2303/20; C02F 2305/08; H01L 51/444; H01L 51/0048; B82Y 5/00; B82Y 30/00; B82Y 40/00; C01P 2004/13; C01P 2006/10; C01P 2006/37; C01P 2006/40
See application file for complete search history.

(56) References Cited

U.S. PATENT DOCUMENTS

| | | | | |
|---|---|---|---|---|
| 2008/0044651 | A1* | 2/2008 | Douglas | C08J 7/0427 428/339 |
| 2008/0170982 | A1* | 7/2008 | Zhang | B82Y 10/00 423/447.3 |
| 2011/0253630 | A1* | 10/2011 | Bakajin | B82Y 30/00 427/244 |
| 2012/0211367 | A1* | 8/2012 | Vecitis | B82Y 30/00 204/554 |
| 2013/0157171 | A1* | 6/2013 | Kurokawa | H01M 4/8605 429/484 |
| 2013/0309473 | A1* | 11/2013 | Sundaram | B82Y 40/00 428/220 |

FOREIGN PATENT DOCUMENTS

| | | | | |
|---|---|---|---|---|
| WO | WO-2010072233 | A1 * | 7/2010 | ............ H01M 8/103 |
| WO | 2012059716 | A1 | 5/2012 | |

OTHER PUBLICATIONS

Charles-François de Lannoy et al: "Aquatic Biofouling Prevention by Electrically Charged Nanocomposite Polymer Thin Film Membranes"; Environmental Science & Technology, 2013, vol. 47, pp. 2760-2768.

Chad D. Vecitis et al. "Electrochemical Carbon Nanotube Filter for Adsorption, Desorption, and Oxidation of Aqueous Dyes and Anions." Journal of Physical Chemistry. vol. 115, 3621-3629 (2011).

* cited by examiner

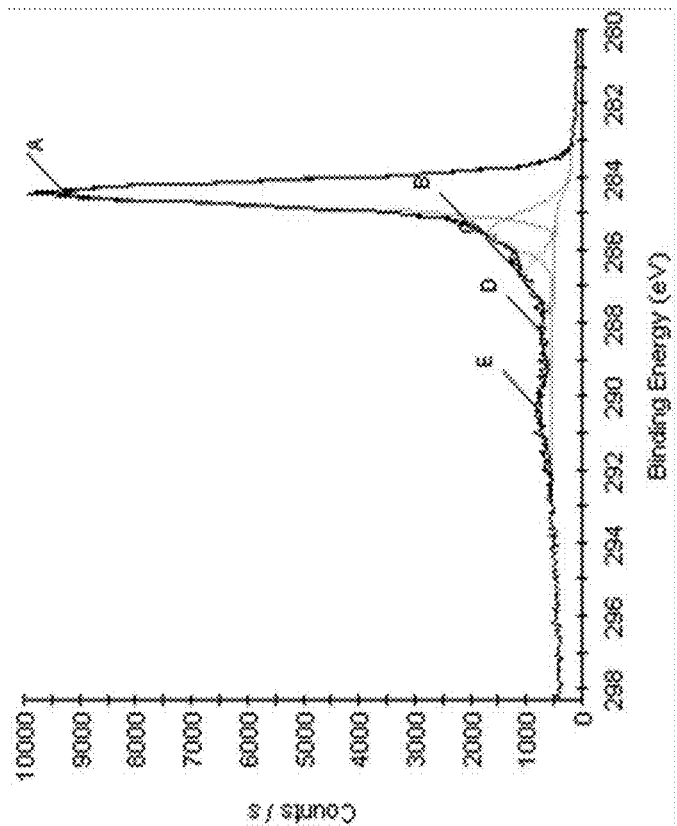
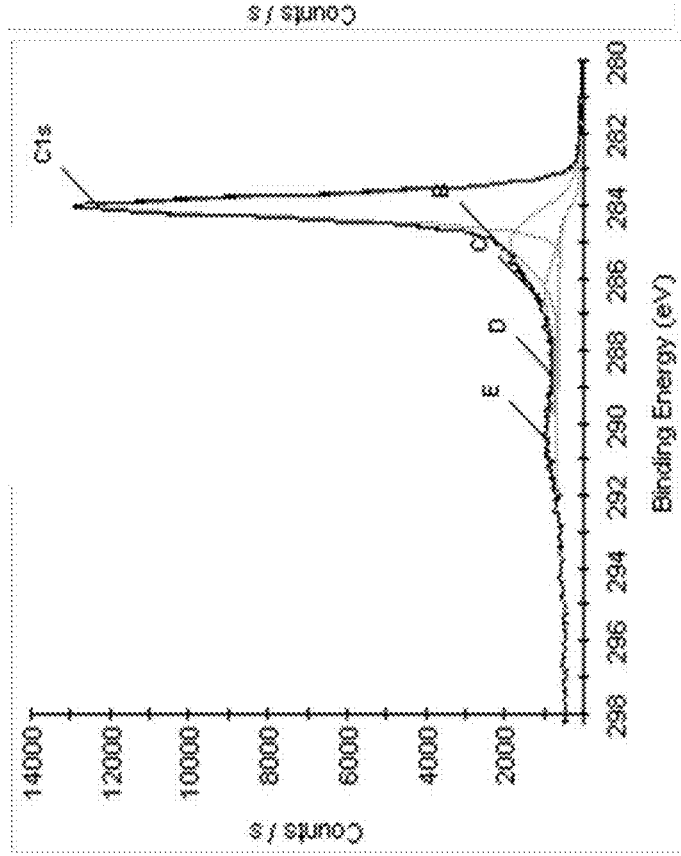
Figure 7A
Figure 7B

| Electric potential | Electrode/ Membrane | Bacteria/ Conditions | Detachment/ Prevention of attachment | Inactivation | Duration | Source# |
|---|---|---|---|---|---|---|
| Cathodic(100μA)& Block (100μA) | Stainless steel | *Staphylococcus epidermidis* | 78±5% at cathodic 31±6% at Block | 97% at DC 98% at Block | 11 h | Van der Borden et al., 2004, J. Biomed. Mater. Res. B. Appl. Biomater. 68 |
| AC, 1.5V | Polymer nanocomposite | *Pseudomonas aeruginosa* | (No quantitative data) | (No quantitative data) | 2-3 days | De Lannoy et al., 2013. Environ. Sci. Technol. 47, 2760 |
| Anodic, 1.5V Cathodic, 1.5V | Polymer nanocomposite | *E. coli* | (No quantitative data) | 32±21% at Cathodic 67±3.6% at Anodic | 30 min | Ronen et al., 2015a, Environ. Sci. Technol. 49, 12741 |
| Positive 0.2V Negative -0.2 and -0.5 V | Gold electrode | *Pseudomonas fluorescence* | Negative is more effective (No quantitative data) | (No quantitative data) | 15 min | Busalmen and De Sánchez, 2001, Appl. Environ. Microbiol. 67, 3188 |
| Anodic Cathodic AC, 15 μA/cm | ITO-coated glass | *Pseudomonas aeruginosa* | 70% at Anodic, 80% at Cathodic. No quantitative data for AC | Anodic (85%)>AC>Cathodic | 40 min | Hong et al., 2008, Biotechnol. Bioeng. 100, 379 |

Figure 17

| | | | | |
|---|---|---|---|---|
| Negative, 15 μA/cm² Positive-15 μA/cm² AC-15 μA/cm² | ITO-coated glass | *Pseudomonas aeruginosa* | 81% at Negative 20% at Positive >81% at AC | ~58% at AC | 90 min | Shim et al., 2011, Biofouling 27 |
| Anodic, 1V Cathodic, 1V AC | Feed spacer-Ti Mesh | *Pseudomonas aeruginosa* | 7.4×10⁸ CFU/cm² at control 5.1×10⁸ CFU/cm² at positive, 4.6×10⁸ at negative, 3.5×10⁸ at AC | (No quantitative data) | 24h | Baek et al., 2014, Environ. Sci. Technol. Lett. 1, 179 |
| AC, 100 μA | Stainless steel | *Staphylococcus epidermidis* | 76% at block | (No quantitative data) | 90 min | van der Borden et al., 2005, Biomater. 26, 6731 |
| AC & DC 600-6000 mV-no filtration | CNT self-support membrane | *P. Putida S12* | >99% at AC capacitive >98.7% at cathodic <20% at anodic | 80.0±4.8% at 4500mV AC, capacitive | 72 h | Present disclosure* |
| At 1500 mV-no filtration | | | >99.5% at 1500mV AC >99% at 1500mV DC | 27.98 at 3000mV DC, cathodic 27.84 % at 900mV, anodic | | |
| At 1500 mV-filtration | | | 41.46% at AC | 92% at 1500mV AC 25% at 1500mV DC | | |
| At 4500mV-filtration | | | 39.17% at cathodic 4.17% at anodic 72.46% at AC 4500 mV | 32.94% at AC 6.35% at cathodic 20.73% at anodic 80.32% at AC 4500mV | | |

Figure 17 continued

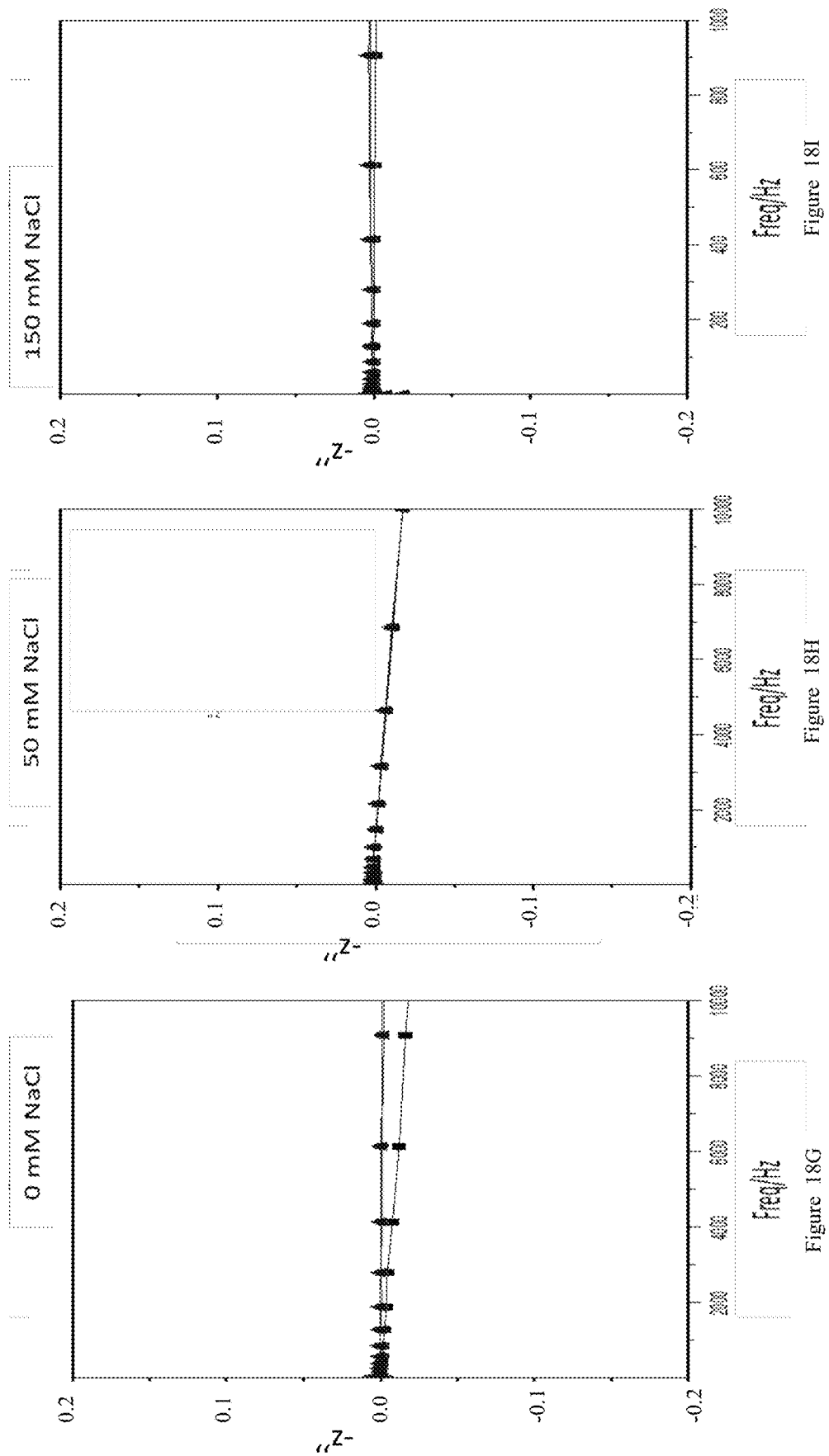

CARBON NANOTUBE LAMINATES

CROSS-REFERENCE TO RELATED APPLICATIONS

This application claims the benefit of priority from U.S. Provisional Patent Application No. 62/462,432, filed on Feb. 23, 2017. The content of the above document is incorporated by reference in its entirety as if fully set forth herein.

FIELD OF THE INVENTION

The present invention, in some embodiments thereof, relates to carbon nanotube laminates and use thereof e.g., for filtration membranes.

BACKGROUND OF THE INVENTION

Water purification is the process of removing undesirable chemicals, biological contaminants such as bacteria, suspended solids and gases from contaminated water. Most water is purified for human consumption (e.g., drinking water). In general, the methods used include physical processes such as filtration, sedimentation, and distillation, biological processes such as slow sand filters or biologically active carbon, chemical processes such as flocculation and chlorination and the use of electromagnetic radiation such as ultraviolet light.

Pressure driven-membrane separation processes are a key technology for water purification and production of new water sources. However, membranes are susceptible to fouling. Biofouling is the most complex and difficult to solve form of fouling and hinders the utilization of membrane technology in many applications. Biofouling is defined operationally and refers to the amount of biofilm development which interferes with technical or economic requirements.

Antimicrobial modification of surfaces for preventing the growth of detrimental microorganisms is a highly desired objective. Microbial infestation of surfaces is one of the leading causes of infections. This often leads to life threatening complications.

Bacterial attachment to surfaces leading to the formation of communities of bacterial cells is a major problem in many diverse settings. This sessile community of microorganisms, also termed "biofilm", is attached to an interface, or to each other, and embedded in an exopolymeric matrix.

Electrical current has been described to influence bacterial adhesion to conductive solid surfaces in many fields, including medical and industrial applications. Although high electrical potentials (in the range of kV/cm) is known to inactivate bacteria and yeasts and has been described for surface sanitation, there is a growing interest in the last decade in applying low electrical potentials (in the range of mV/cm) to control bacterial attachment and biofilm formation. Low electrical potential has been studied to influence bacterial adhesion to conductive solid surfaces, such as surgical stainless steel and gold, platinum and indium-tin oxide electrodes, especially for detachment of bacteria cells. Despite many studies on bacteria detachment on conductive surfaces, there is no report focused on the prevention of the initial attachment.

Carbon nanotubes (CNTs) have been proposed for a number of potential applications, including electronic circuit applications such as field effect transistors, capacitors and/or ultra-capacitors, memory arrays, traces, and switches. Numerous other applications have been proposed as well, such as structural materials, heaters and heat transfer conduits, and numerous others.

U.S. Pat. No. 7,211,320 discloses a nanostructured material comprising defective carbon nanotubes. Also disclosed therein is a method of purifying fluids, such as liquids, including water, as well as gases.

SUMMARY OF THE INVENTION

The present invention, in some embodiments thereof, relates to carbon nanotube laminates and use thereof e.g., for filtration membranes.

According to an aspect of some embodiments of the present invention there is provided a composition comprising at least one laminate comprising porous carbon nanotube (CNT), wherein the laminate is characterized by one or more from:

(a) electrical conductivity of at least $10^3$ S/m;
(b) water permeability coefficient ($L_p$) in the range of 200 to 700 lmh/bar;
(c) comprising pores having a median size of from 15 nm to 150 nm;
(d) tortuosity factor of at least 1.7, and
(e) a length to thickness ratio of 800 to 1200.

In some embodiments, the composition is characterized by three or more from (a) to (e).

In some embodiments, the laminate is characterized by a thickness of 20 to 100 µm.

In some embodiments, the laminate is characterized by a root-mean-square (RMS) surface roughness of at least 20 nm.

In some embodiments, the one laminate is characterized by a static water contact angle of at least 70°.

In some embodiments, the laminate is characterized by thermal stability of up to at least 400° C.

In some embodiments, the one laminate is characterized by a density of from 0.1 gr/cm$^3$ to 1 gr/cm$^3$.

In some embodiments, the porous CNT has attached on one surface thereof one or more chemical functional groups.

According to an aspect of some embodiments of the present invention there is provided a article comprising the disclosed composition in any embodiment thereof.

In some embodiments, the article is selected from the group consisting of: an agricultural device, a microelectronic device, a microelectromechanic device, a photovoltaic device, or a microfluidic device.

In some embodiments, the article is a filtration membrane. In some embodiments, the filtration membrane is a self-supporting filtration membrane. In some embodiments, the filtration membrane is characterized by electrical conductivity that varies within less than ±10% along the length of the membrane.

In some embodiments, the filtration membrane is characterized by absolute pore rating of below 60 nm.

According to an aspect of some embodiments of the present invention there is provided a system comprising the disclosed article in any embodiment thereof, comprising a control unit configured to induce an electrical current along the length of the membrane.

In some embodiments, the system is identified as capable of inhibiting, reducing or retarding attachment of microbes on a surface of the membrane.

According to an aspect of some embodiments of the present invention there is provided a method for reducing the concentration of a contaminant in a fluid, comprising the step of contacting the fluid with the disclosed article in any embodiment thereof.

In some embodiments, the fluid is water.

In some embodiments, the contaminant is selected from the group consisting of a salt, a metal, a pathogen, a microbiological organism, an organic molecule, a protein, or a combination thereof.

According to an aspect of some embodiments of the present invention there is provided a method of inhibiting, reducing and/or retarding a biofilm formation on a surface of the disclosed article in an embodiment thereof, the method comprising applying electrical current in portion of the article.

In some embodiments, the method is affected under electric potential implemented on the article, of at least 1000 mV.

In some embodiments, the electrical current is alternating current (AC).

In some embodiments, the AC has a frequency in the range of 1 Hz to 10 kHz.

In some embodiments, the electrical current is direct current (DC).

In some embodiments, the method is affected under electric potential implemented on the article of at least 1000 mV.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-I present morphology of carbon nanotube (CNT) laminates (detailed structural characterization of the C-80 laminates are described below): Figures-A-C show high resolution scanning electron microscopy (HR-SEM) micrographs of C-80 as is, stretching modified and acetone modified laminates at a magnification of 30× (FIGS. 1 A-C), thin section of the top layer was carefully peeled off from the laminates (FIGS. 1 D-F), and Atomic-force microscopy (AFM) topography of CNT laminates (FIG. 1 G-I).

Figure 2A:
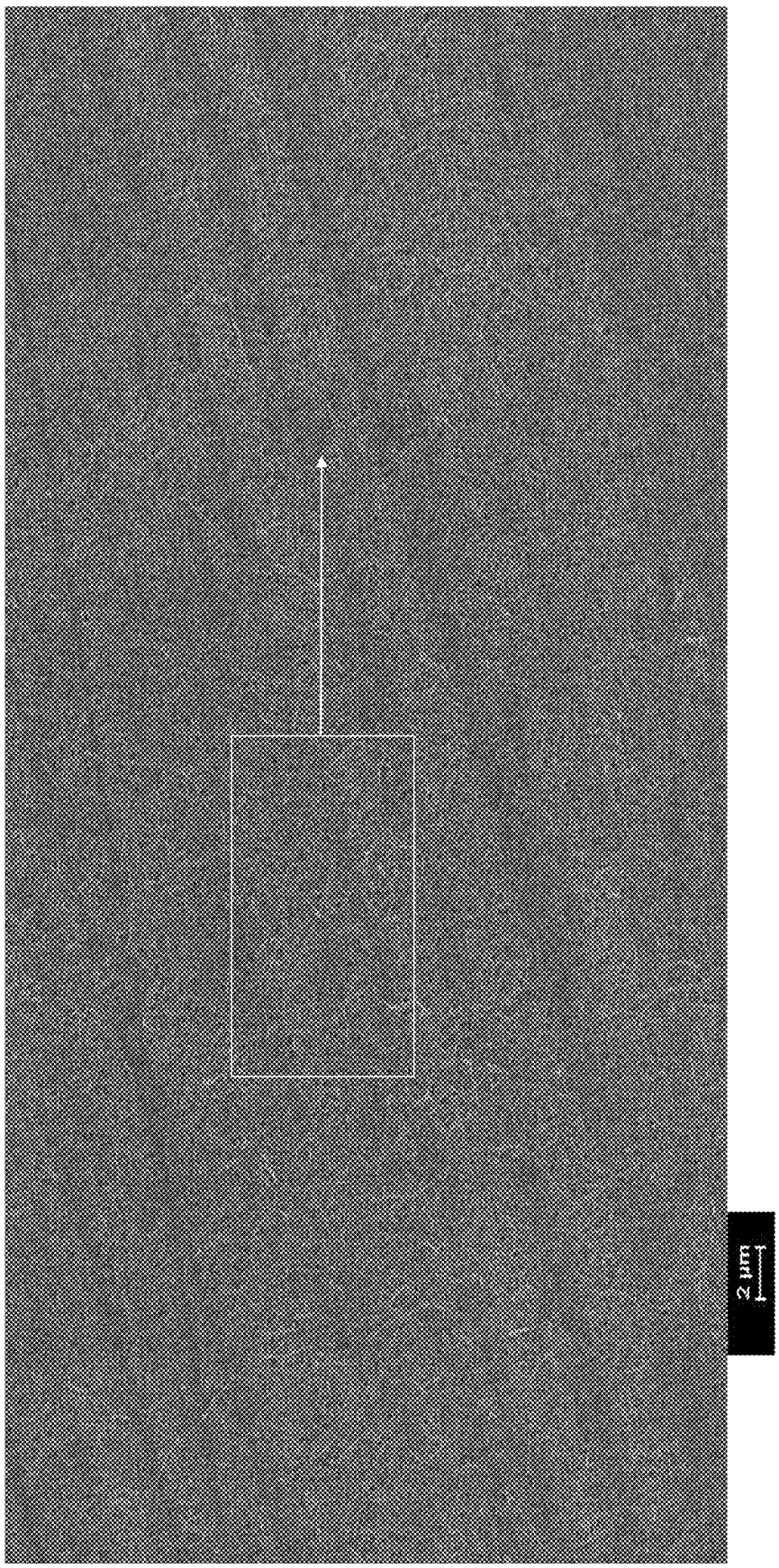
Figure 2B:
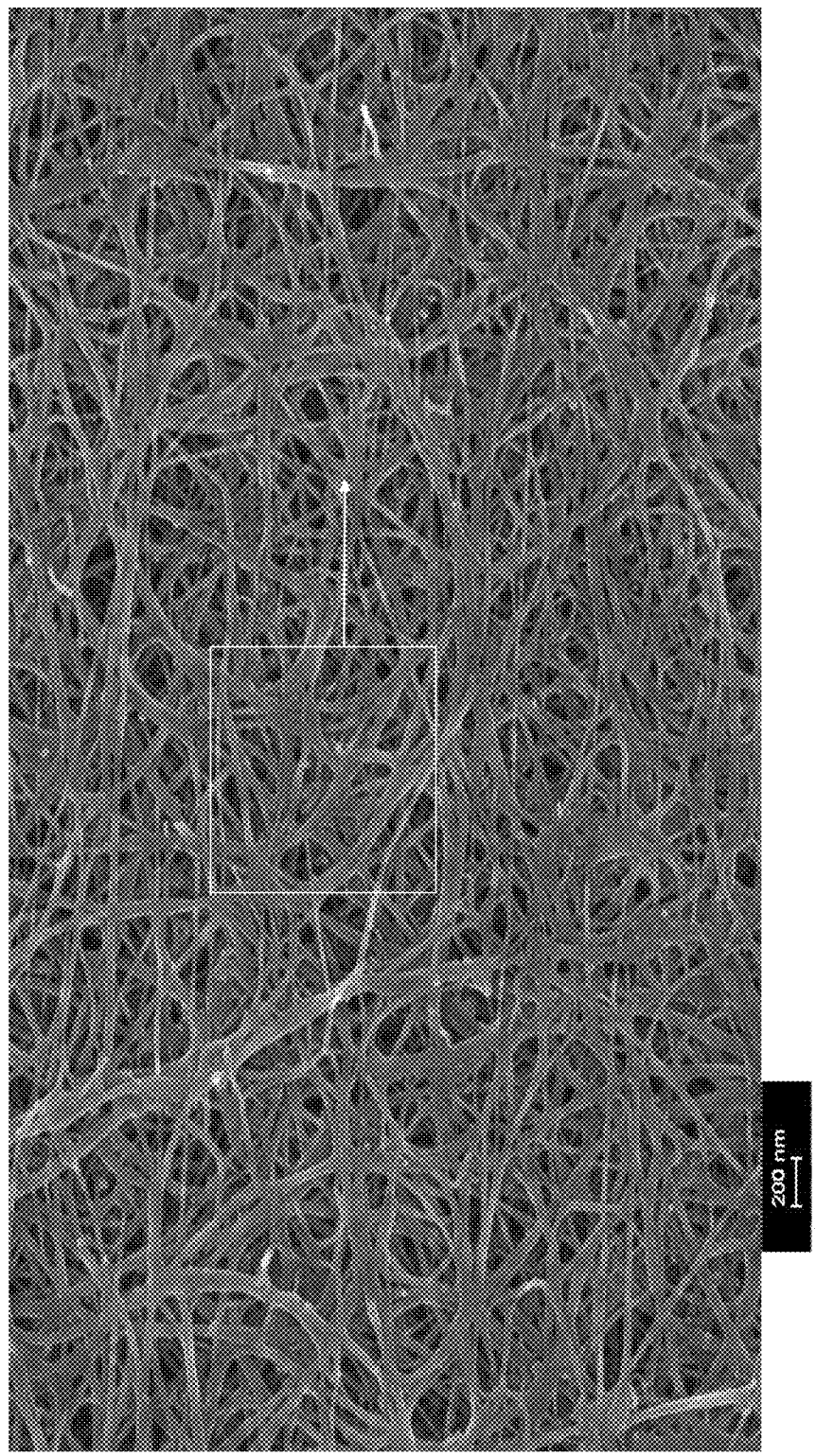
Figure 2C:
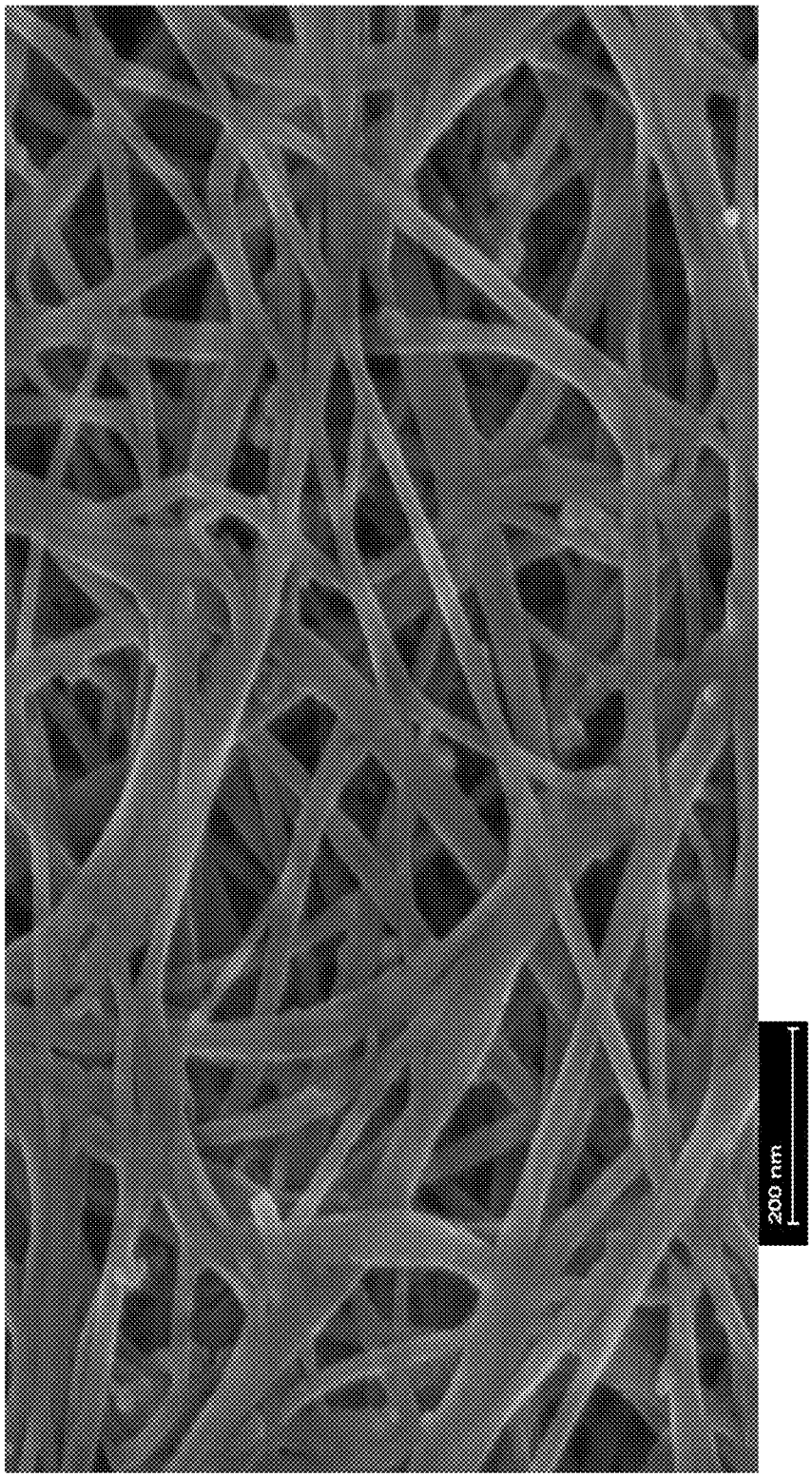
Figure 2D:
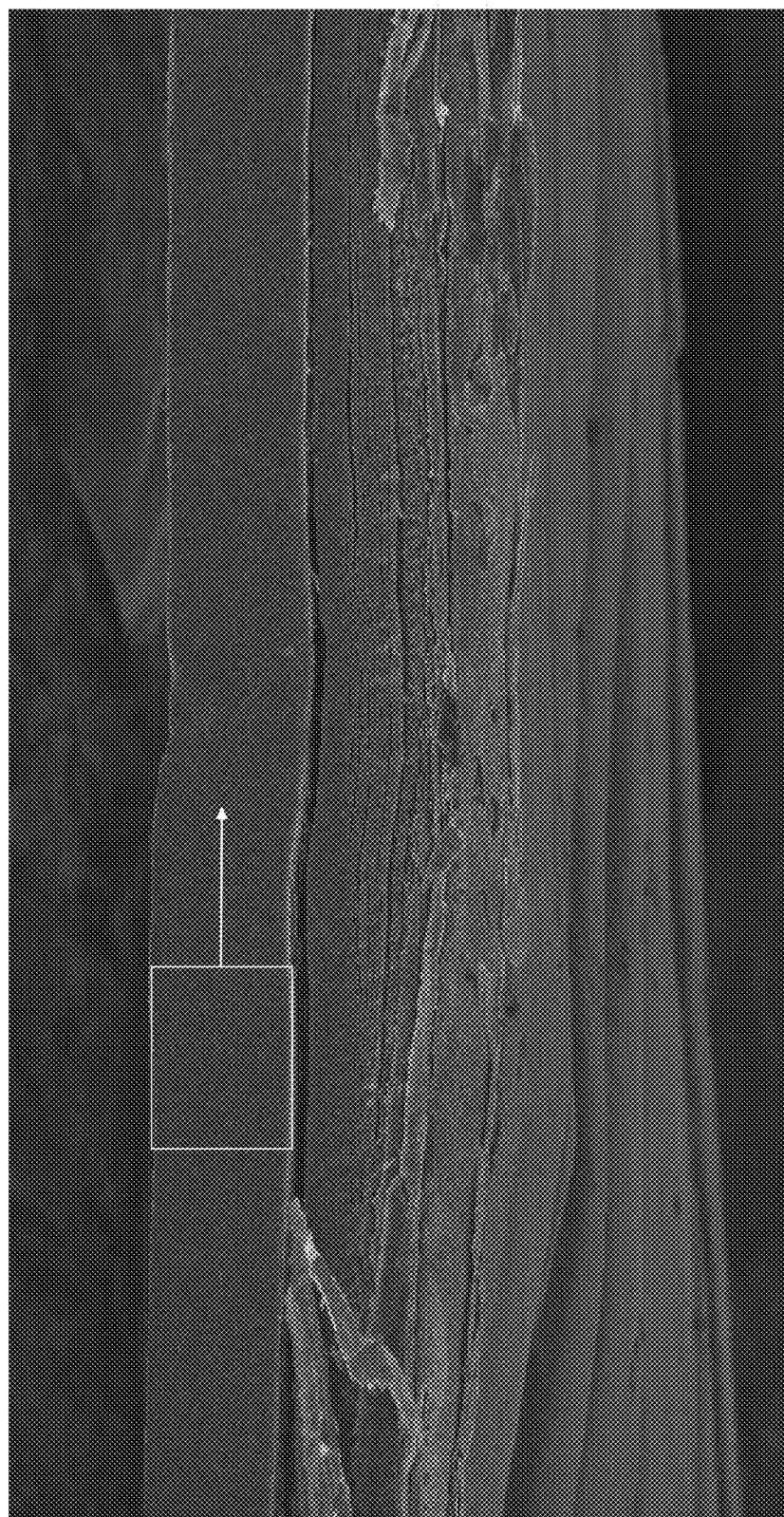
Figure 2E:
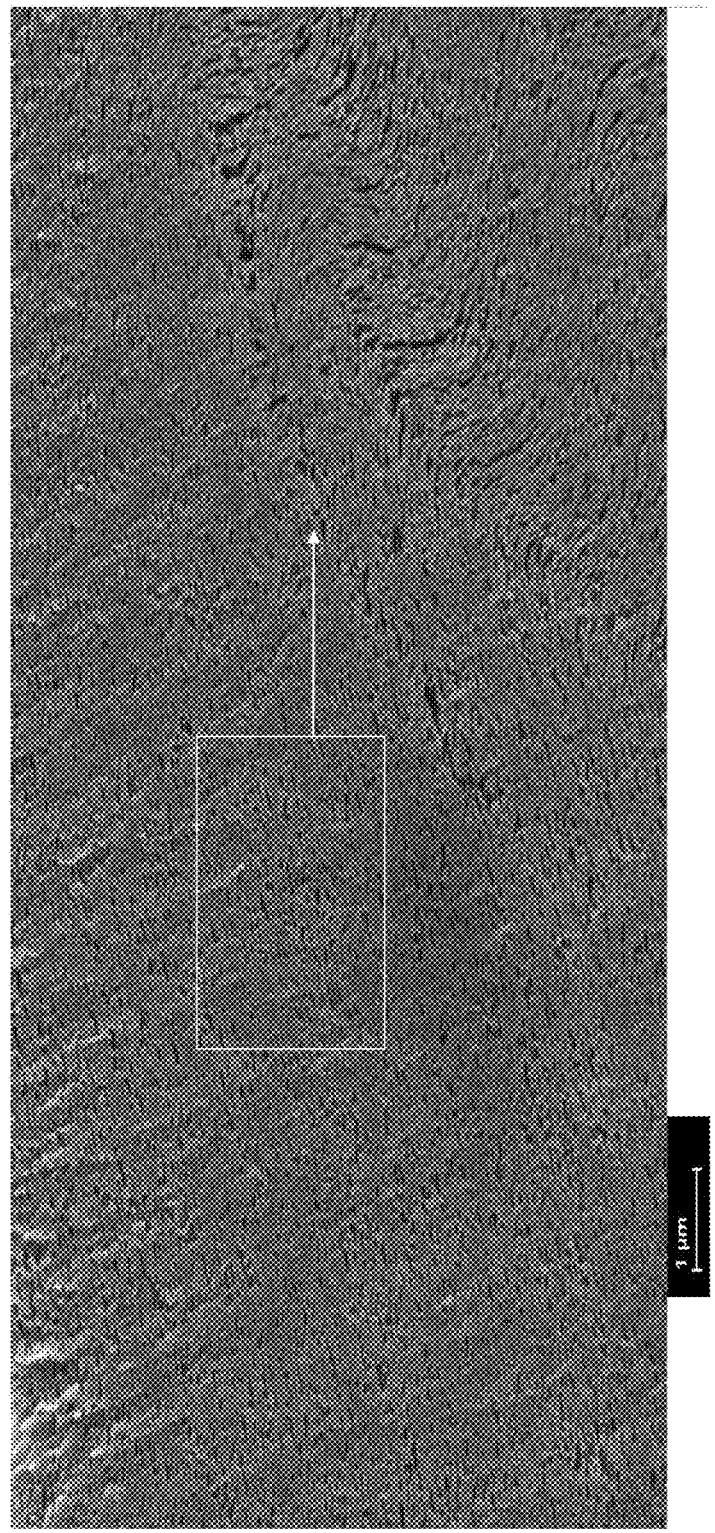
Figure 2F:
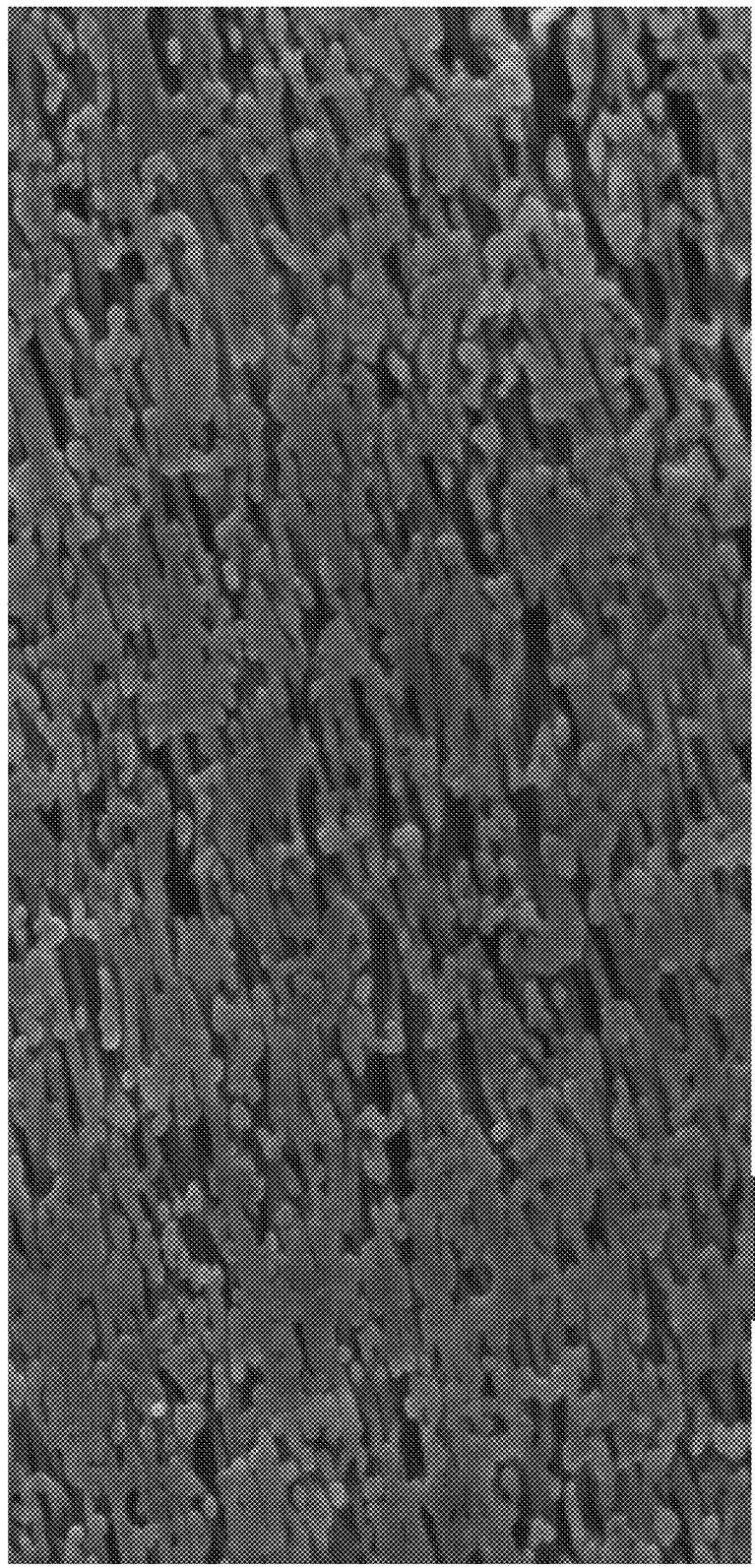

FIGS. 2A-F present surface and cross section morphology of C-80 membrane 5 KX (FIG. 2A), 50 KX (FIG. 2B), 300 KX (FIG. 2C), 2.5 KX (FIG. 2D), 20 KX (FIG. 2E), 100 KX (FIG. 2F) (FIGS. 2D, E, F—cross section images).

Figure 3:
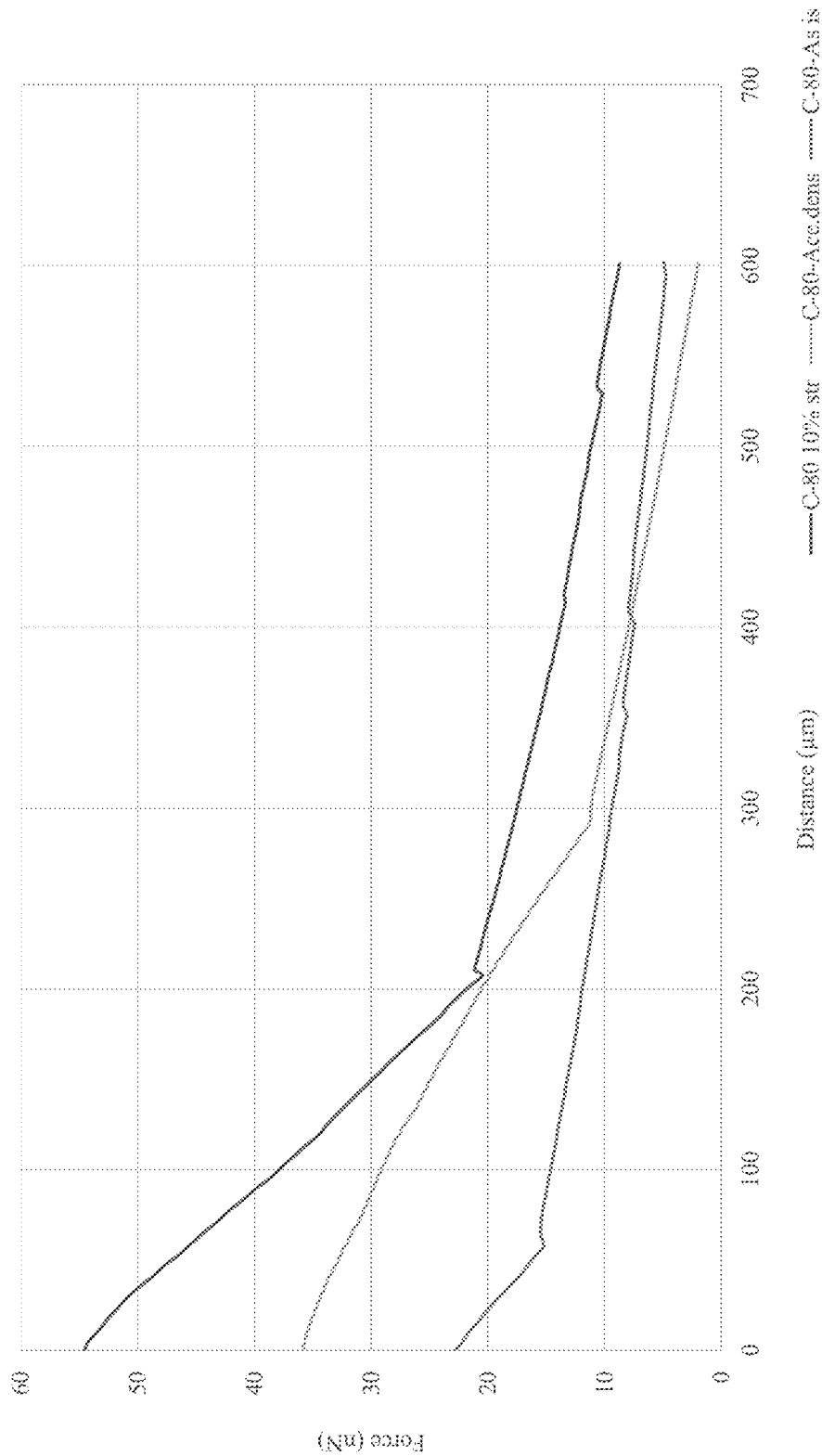

FIG. 3 presents graphs showing AFM tip—CNT surface interaction forces as functions of the separation distance. Measurements were performed in constant force mode (50 nN) with a gold coated Si tip. The scans were performed at a rate of 0.5 Hz with a resonance frequency of 13 kHz, k=0.2 N/m, where k is the spring constant of the cantilever.

Figure 4A:
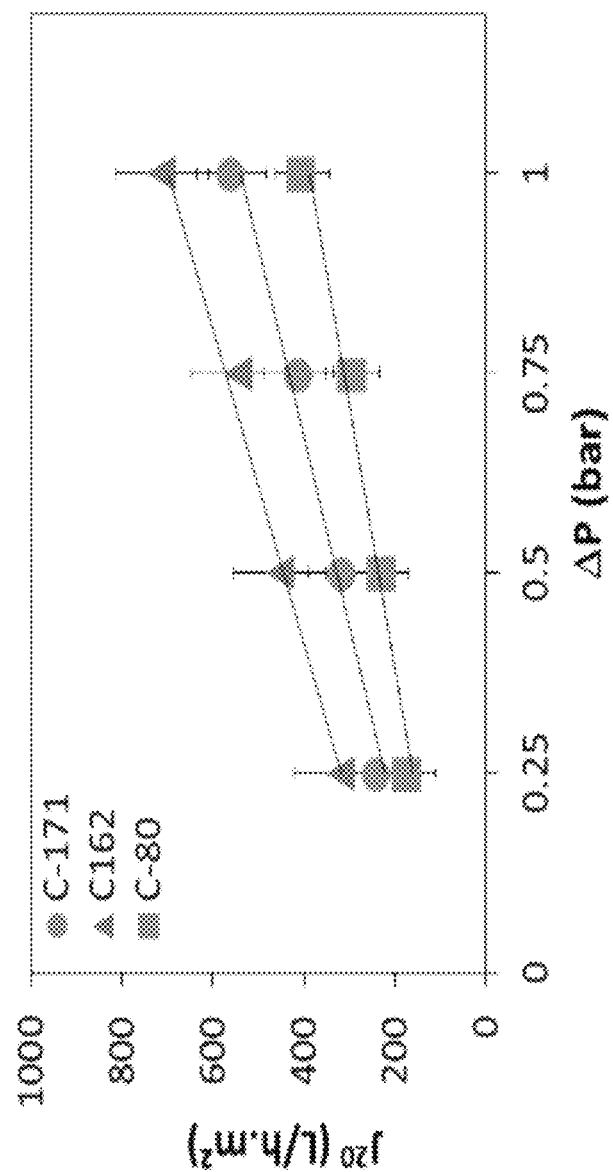
Figure 4B:
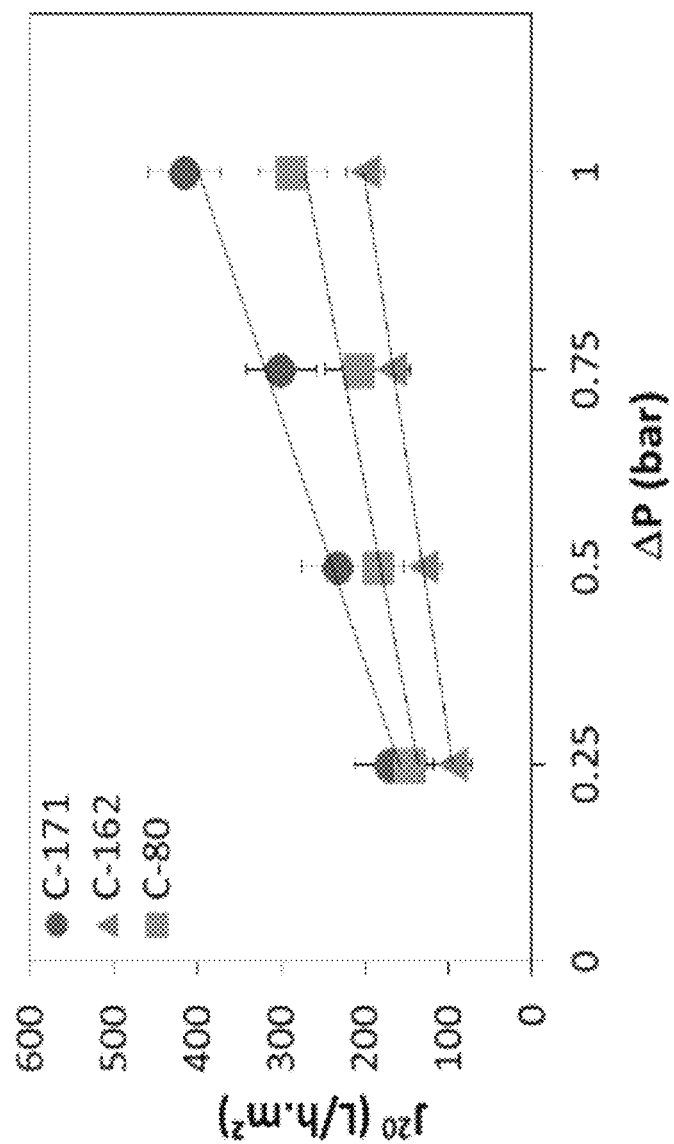
Figure 4C:
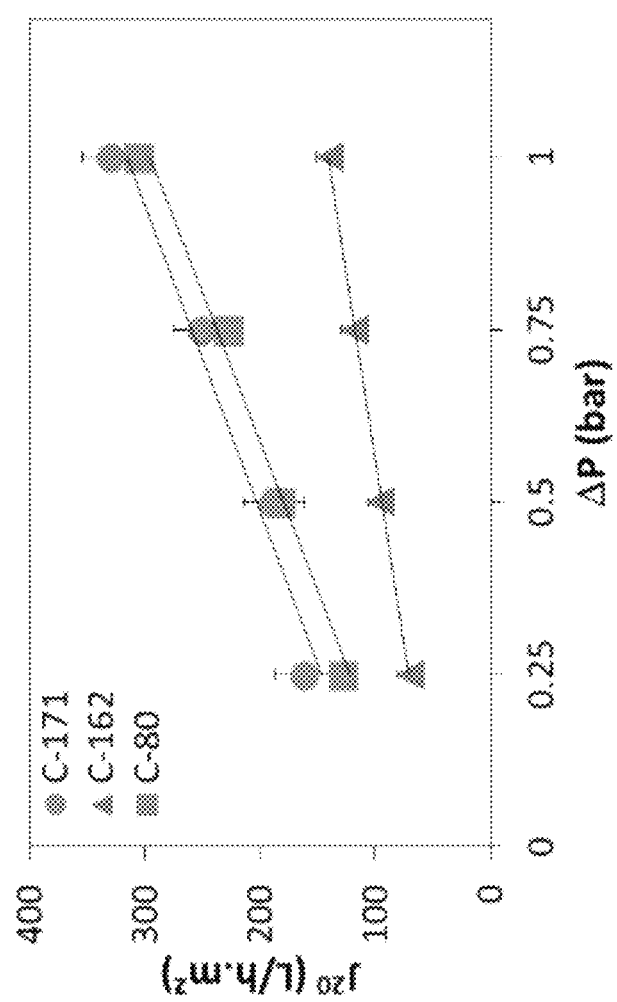

FIGS. 4A-C present graphs showing normalized water permeability values of the different CNT laminates tested: unmodified (FIG. 4A), stretched (FIG. 4B), and acetone densified (FIG. 4C).

Figure 5:
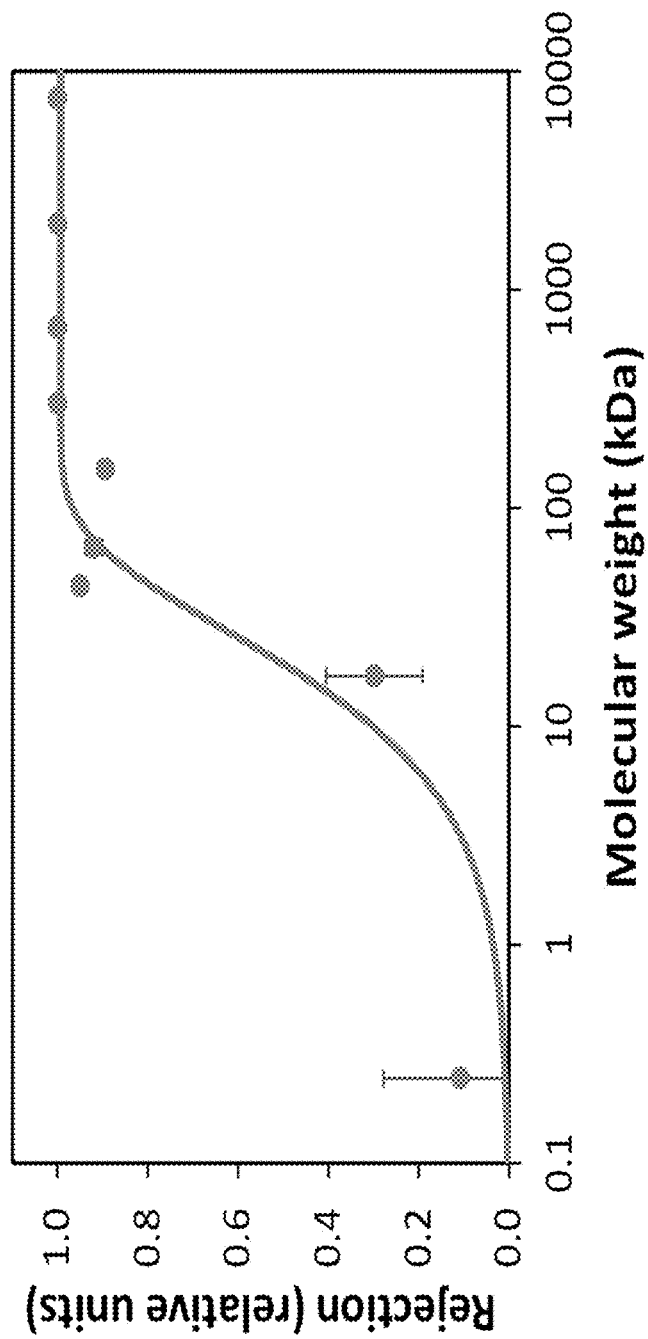

FIG. 5 presents graph showing semi-logarithmic plot of rejection vs. molecular weight for the C-80 unmodified membrane using globular proteins (17-670 kDa), blue dextran (2,000 kDa) and fluorescent beads (40-900 nm) markers; "■": empirical data; "——": fit to Ferry-Renkin equation (Eq. 6); Data represent average±standard deviation of at least three replicates.

Figure 6:
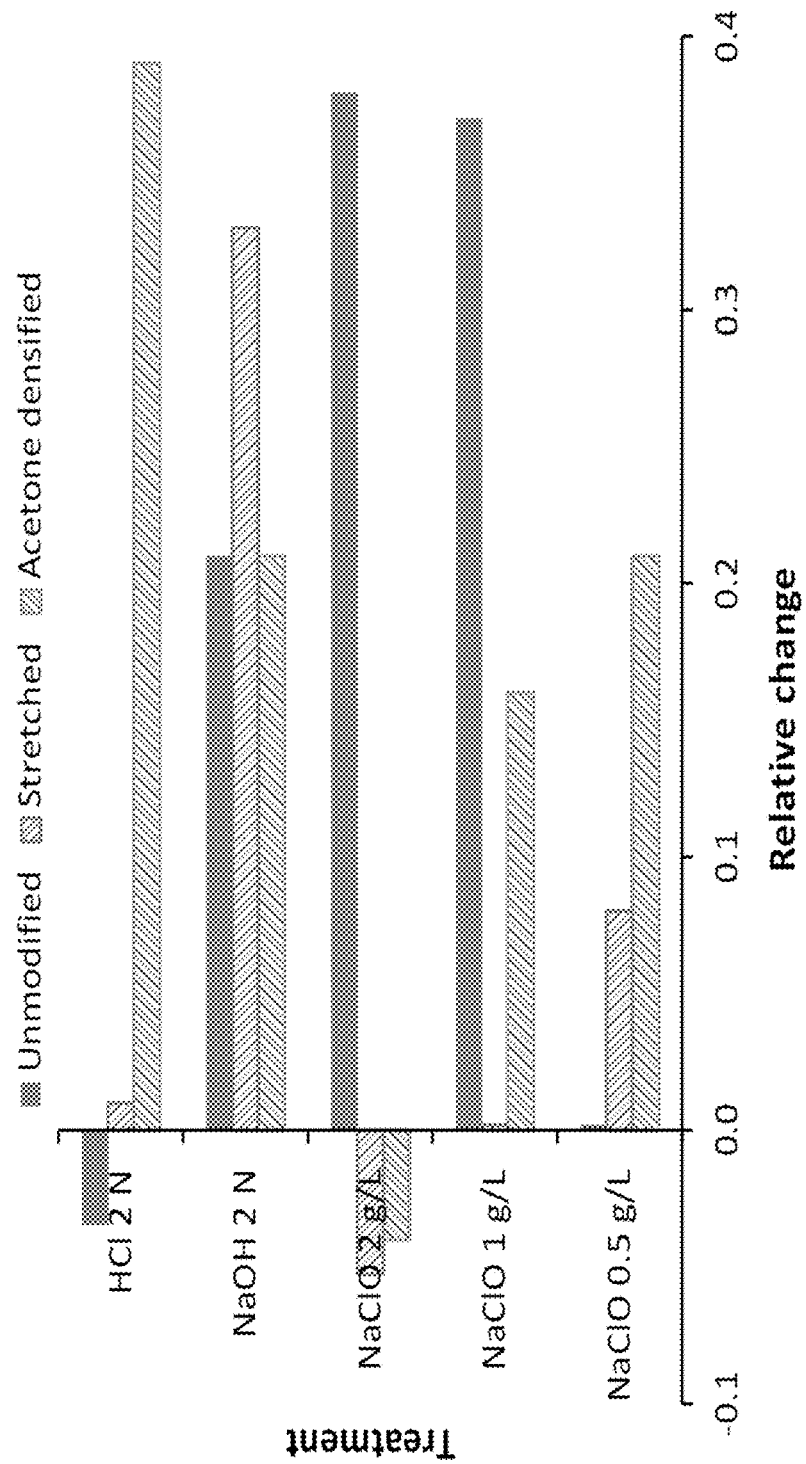

FIG. 6 presents a bar graph showing the relative change in pore rating of C-80 membranes before and after chemical resistance tests. Values represent relative values towards the control (untreated). Pore rating was calculated according to Eqs. 4-6. Pore rating of untreated (control) membranes are given in Table 1 below.

Figure 7D:
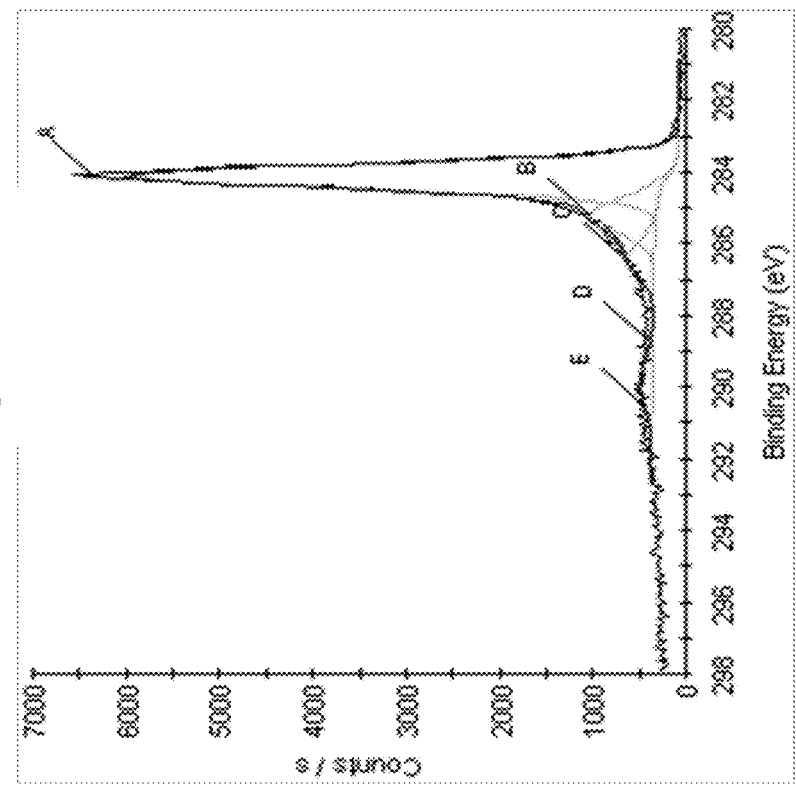
Figure 7C:
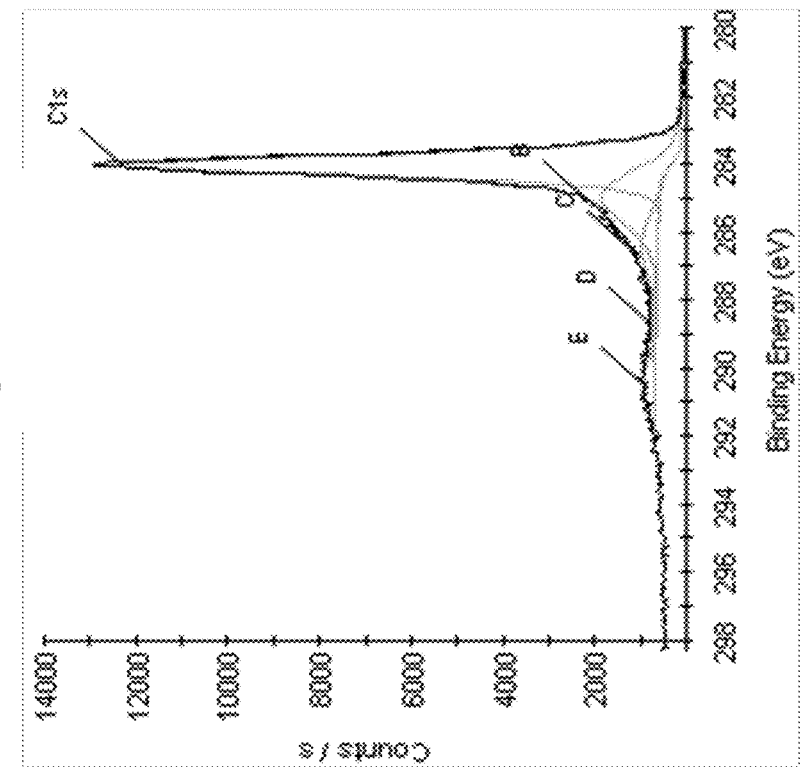

FIGS. 7A-D present X-ray photoelectron spectroscopy (XPS) graphs of CNT C-80 laminates after chemical resistance tests: control (pristine laminate) (FIG. 7A), 2N HCl (FIG. 7B), 2000 mg/L NaOCl (FIG. 7C), and 2N NaOH (FIG. 7D). After deconvolution, the C1s line showed a main peak at 284.0 eV (peak#A) that was attributed to the graphitic structure ($sp^2$ hybridized). The peak at 285.1 eV (peak#B) was either attributed to $sp^3$—hybridized carbon or defects due to carbon atom that are no longer in the original tubular structure, whereas following peaks 286.4 eV (peak#C), and 288.4 eV (peak#D) are indicative of different oxygen based functionalities at the chemical environment of the carbon atoms. Finally the peak#E (at 290 eV) is related to $\pi$-$\pi^*$ transition loss peak.

Figure 8:
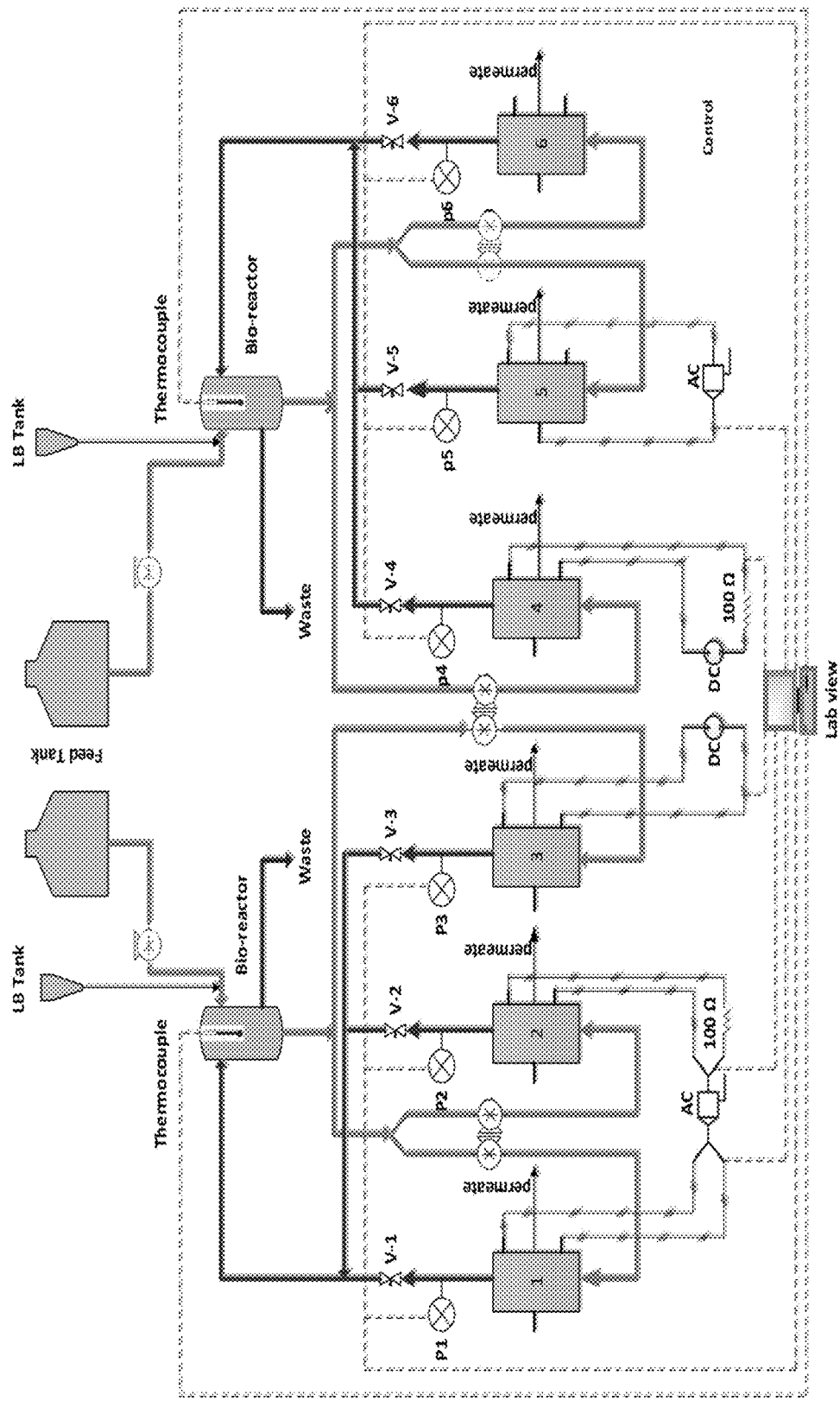

FIG. 8 presents a scheme showing a recirculating reactor using a peristaltic pump.

Figure 9A:
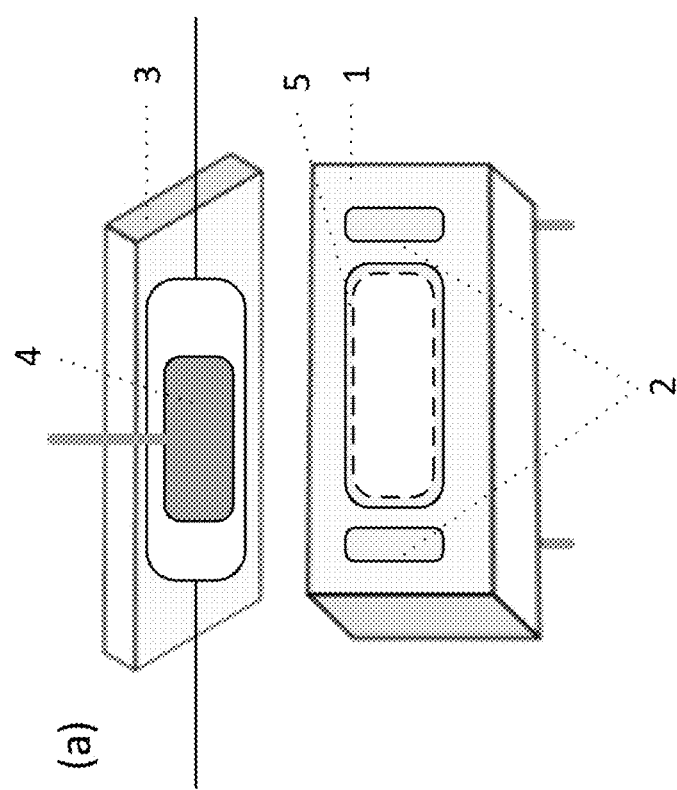
Figure 9B:
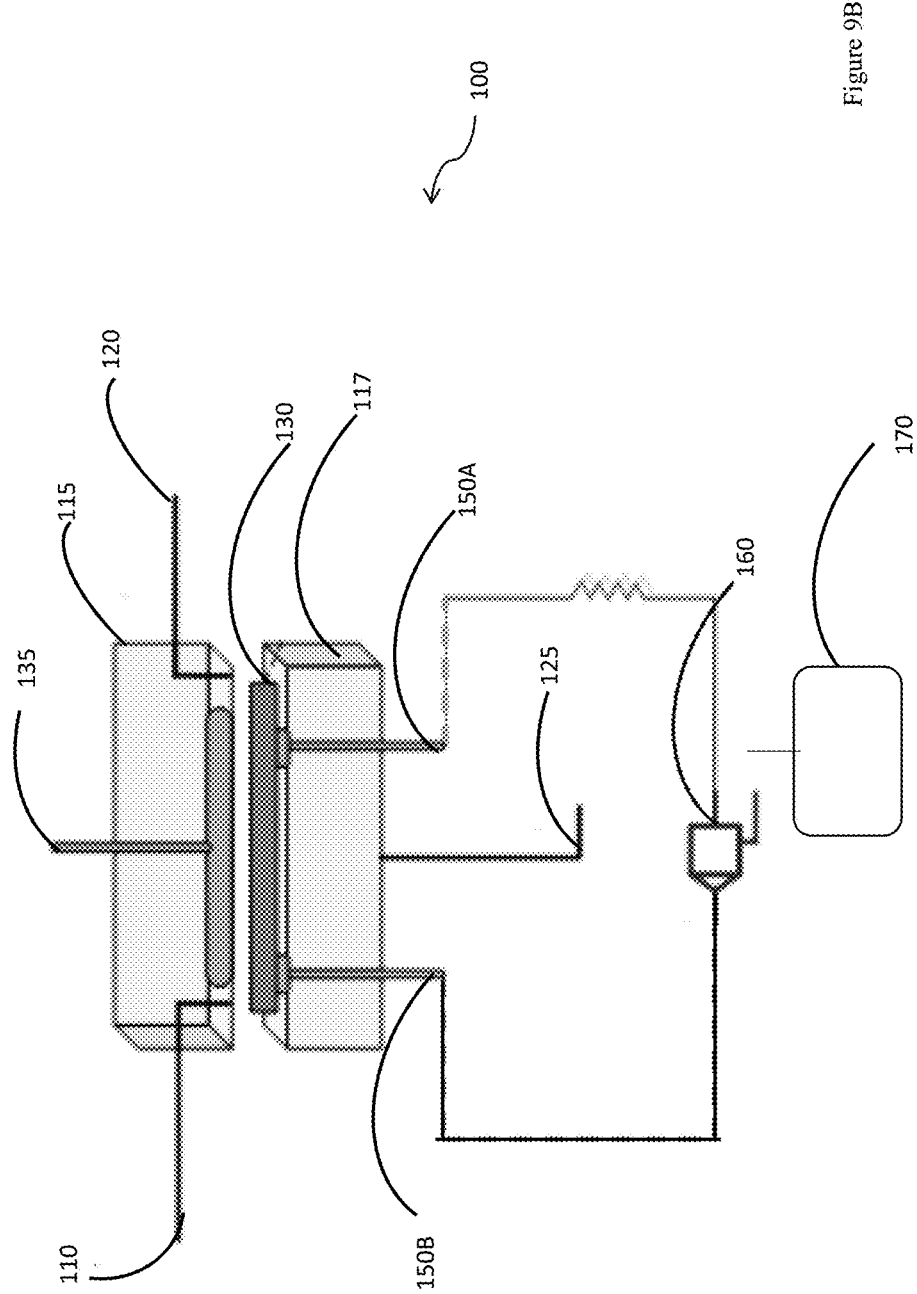
Figure 9C:
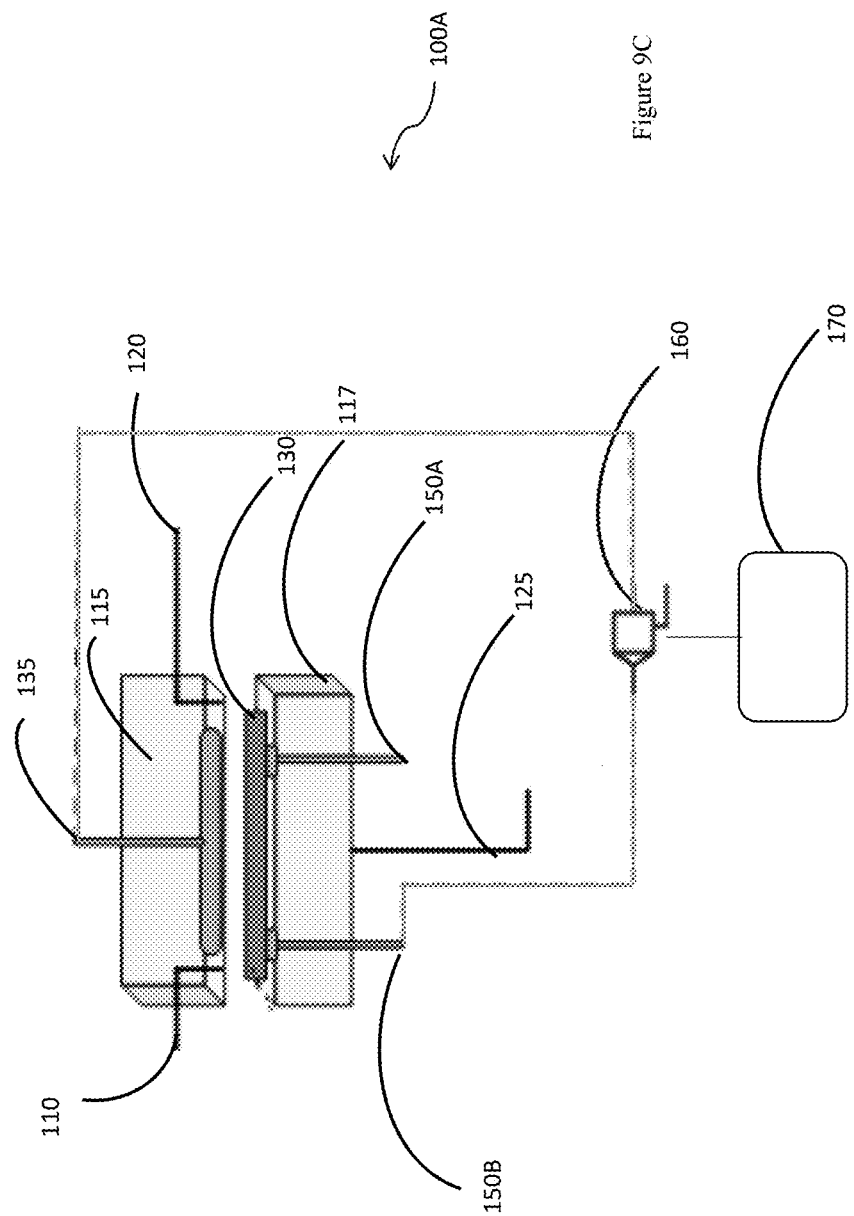

FIGS. 9A-C present a schematic diagram of a membrane cell design (FIG. 9A; "1" denotes cell bottom, "2" denotes electrode strip in bottom cell; "3" denotes cell top; "4" denotes electrode in top cell, and "5" denotes O-ring), and membrane cell in which the electric circuit is along the membrane (resistive mode) design (FIG. 9B), and membrane cell in which the electric circuit is across the membrane (capacitive mode) design (FIG. 9C).

Figure 10:
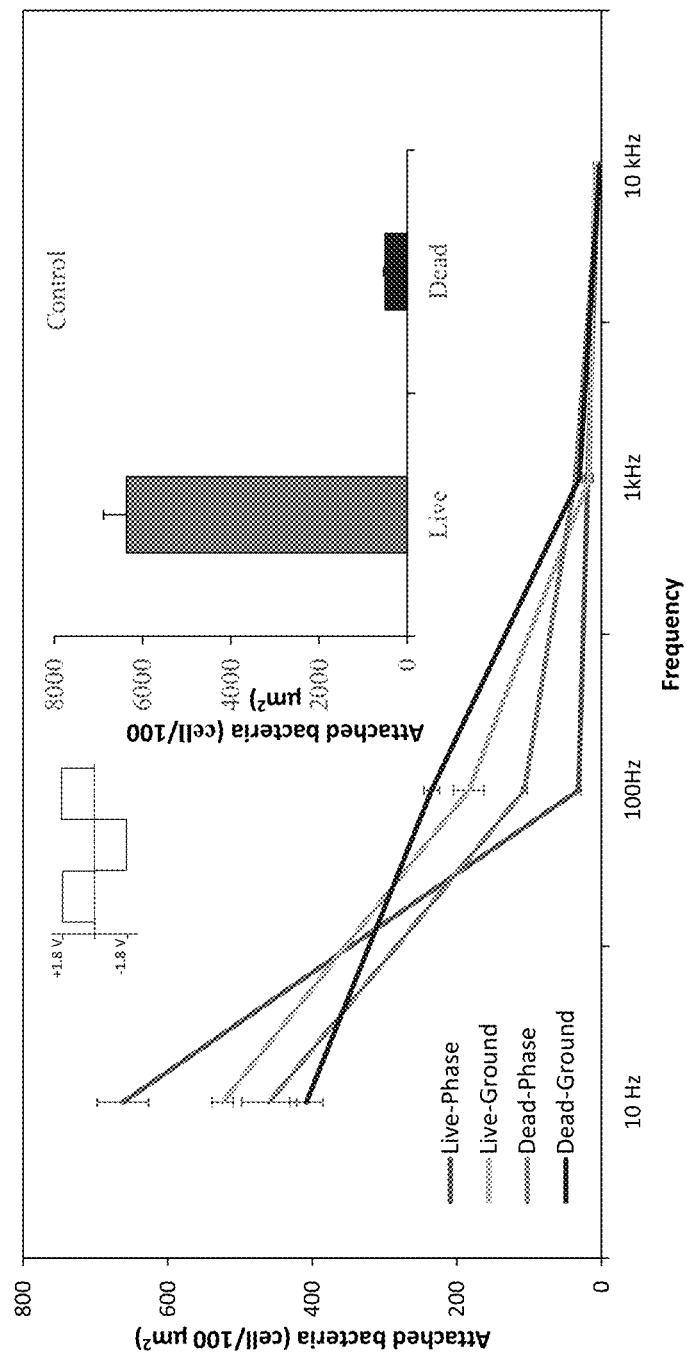
Figure 11:
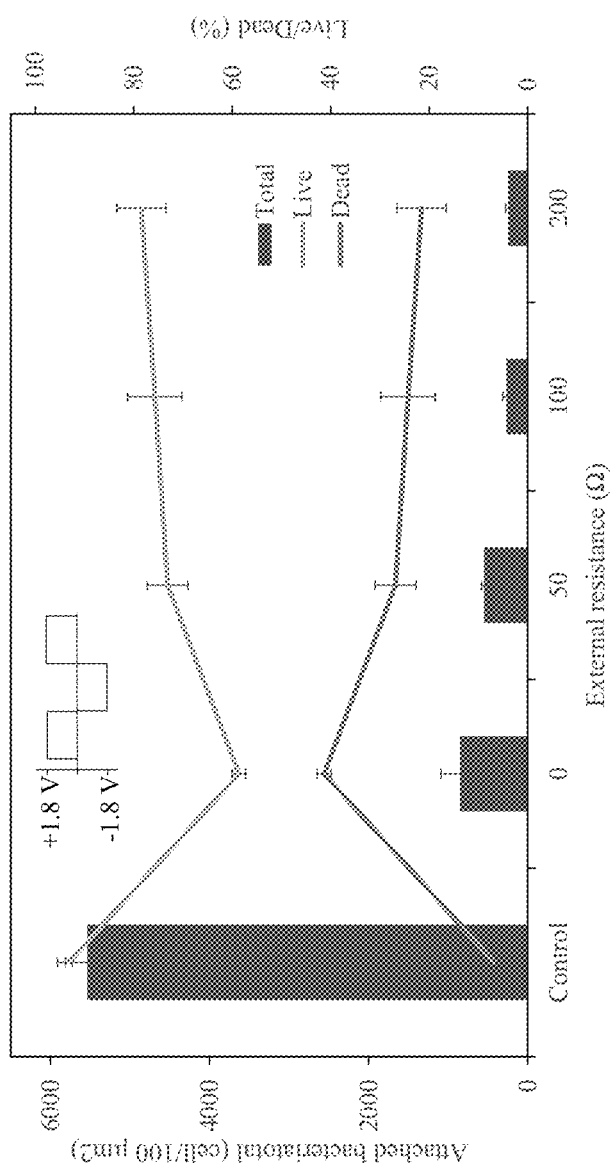

FIG. 10 presents a graph (and a bar graph in the inset) showing the influence of Alternating Current (AC) frequency in the range of 10 Hz to 10 kHz at 1800 $mV_{pp}$ (at offset with 50% duty cycle) on the attachment of bacteria on CNT membranes.

Figure 11:
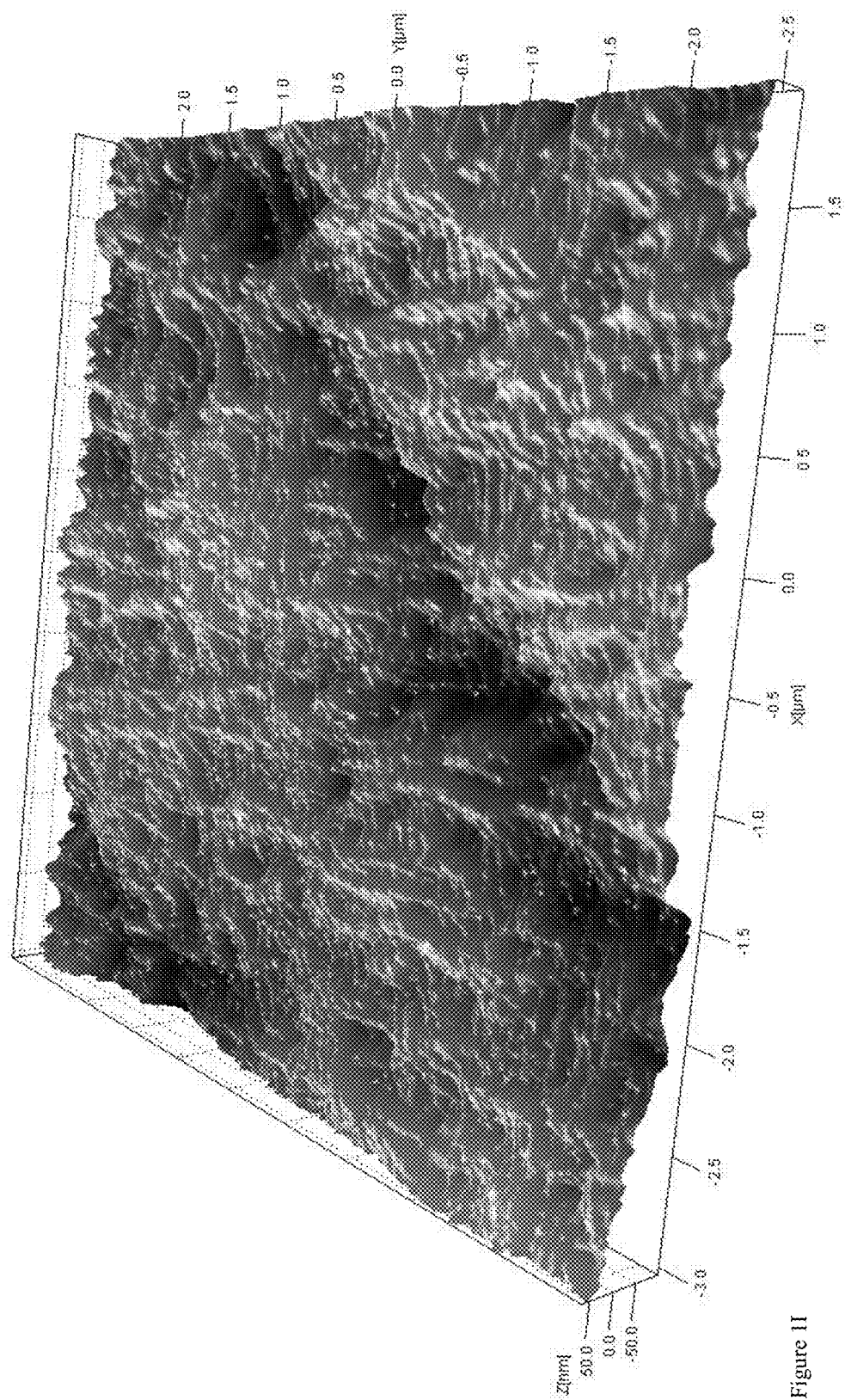

FIG. 11 presents graphs demonstrating the influence of the addition of an external resistance on prevention of bacterial attachment on the CNT membranes at 1800 $mV_{pp}$.

Figure 12:
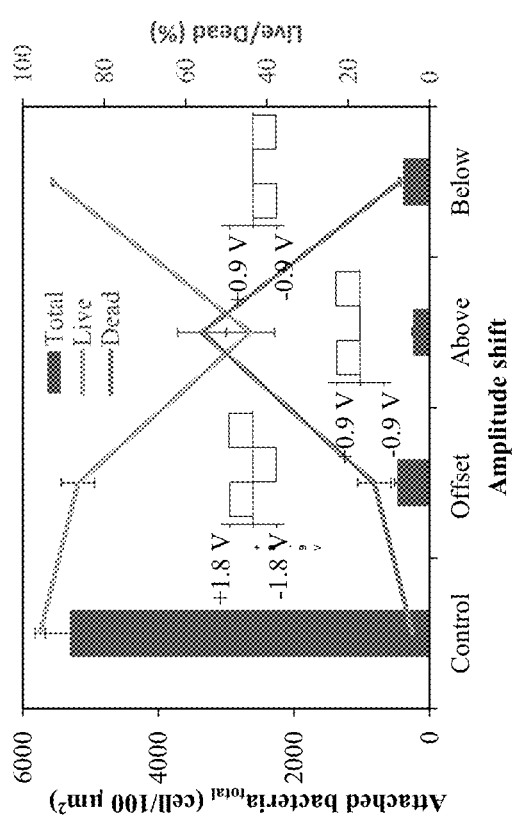
Figure 13A:
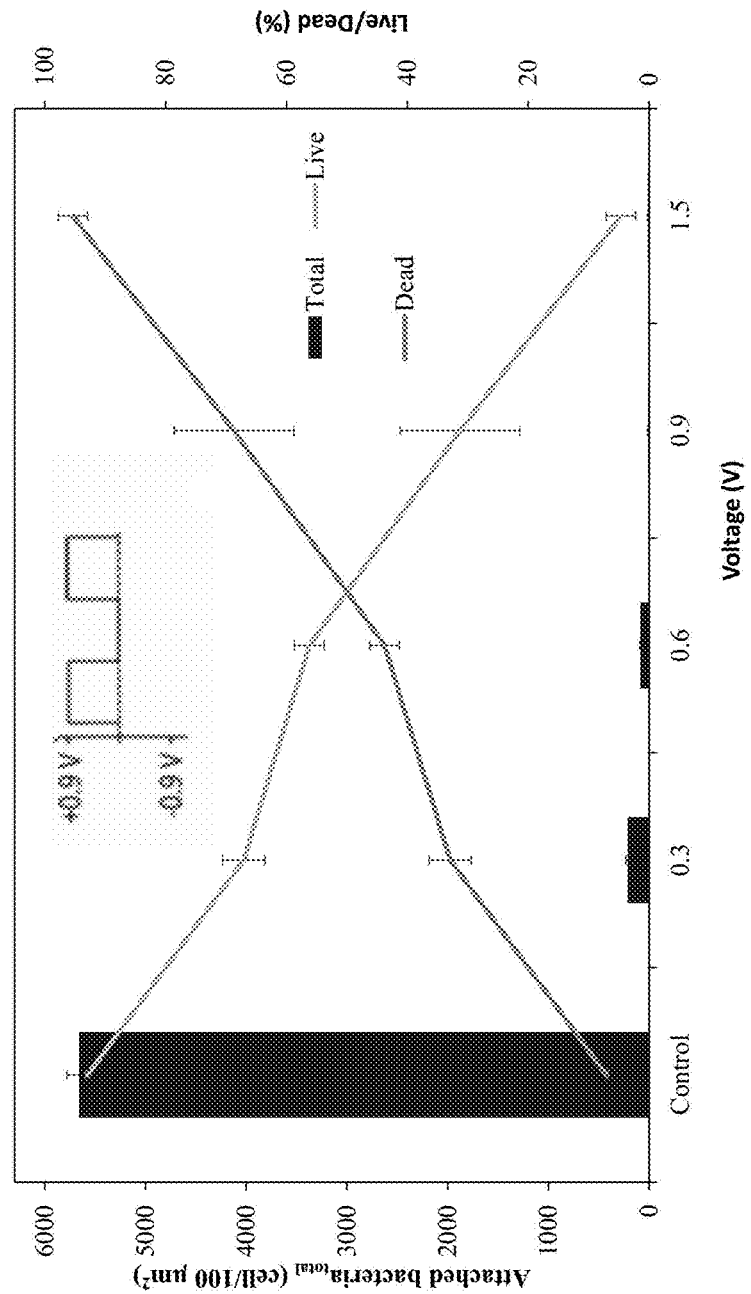
Figure 13B:
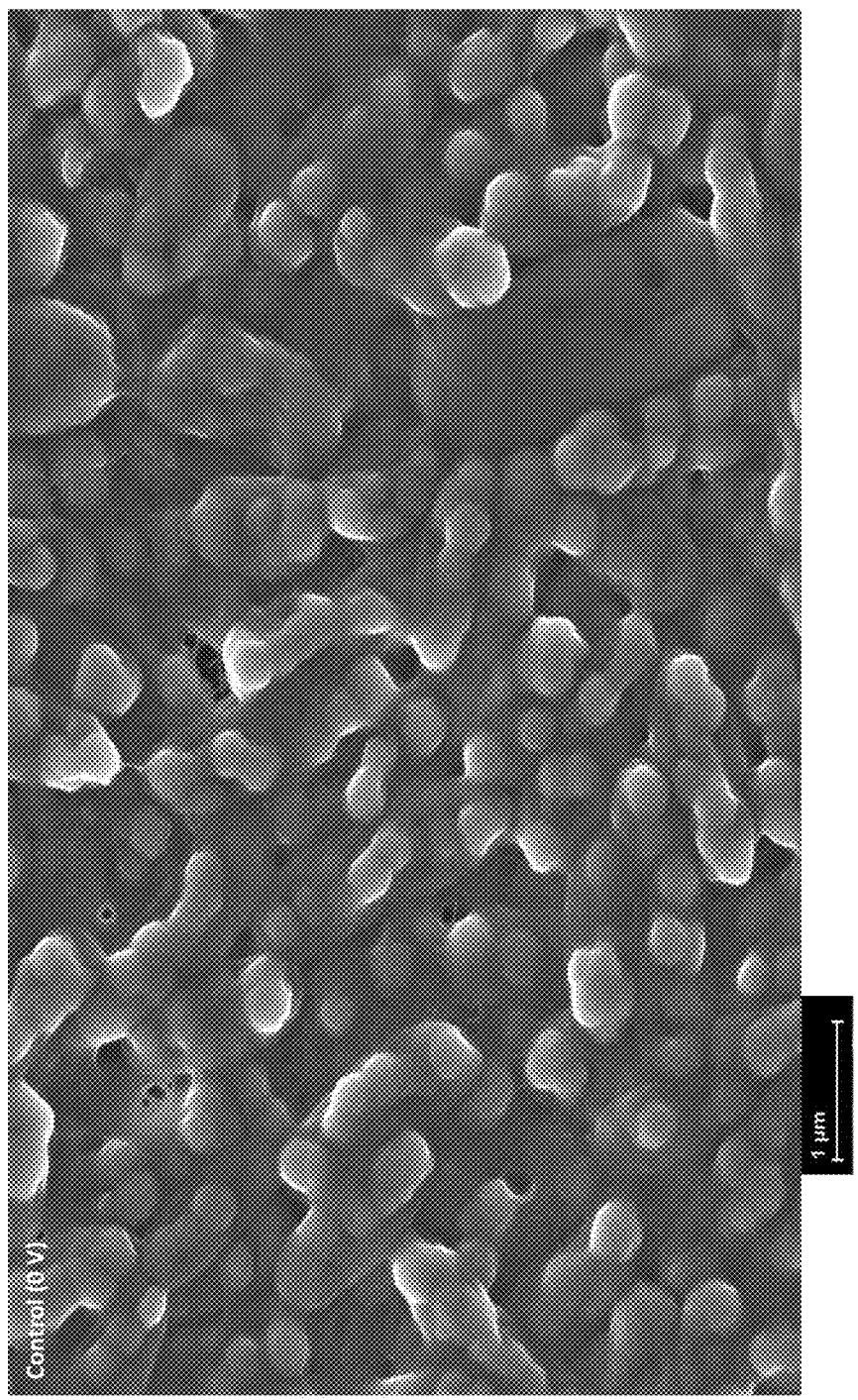
Figure 13C:
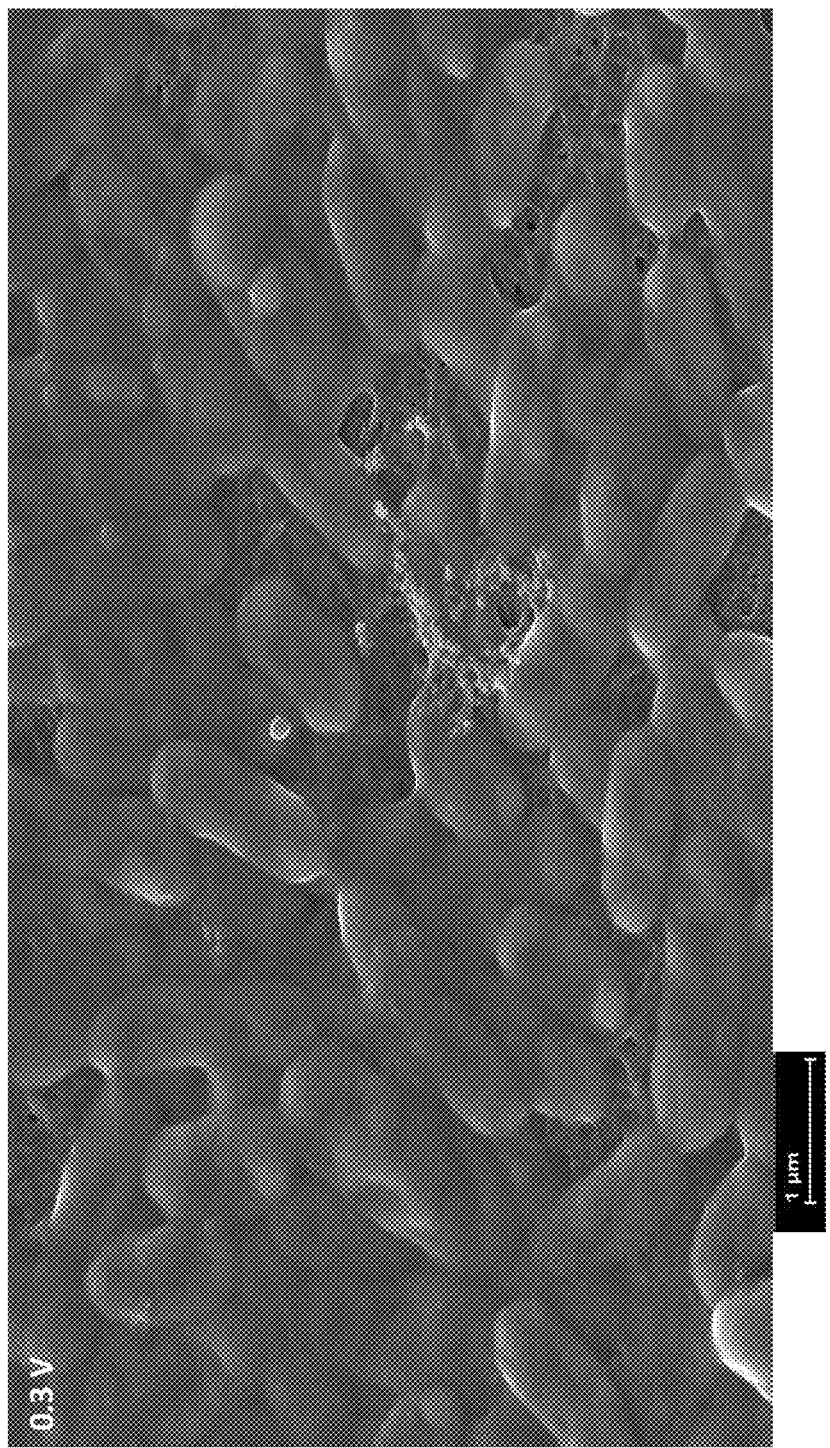
Figure 13D:
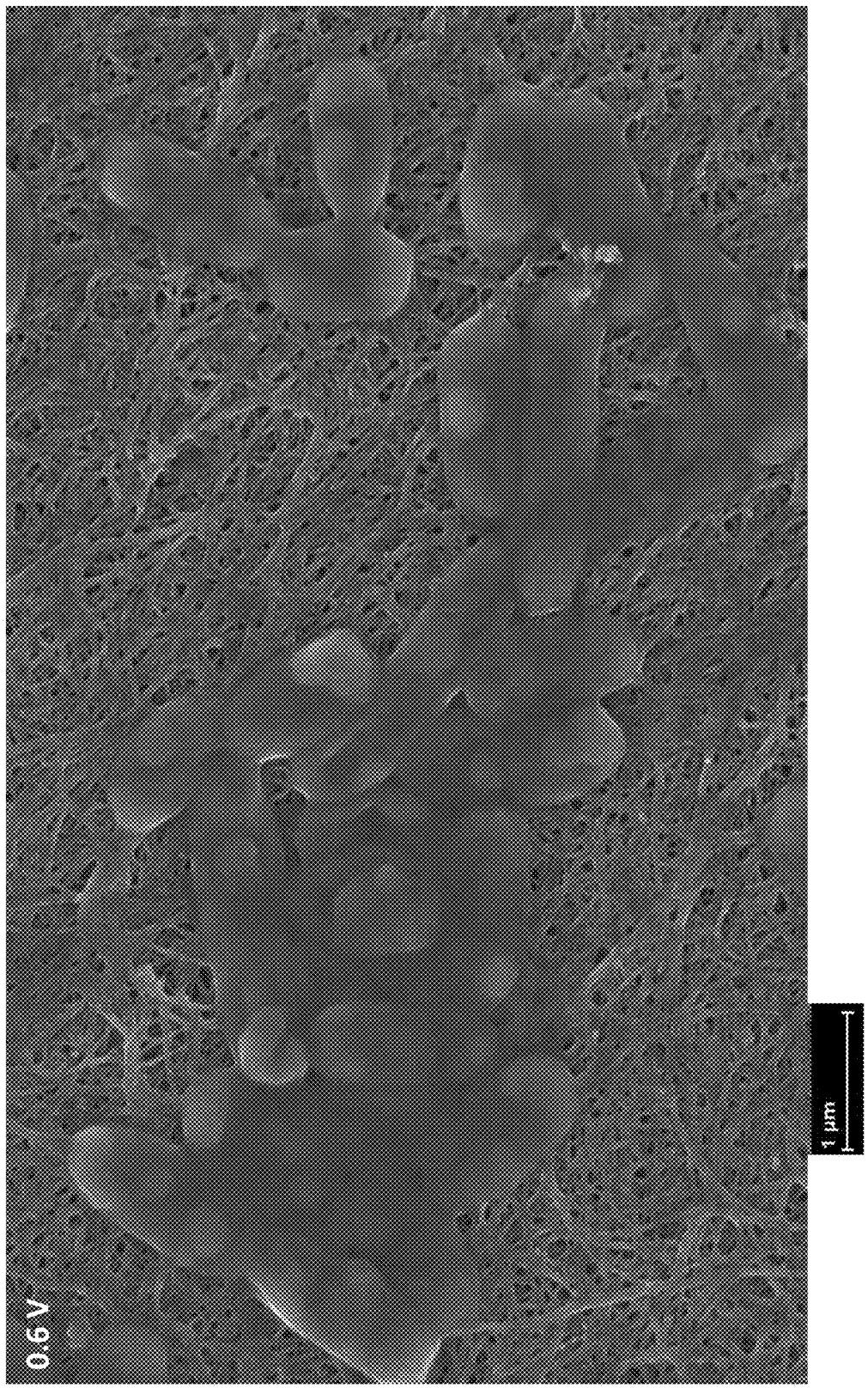
Figure 13E:
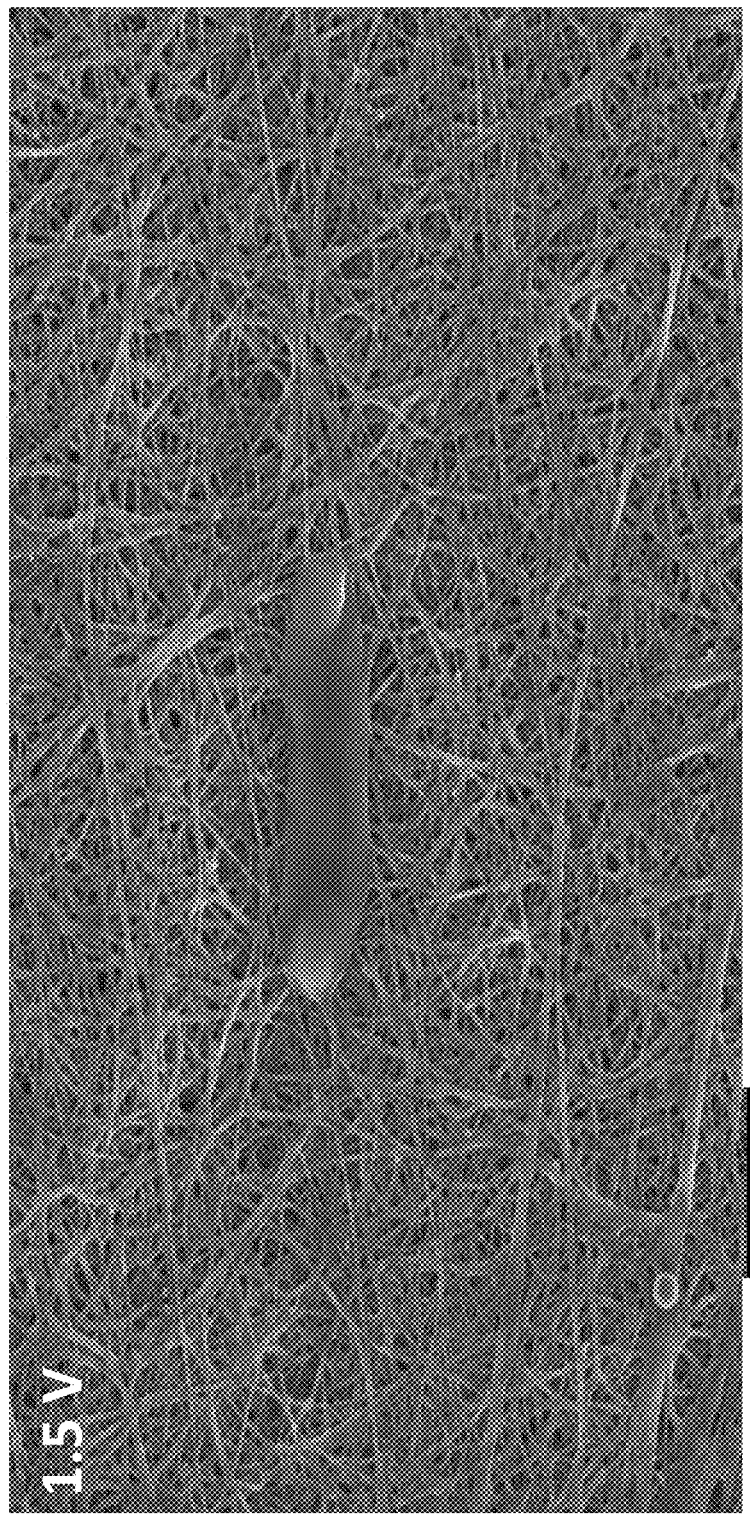
Figure 13F:
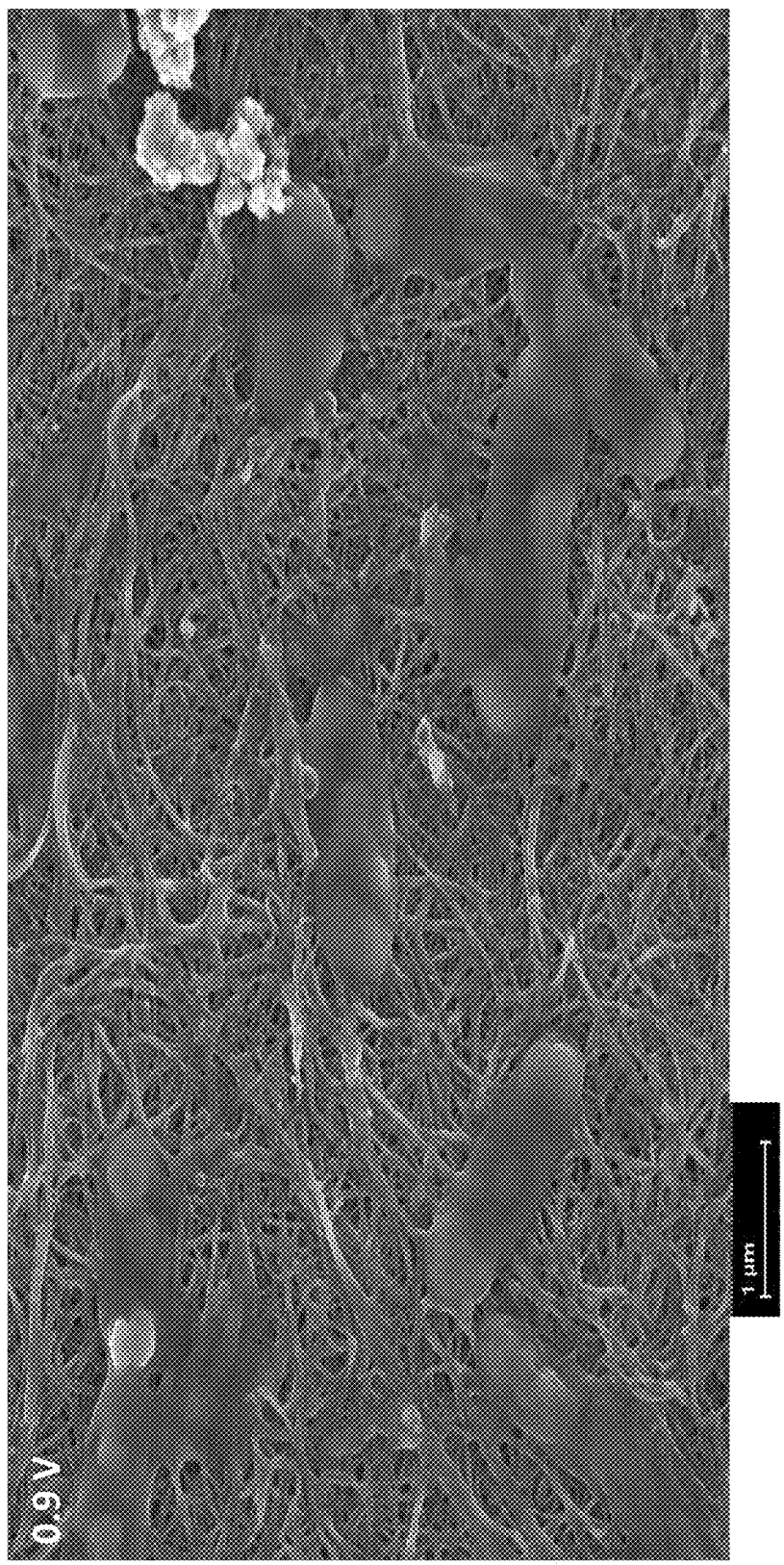

FIG. 12 presents graphs demonstrating the antibiofouling/inactivation capabilities of the AC in resistive mode: a wave pulse shift was tested above (+0.45, positive potential) and below (−0.45, negative potential) offset and compared with offset. A constant AC potential at 1 kHz frequency and 100Ω external resistance was applied, meaning −900 to +900 mV at offset (1800 $mV_{pp}$), 0 to 1800 mV above offset and −1800 to 0 mV below offset.

FIGS. 13A-F present graphs (FIG. 13A at the corresponding AC potential, see inset) and corresponding SEM micrographs showing the influence of the AC voltage in resistive mode on antibiofouling/inactivation capabilities on the CNT membranes studied in the range of 0-1500 mV (FIG. 13B-13F).

Figure 14A:
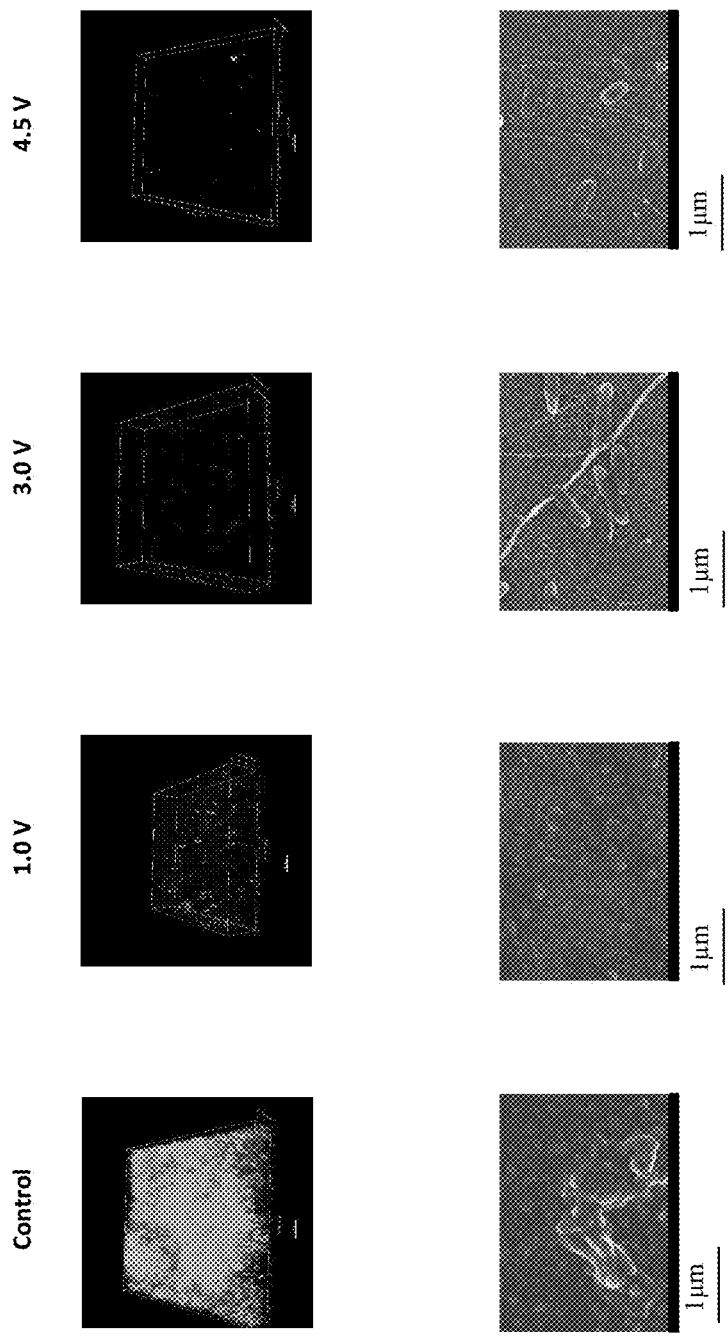
Figure 14B:
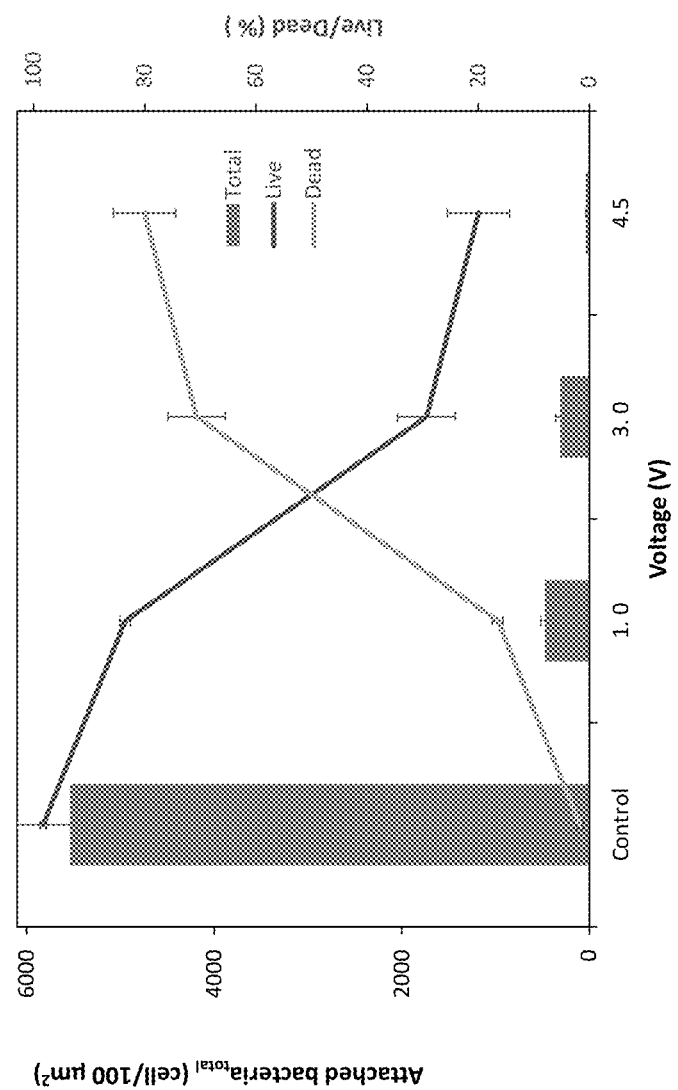

FIGS. 14A-B present the influence of the increase of the applied AC potential on the increase of dead cells numbers: Confocal scanning laser microscopic images (upper panel) of dead/live stained bacteria attached on the membranes after 72 h incubation, and HRSEM micrographs (lower panel) (FIG. 14A); and graphs display Imaris quantification of CLSM images (average±standard deviation of at least 3 replicates) (FIG. 14B). Control, no current. Electrical field conditions were: 1 kHz frequency, square wave above offset (+0.45), 50% duty cycle. Current sign shows wave shape and bias.

Figure 15:
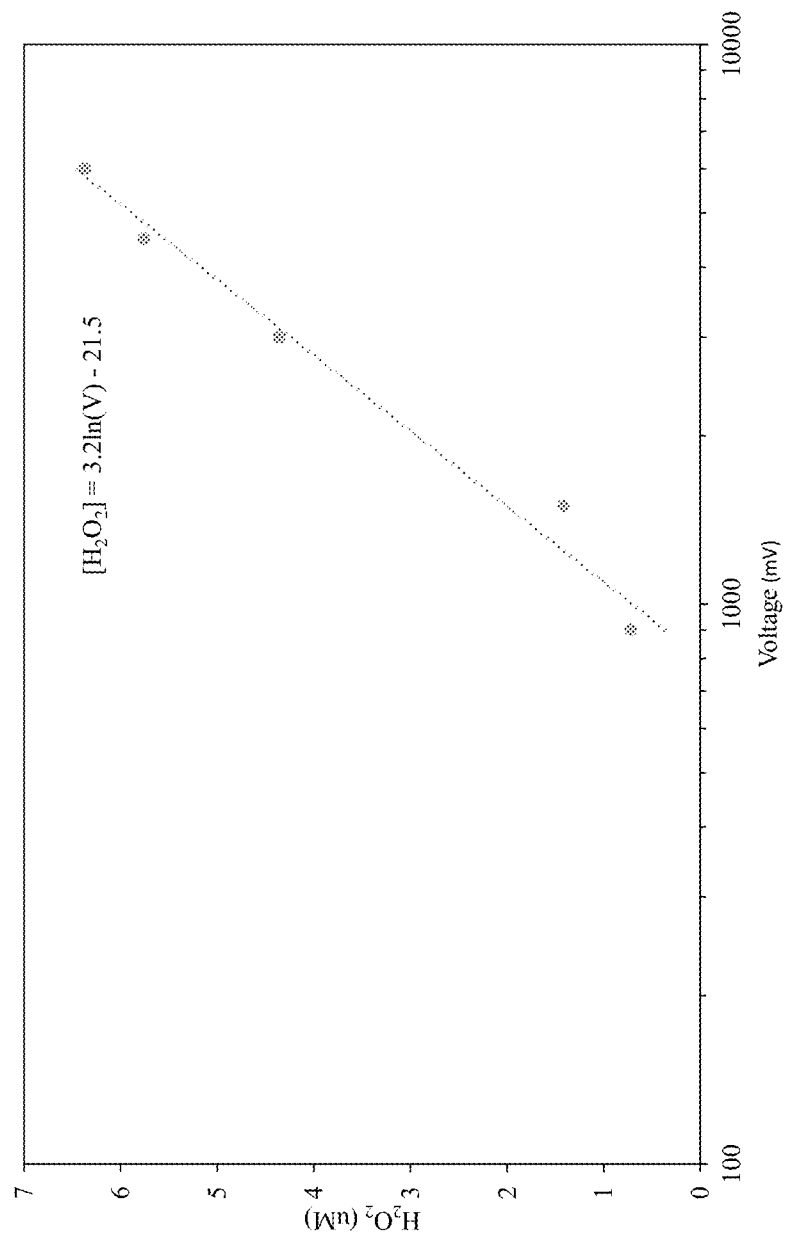

FIG. 15 presents a graph showing hydrogen peroxide formation rate at electrical conditions applied on the tested membranes. The hydrogen peroxide was probed using different voltages 1000 mV to 6000 mV applied after 30 min using modified cuvette.

Figure 16:
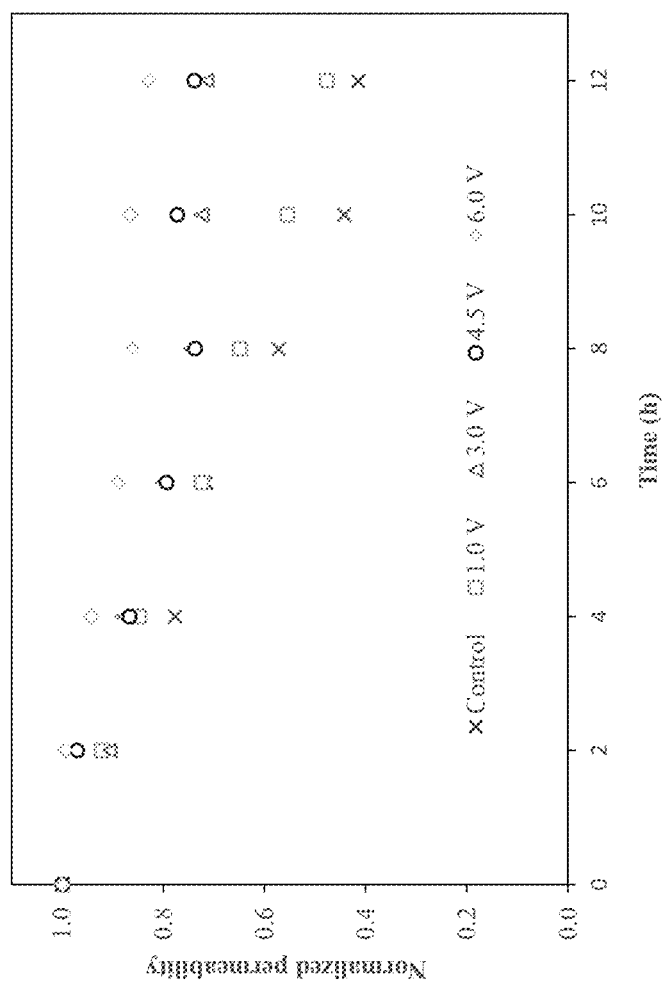

FIG. 16 presents a point graph showing the permeability data of the cross-flow filtration using the membrane under non-growing condition.

FIG. 17 presents a table comparatively summarizing biofouling control between literature and present disclosure.

Figures 18A, 18B, 18C:
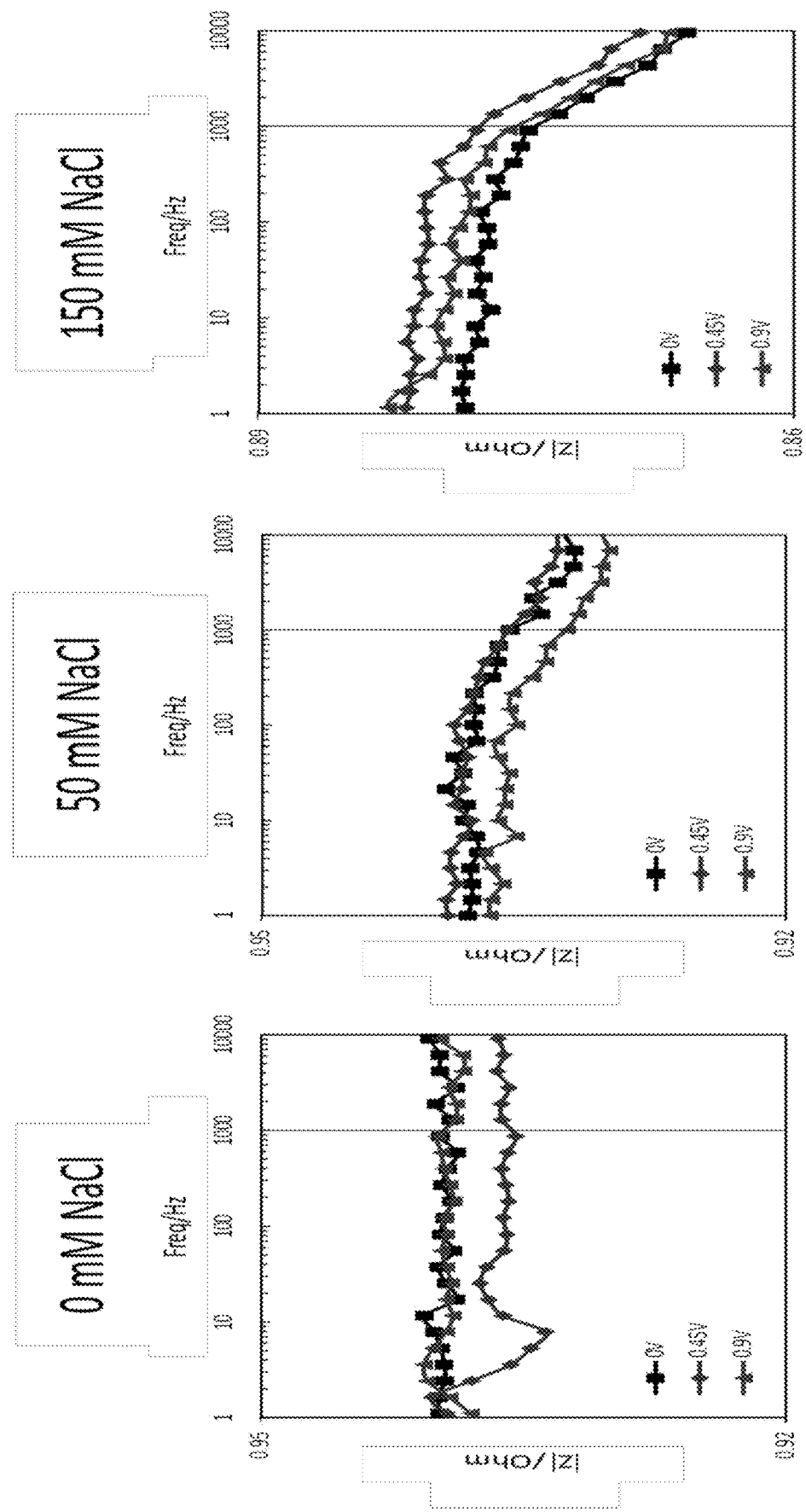
Figure 18F:
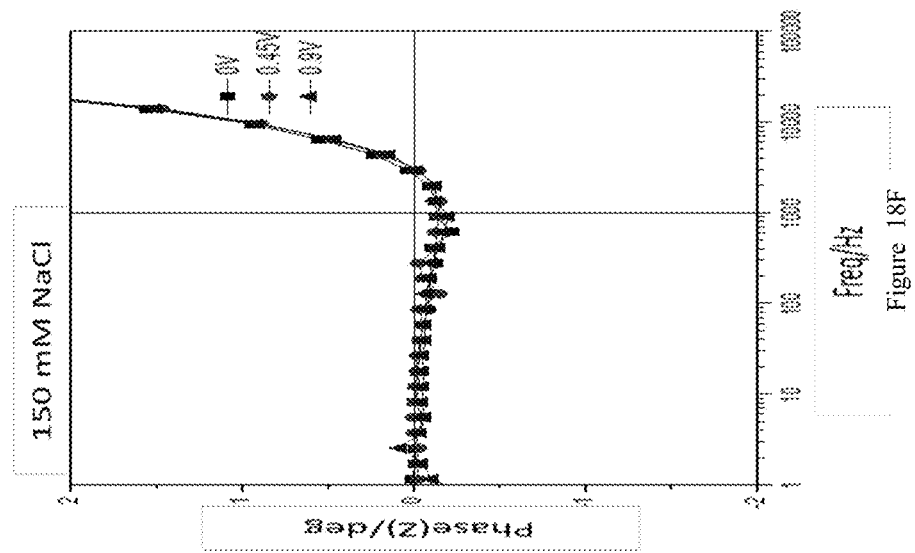
Figure 18E:
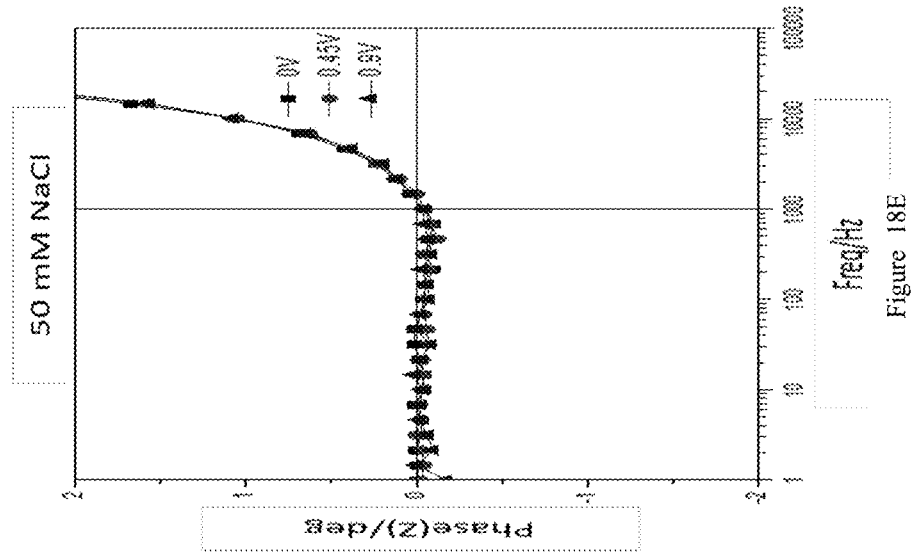
Figure 18D:
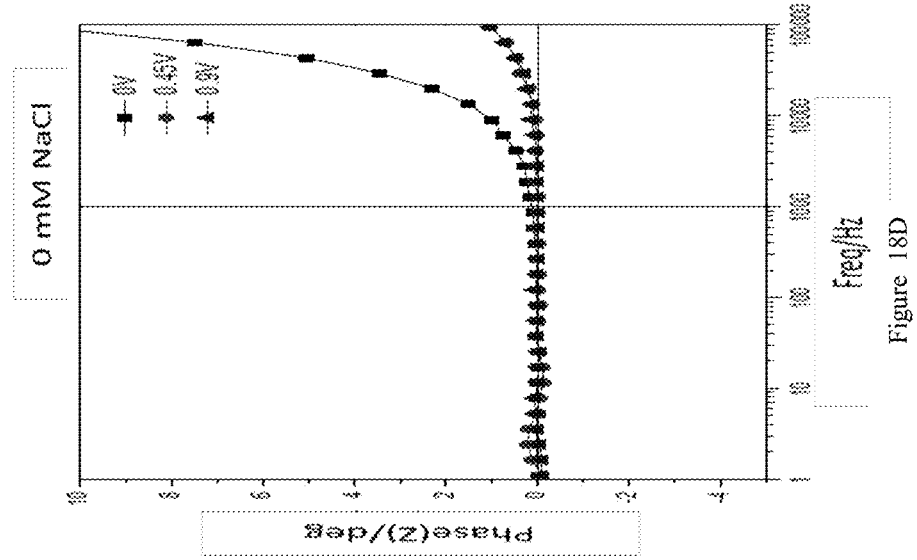
Figure 18L:
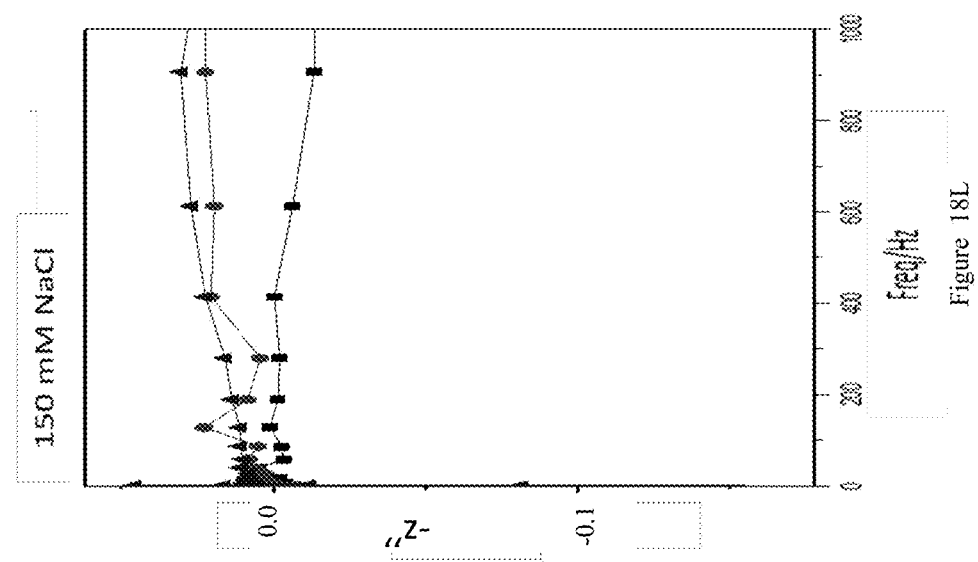
Figure 18K:
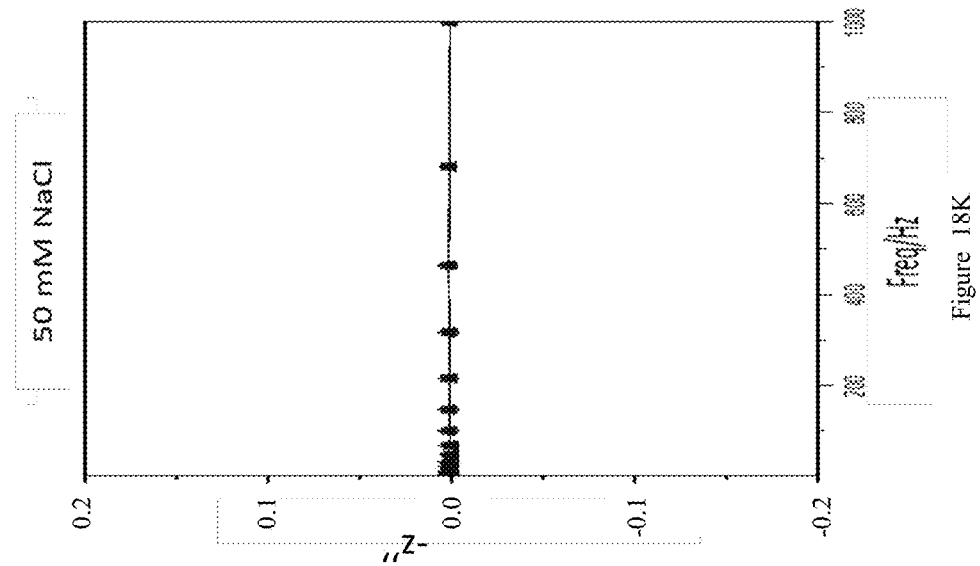
Figure 18J:
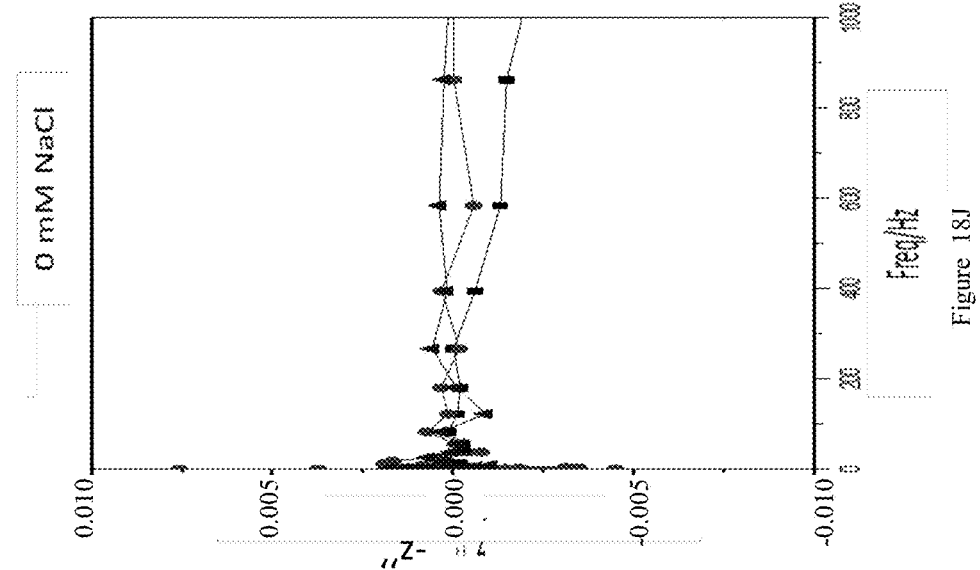

FIGS. 18A-L present plots generated from electrochemical impedance spectroscopy (EIS) analysis of CNT under flow through conditions in resistance mode at different applied anodic potentials 0V, 0.45V, and 0.9V: Bode plot of absolute impedance (|Z|) (FIGS. 18A-C); phase shift versus the applied frequency (FIGS. 18D-F); complex plane impedance (FIGS. 18G-I); (FIGS. 18J-L are respective magnification of FIGS. 18G-I). Run were performed in diluted LB medium supplemented with electrolyte as indicated.

Figures 19A, 19B:
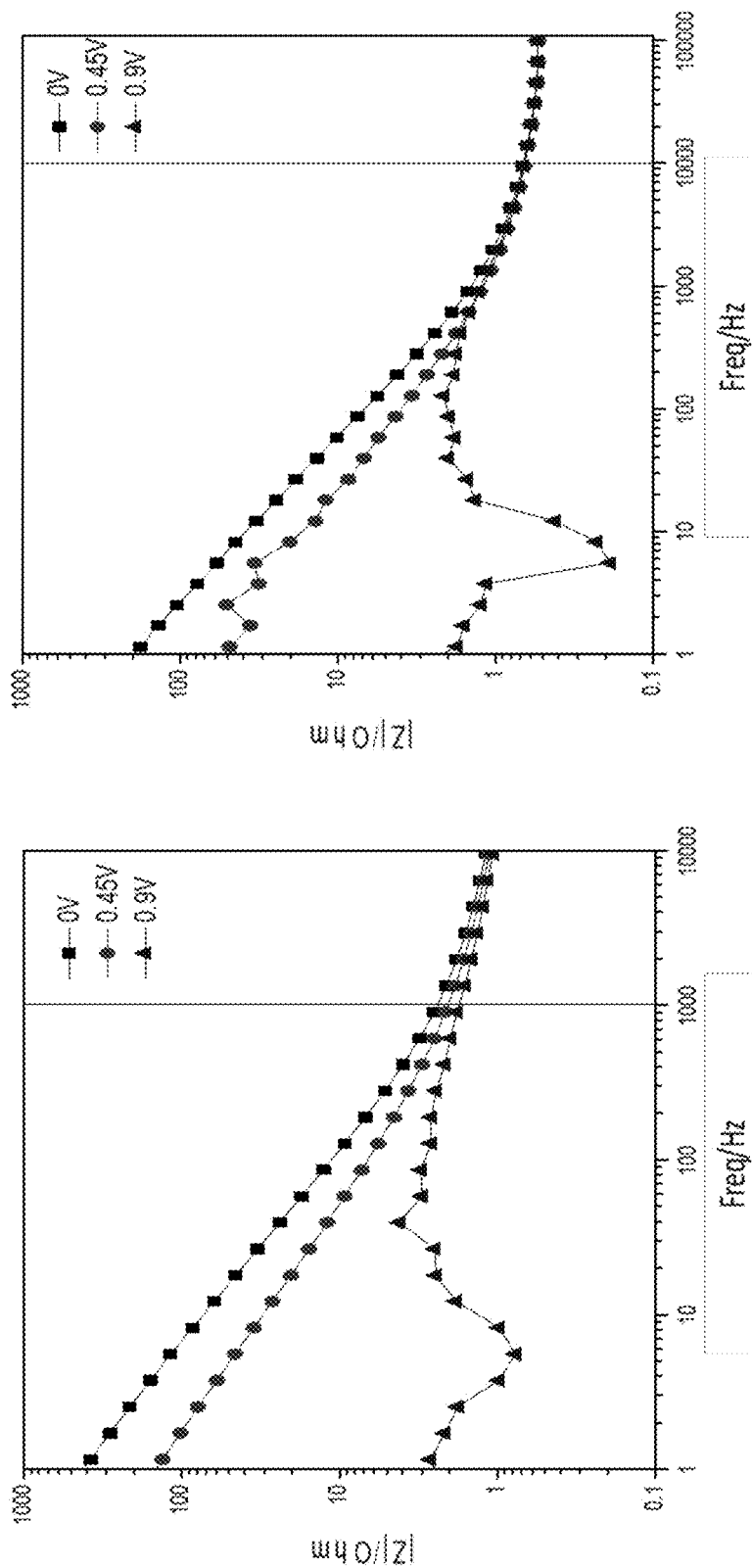
Figure 19D:
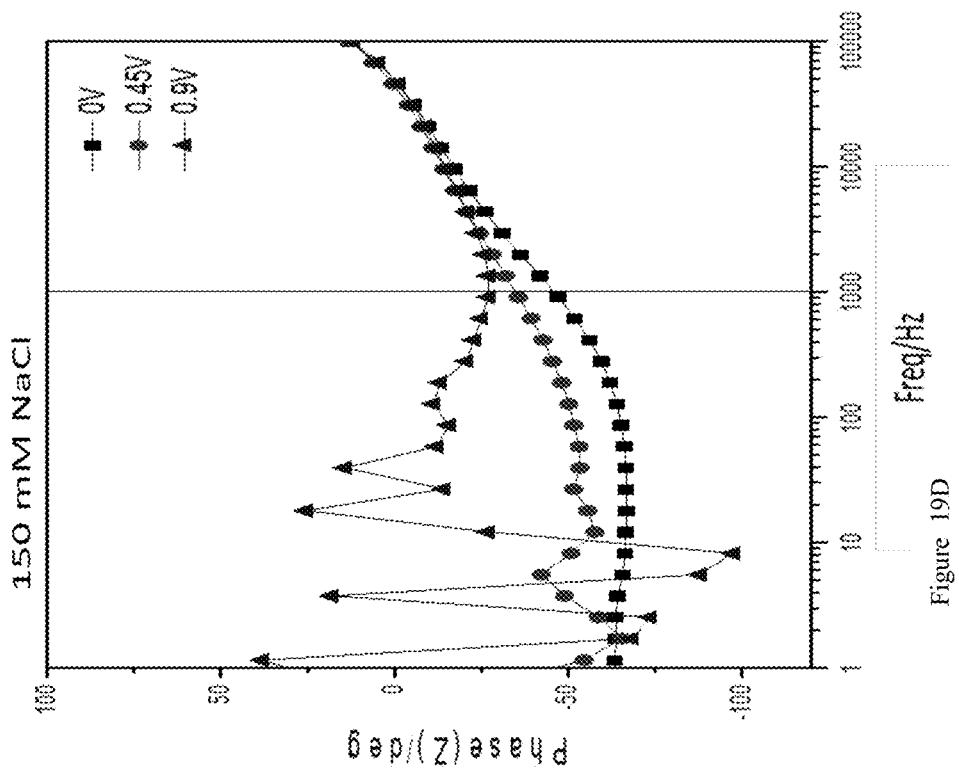
Figure 19C:
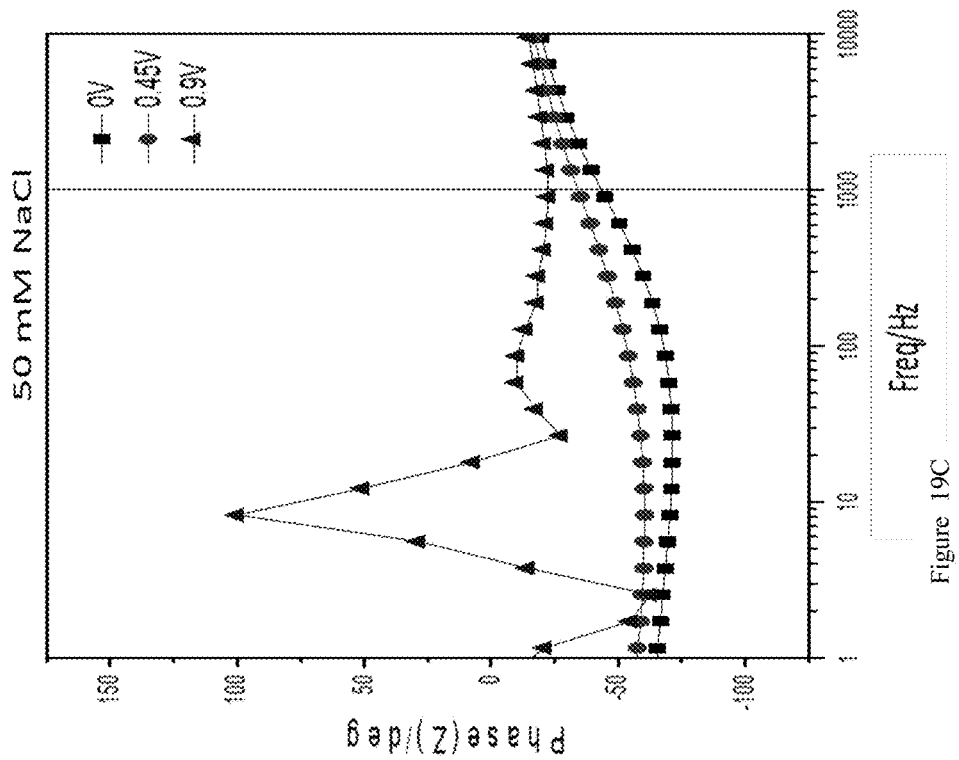
Figure 19E:
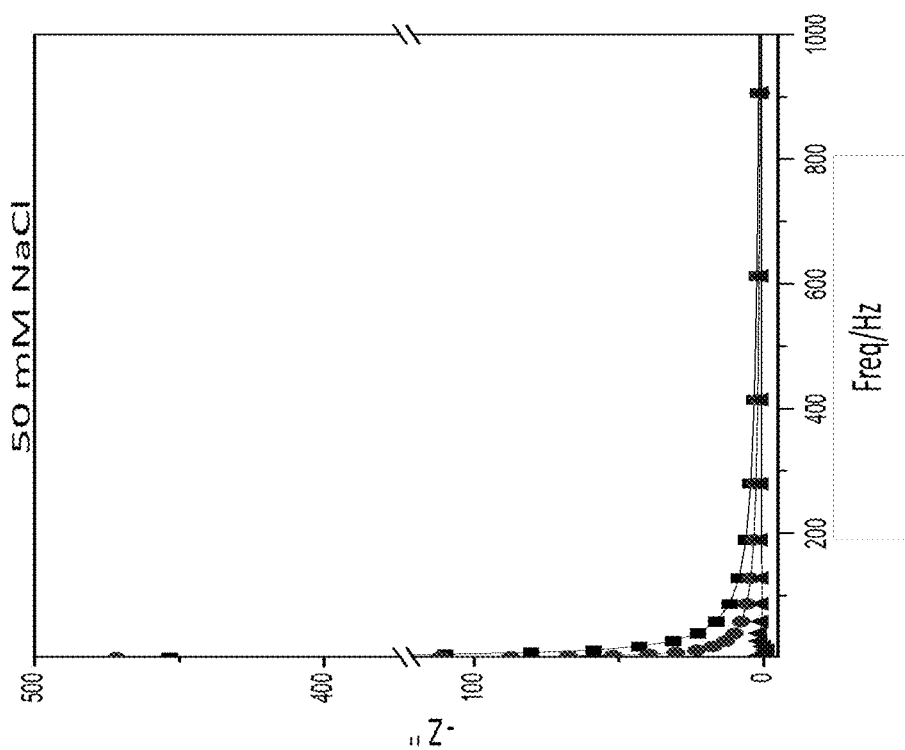
Figure 19F:
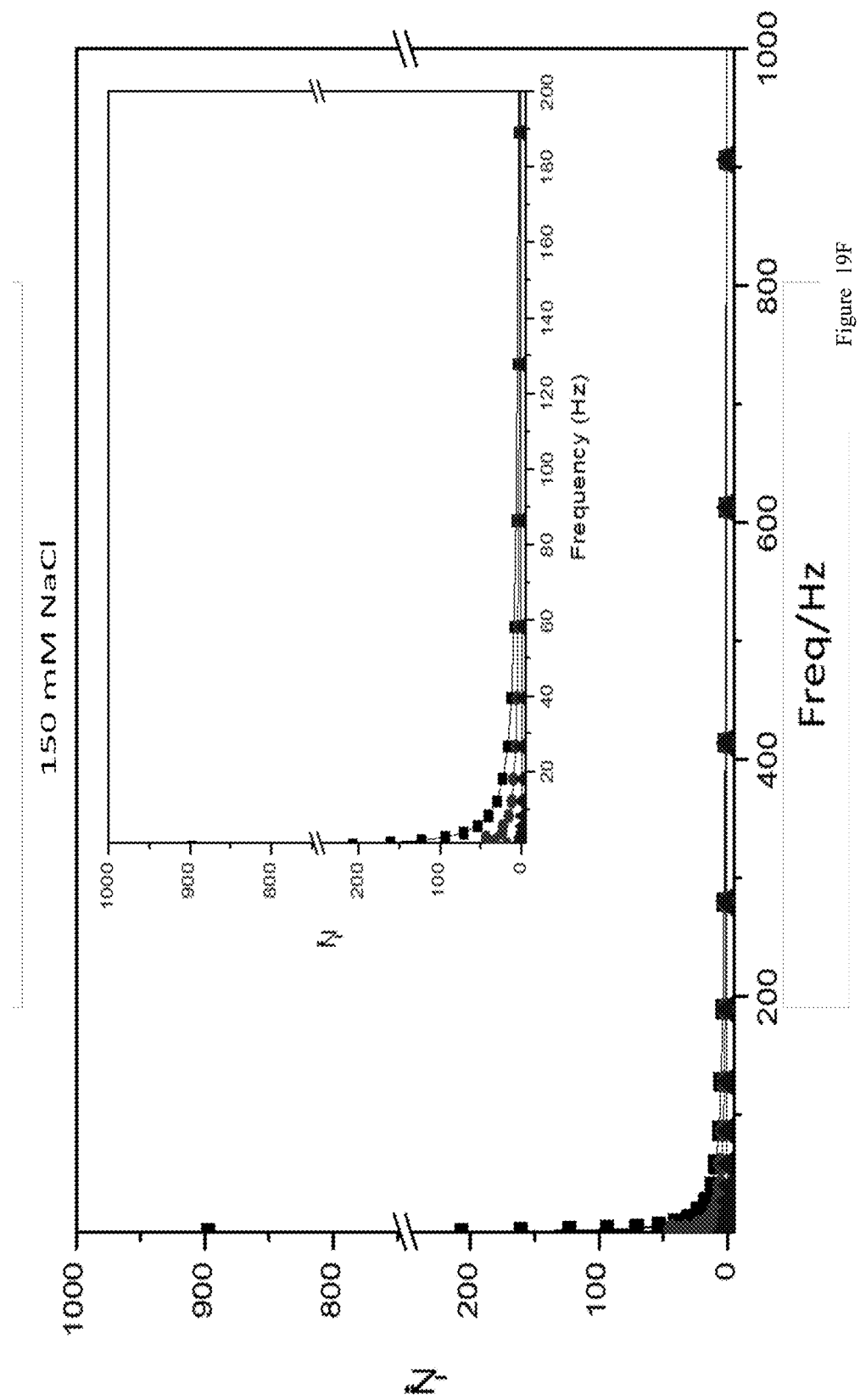

FIG. 19A-F present plots generated from EIS analysis of CNT under flow through conditions in capacitance mode at different applied anodic potentials 0V (black), 0.45V (red) and 0.9V (blue); Bode plot of absolute impedance (|Z|) (FIGS. 19A-B); phase shift versus the applied frequency (FIGS. 19C-D); complex plane impedance (FIGS. 19E-F inset in FIG. 19F shows magnification). Run were performed with NaCl at the indicated concentrations.

Figure 20A:
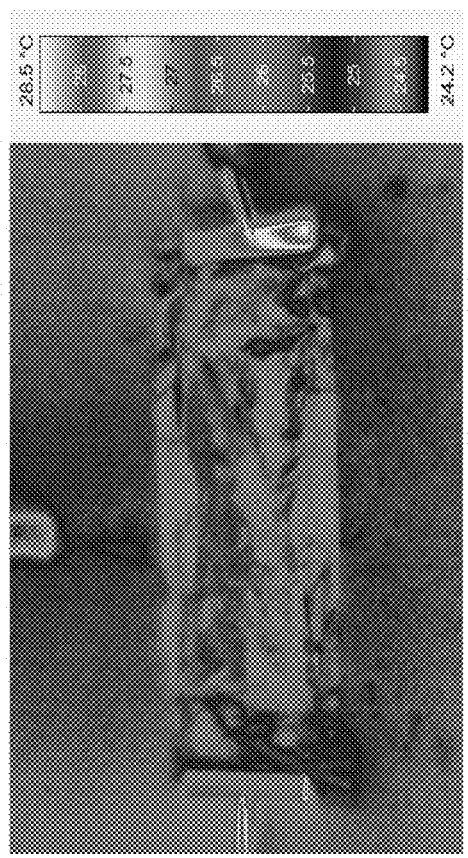
Figure 20B:
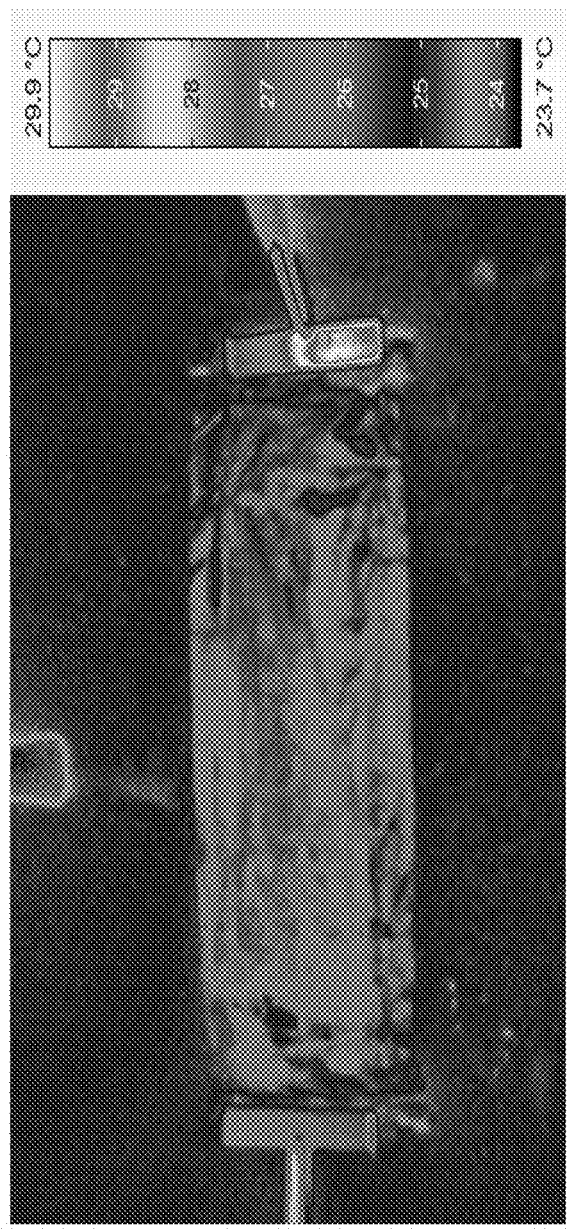
Figure 20C:
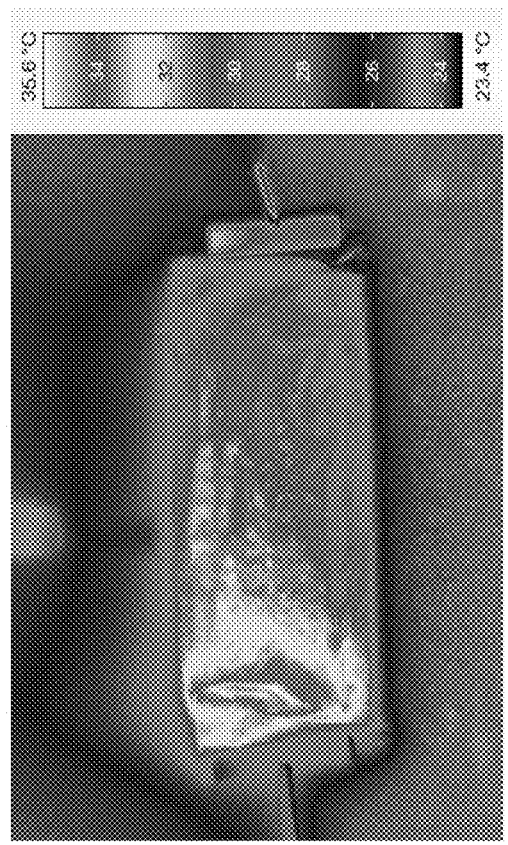
Figure 20D:
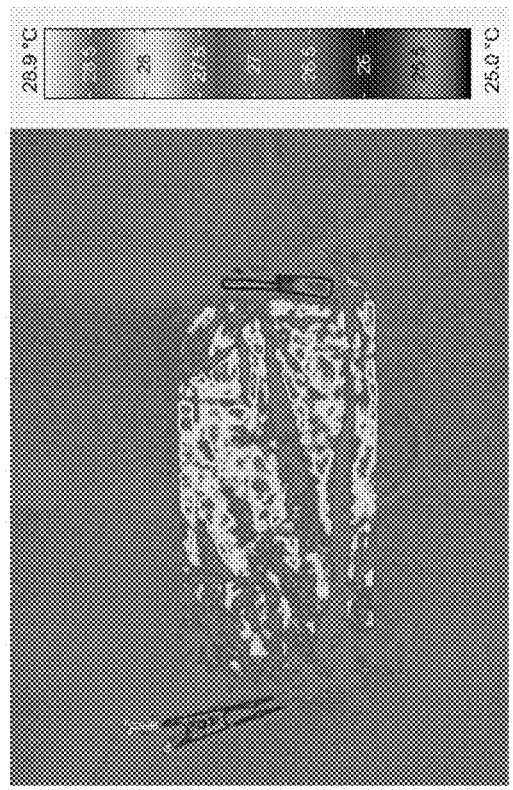
Figure 20E:
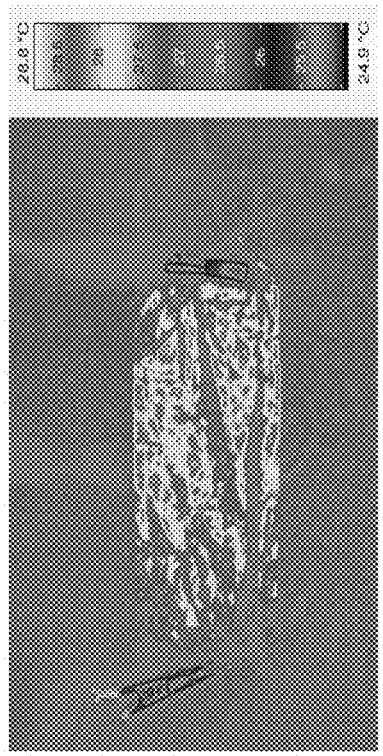
Figure 21:
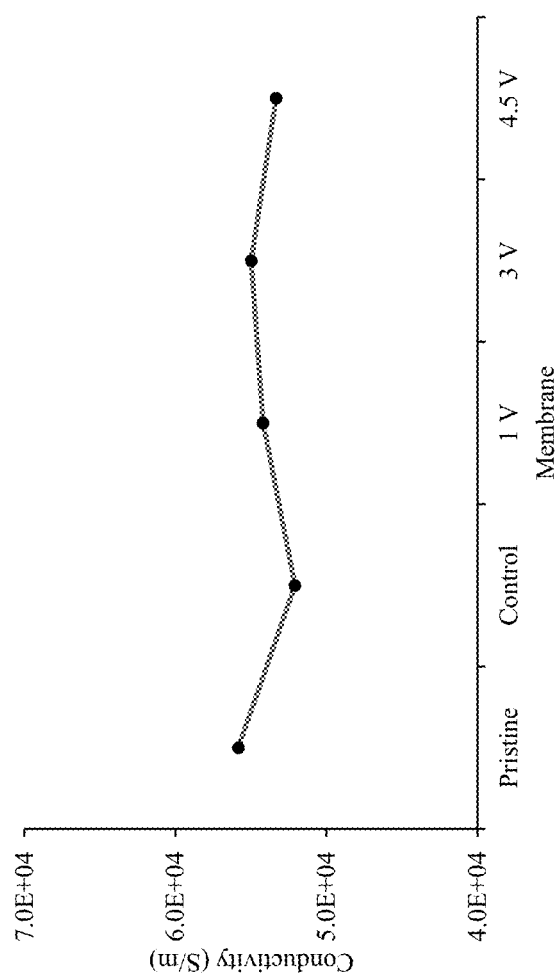

FIGS. 20A-E present thermal infra-red images of the membranes during electric field application: Control (No electricity)(FIG. 20A); AC, 0.9V (No resistor)(FIG. 20B); AC, 3V (No resistor) (FIG. 20C); AC, 0.9 V (100Ω resistor) (FIG. 20D); AC, 3V (100Ω resistor) (FIG. 20E);

FIG. 21 presents a graph showing the electrical conductivity of CNT membranes after 72 hours, connected in resistive mode with external resistor at different AC voltages applied. Pristine, pristine membrane just wetted; Control membrane (no electricity applied) after 72 h.

DETAILED DESCRIPTION

The present invention, in some embodiments thereof, relates to carbon nanotubes laminates (CNM) and use thereof for a self-supporting filtration membrane.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present invention is based, inter alia, on the recognition that a laminate of carbon nanotubes (CNT, plural CNTs) which may be produced according to a certain process may be utilized to perform filtration. In some embodiments, the CNT is adaptable into a self-supporting CNT membrane. In some embodiments, the CNT laminate is characterized by desired intrinsic properties, including, but not limited to, enhanced mechanical strength, chemical stability, thermal stability and high electrical conductivity.

As used herein, the term "chemical stability" is meant to refer to a property of the disclosed CNT membrane which can withstand and function under harsh operating and cleaning conditions, e.g., strong oxidants, bases and acids, high density of microorganisms, or, in the context of thermal stability, high temperatures.

As used herein, the term "carbon nanotube" refers to any of a number of cylindrically-shaped allotropes of carbon of the fullerene family including single-walled carbon nanotubes (SWNTs), double-walled carbon nanotubes (DWNTs), multi-walled carbon nanotubes (MWNTs). CNTs can be capped by a fullerene-like structure or open-ended. CNTs include those that encapsulate other materials. CNTs may be functionalized as well, as described below.

According to an aspect of some embodiments of the present invention, there is provided a composition comprising at least one laminate comprising porous carbon nanotube (CNT), wherein the laminate is characterized by one or more from properties (a) to (f):
(a) comprising pores having a median size of from 15 nm to 150 nm;
(b) a length to thickness ratio that ranges from 500 to 2000;
(c) electrical conductivity of at least $10^3$ S/m;
(d) water permeability coefficient ($L_p$) in the range of 200 to 700 lmh/bar;
(e) tortuosity factor of at least 1.7, and
(f) mechanical strength in the range of from 0.10 to 1.0 GPa.

In some embodiments, the laminate is characterized by two properties from (a) to (f). In some embodiments, the laminate is characterized by three properties from (a) to (f). In some embodiments, the laminate is characterized by four properties from (a) to (f). In some embodiments, the laminate is characterized by five properties from (a) to (f). In some embodiments, the laminate is characterized by properties (a) to (f).

In some embodiments, the laminate is characterized by properties (a) and (b). In some embodiments, the laminate is characterized by properties (a) and (b), and one two, three, or four properties from (c) to (f).

As used herein, the terms "laminate", "laminated sheet", or "laminated film" refer to a sheet material in which one or plurality of kinds of sheets or layers are laminated at a predetermined direction. That is, in some embodiments, a laminate comprises a plurality of CNT layers.

In some embodiments, the term "porous" as used herein refers to a material characterized by porosity, e.g., comprises pores, holes, voids, or space, within its network. However, porous layers may optionally comprise an additional substance in the spaces between the polymeric materials, provided that at least a portion of the volume of the voids is not filled in by the additional sub stance.

The term "porosity" refers to a measure of the void spaces in the material and, in some embodiments, defined as the fraction of the free volume or pore volume of a material relative to the total volume of the material, determined by well-known physical measurements, such as $N_2$ adsorption/desorption.

In some embodiments, the porosity is measured as a fraction, between 0 to 1, or as a percentage between 0 to 100%, i.e. a percentage of the volume of a substance which consists of voids.

In some embodiment, porosity of the CNT is between 0.01 to 0.99.

In some embodiment, porosity of the CNT is 0.01, 0.05, 0.1, 0.2, 0.3, 0.4, 0.5, 0.6, 0.7, 0.8, 0.9, or 0.99, including any value and range therebetween.

In some embodiments, the porosity of the CNT refers to the nanoporous networks within the CNT structure. In some embodiments, the porosity of the CNT refers to the microporous networks.

In some embodiments, the disclosed CNT laminate exhibits uniformity in the range of pore dimensions. In some embodiments, the disclosed CNT laminate exhibits uniform density of CNT material. By "dimensions" (or "size"), it is meant to refer to one or more dimensions (e.g., length, or diameter).

By "uniformity", or any grammatical derivative, thereof it is meant to refer to a variation of less than |±20%|, or, in some embodiments, less than |±10%|.

In some embodiment, the size of the pores is between 5 nm to 300 nm, e.g., 5 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm, including any value or range therebetween. In some embodiments, "the size of the pores" refers to a median value of a plurality of pores in the laminate.

In some embodiments, the term "tortuosity factor" is defined as the ratio of the length of the curved line between two points to the linear distance between the two points.

In some embodiment, the tortuosity factor is related to the porosity of a material. Typically, but not exclusively, the tortuosity factor is at the most $1.3/c$ where c is the porosity.

In some embodiments, the tortuosity factor is e.g., at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, or at least 3.0, at least 3.1, at least 3.2, at least 3.3, at least 3.4, at least 3.5, at least 3.6, at least 3.7, at least 3.8, at least 3.9, or at least 4.0, including any value and range therebetween.

In some embodiments, the tortuosity factor is e.g., less than e.g., 5, less than 4.5, less than 4, less than 3.5, less than 3, less than 2.5, or less than 2.

The term "water permeability" is defined as the volume of water that passes through a laminate or a membrane per unit time, per unit area and per unit of transmembrane pressure.

In some embodiments, the electrical conductivity of the laminate is at least $10^3$ S/m, at least $10^3$ S/m, at least $10^4$ S/m, at least $10^5$ S/m, at least $10^6$ S/m, or in some embodiments, even at least $10^7$ S/m.

In some embodiments, the laminate is characterized by a median length-to-thickness ratio of e.g., 500, 600, 700, 800, 900, 1000, 1100, 1200, 1300, 1400, or 1500, respectively, including any value and range therebetween.

The term "mechanical strength" as used herein means overall and desirable strength such as breaking strength, rigidity, flexibility and/or toughness.

In some embodiments, the disclosed laminate is characterized by a tensile strength of 0.10 GPa or greater, e.g., 0.20 GPa, 0.30 GPa, 0.40 GPa, 0.50 GPa, 0.60 GPa, 0.70 GPa, 0.80 GPa, 0.90 GPa, or 1 GPa, including any value and rage therebetween. In some embodiments, the disclosed laminate is characterized by a tensile strength of from 0.10 GPa to 1 GPa, or 0.5 to 1 GPa. The tensile testing method can be performed by any method known in the art.

In some embodiments, the disclosed laminate is characterized by a thickness of e.g., 5 µm, 10 µm, 20 µm, 30 µm, 40 µm, 50 µm, 60 µm, 70 µm, 80 µm, 90 µm, or even 100 µm, including any value and range therebetween. In some embodiments, the term "thickness" refers to the median value of the shortest distance from one side of the laminate to another side of the laminate. Typically, the thickness is measured in an orthogonal direction.

In some embodiments, the disclosed laminate is characterized by a desired roughness.

The term "roughness" as used herein relates to the irregularities in the surface texture. Irregularities are the peaks and valleys of a surface.

In some embodiments, roughness value is computed by AA (arithmetic average) and RMS (root-mean-square). The AA method uses the absolute values of the deviations in the averaging procedure, whereas the RMS method utilizes the squared values of the deviations in the averaging process.

In some embodiments, the composition of matter is characterized by an RMS roughness of at least 5 nm, at least 10 nm, at least 20 nm, at least 30 nm, at least 40 nm, at least 50 nm, at least 60 nm, at least 70 nm, at least 80 nm, at least 90 nm, or at least 100 nm.

In some embodiments, the surface of the disclosed laminate is characterized by static contact angle measurements.

As used herein, "static contact angle" describes the angle that a liquid substance forms with respect to the substrate's (e.g., laminate's) surface at the place where the free surface of quiescent liquid contacts to the horizontal surface of the laminate.

Typically, but not exclusively, in order to measure the static contact angle, a drop of liquid is formed on the tip of a hypodermic needle attached to a screw syringe. The syringe is fastened to a stand which reduces any irregularities that are produced by manual drop deposition. The substrate is then raised until it touches the drop using the Y control of the stage. The drop is the then brought into the field of view and onto the focal point of the microscope by x-y translation of the stage and image is captured. The static contact angle is calculated by methods known in the art.

The static contact angle of a surface corresponds to a tested liquid.

When a liquid is hydrophilic or amphiphilic, a static contact angle of at least 90° is indicative for superhydrophobicity of a substrate's surface.

When a liquid is hydrophobic or oily, a static contact angle of at least 50° is indicative for oleophobicity of a substrate's surface.

When a liquid is hydrophobic or oily, a static contact angle of at least 90° is indicative for superoleophobicity of a substrate's surface.

As used herein and in the art, a "hydrophilic liquid" is a substance which is liquid at room temperature and which readily interacts with or is dissolved by water and other polar substances.

Exemplary hydrophilic liquids include, but are not limited to, water, aqueous solutions, and any other liquids which are polar and dissolvable in water.

In some embodiments, when the static contact angle is measured for water or other hydrophilic liquids as the liquid, the composition of matter is characterized by a static contact angle of at least 60°, at least 65°, at least 70°, at least 75°, at least 80°, or even at least 90°.

Without being bound by any particular theory and mechanism, the hydrophobic nature of CNT laminates is attributed to the low surface energy of CNT.

In some embodiments, the disclosed laminate exhibits high thermal stability and as such can endure extreme environmental conditions.

In some embodiments, the disclosed laminate exhibits thermal stability up to e.g., at least 300° C., or at least 400° C.

In some embodiments, the disclosed laminate is characterized by a density in the range of from 0.05 g/cm³ to 2 g/cm³. In some embodiments, the disclosed laminate is characterized by a density in the range of from 0.1 g/cm³ to 1 g/cm³. In some embodiments, the disclosed laminate is characterized by a density in the range of from 0.2 g/cm³ to 0.8 g/cm³.

In some embodiments, the disclosed laminate is characterized by a density of 0.05 g/cm³, 0.1 g/cm³, 0.2 g/cm³, 0.3 g/cm³, 0.4 g/cm³, 0.5 g/cm³, 0.6 g/cm³, 0.7 g/cm³, 0.8 g/cm³, 0.9 g/cm³, 1 g/cm³, 1.1 g/cm³, 1.2 g/cm³, 1.3 g/cm³, 1.4 g/cm³, 1.5 g/cm³, 1.6 g/cm³, 1.7 g/cm³, 1.8 g/cm³, 1.9 g/cm³, or 2 g/cm³, including any value and range therebetween.

In some embodiments, the disclosed CNT is functionalized, e.g., has attached on at least one surface thereof one or more chemical functional group, that is, the CNT has bare one or more functionalizing moiety which is associated with the CNT external carbon surface.

As used herein, the term "functionalized," when used in reference to CNTs, refers to CNTs that have been subjected to a post-CNT synthesis reaction that results in the presence of a covalently-linked organic functional group. Examples of such functional groups include, without limitation, carboxylic acids, amines, alcohols, amides, esters, halogens, such as fluorine, bromine, iodine, chlorine, sulfides, sulfates, and the like.

In some embodiments, the disclosed CNT is oxidized to afford oxygen-containing groups such as, without being limited thereto, carboxyl and hydroxyl groups. The oxidation of CNTs may be achieved by any method known in the art, e.g., wet chemical methods, photo-oxidation, oxygen plasma or gas phase treatment, as known in the art.

Articles:

According to an aspect of some embodiments of the present invention there is provided an article which comprises a composition and/or the laminate(s) as described herein.

In some embodiments, the article (e.g., a filtration membrane as described herein throughout) is characterized by one or more from properties (a) to (f) described hereinabove.

In some embodiments, there is provided an article which comprises one or more laminates comprising or made of porous CNT. In some embodiments, the surface of the laminate is characterized by roughness, conductivity, water permeability coefficient, porosity, pore sizes, tortuosity factor, length to thickness ratio, and/or static liquid contact angle as described for the composition or for the laminate herein throughout.

Any article that may benefit from the compositions described herein is contemplated.

Exemplary articles include, but are not limited to, agricultural device, containers, agricultural devices, construction elements, water treatment devices and elements thereof, organic waste treatment devices and elements thereof, microelectronic devices, microelectromechanical devices, a photovoltaic devices, or microfluidic devices.

In some embodiments, the article is a filtration membrane.

In some embodiments, the article is a self-supporting membrane as defined herein throughout, for the selective separation of chemical species, in particular for the selective separation of species contained in liquid mixture in natural or industry.

Thus according to an aspect of the present disclosure, there is provided a use of a self-supporting CNM based on the intrinsic properties of a CNT laminate, e.g., with enhanced mechanical strength, chemical stability, thermal stability and high electrical conductivity as a filtration membrane, e.g., a microporous membrane in aqueous and non-aqueous media or emulsions.

As described in the Examples section below, the conductivity property of the disclosed laminate may allow anti-biofouling activity of the disclosed membrane.

In some embodiments, CNT laminates as synthesized are used as self-supporting microfiltration or ultrafiltration carbon nanotube membrane.

In some embodiments, CNT laminates are adapted (or modified) into a self-supporting microfiltration or ultrafiltration carbon nanotube membrane.

In some embodiments, in order to control filtration performance, i.e., permeability and selectivity, CNT laminate(s) may be modified either during fabrication, or, in some embodiments, as a post-fabrication step by physically adapting the CNT laminates into a self-supporting filtration carbon nanotube membrane.

For example, the modification step may comprise cutting, shaping, laying, flattening, stretching, unrolling, aligning, combing, heating, vibrating, or reinforcing the CNT laminate(s).

In some embodiments, the laminate is adapted into a self-supporting filtration carbon nanotube membrane, for example, and without limitation, by densifying the laminate of carbon nanotubes, as described e.g., in the Examples section below.

In exemplary embodiments, densifying the laminate of carbon nanotubes is by a factor in the range 1.5 to 2.5. In some embodiments, the laminates may be reinforced with a mechanical porous support in a composite matrix, as feasible.

In some embodiments, the laminate is chemically densified and adapted into a self-supporting filtration carbon nanotube membrane.

In some embodiments, the laminate is chemically densified in an organic liquid. A non-limiting organic liquid is a polar solvent, such as acetone or methanol. Densification is typically followed by air-drying.

In some embodiment, the CNT laminates are mechanically stretched, thereby allowing densifying and aligning the fibers of the laminate of carbon nanotubes.

Since the separation mechanism of CNM involve both molecular sieving and tortuosity, densification and alignment of the fiber may be used to manipulate selectivity so as to promote separation in the desired range (loose or tight ultrafiltration) while keeping the advantage of very high permeation rates.

As demonstrated in the Examples section below, the microporous-like filtration carbon nanotube membrane exhibits improved selectivity up to the range of tight ultrafiltration.

As described herein, in some embodiment, the microporous carbon nanotube membrane is substantially homogeneous without the need of mechanical support.

In some embodiments, the disclosed membrane allows separating out a chemical species, which comprises a liquid mixture containing the species that it is desired to separate out through a self-supporting membrane in accordance with the invention and as described herein. As used herein, the term "self-supporting" means that the membrane can hold a definable shape in the x-, y-, and z-plane in the absence of any applied force or in the absence of any supporting substrate or polymer.

That is, in some embodiments, the disclosed membrane is devoid of supporting substrate or polymer.

In some embodiments, the membrane may withstand some level of applied pressure or force as described below.

In some embodiments, the term "filtration membrane" as used herein throughout refers to a membrane characterized by their molecular weight cut-off and/or their retention values for inorganic salts and/or small organic molecules.

As demonstrated in the Examples section, the disclosed membrane may display high water permeability, even without applied pressure (e.g., percolation).

In some embodiments, the molecular weight cut-off is at least 150 kDa, at least 160 kDa, at least 170 kDa, at least 180 kDa, at least 190 kDa, or at least 200 kDa.

In some embodiments, the disclosed porous membrane is a microfiltration or ultrafiltration membrane. In some embodiments, membrane permeability is given in units of LMH/bar (=LMH/100 kPa; also referred to as "L/m$^2$h per bar"), which is familiar to those skilled in the art, and represents the flux of pure water through the membrane in terms of the number of liters (L) per square meter (M) of membrane per hour (H) at 1 bar driving pressure (bar). As further described in the Examples section below, the unique morphology of the disclosed laminate (e.g., the porous structure) may facilitate high permeation rates of the membrane.

In some embodiments, by "high permeation rate" it is meant to refer to permeation rate of at least 150 to at least 350 L/m$^2$h per bar applied, for example, at least 150 L/m$^2$h per bar applied, at least 200 L/m$^2$h per bar applied, at least 250 L/m$^2$h per bar applied, at least 300 L/m$^2$h per bar applied, or at least 350 L/m$^2$h per bar applied.

In some embodiments, the filtration membrane is characterized by electrical conductivity that varies within less than |±10%| along the length of the membrane. In some embodiments, the electrical conductivity varies within less than |±5%| along the length of the membrane.

In some embodiments, the filtration membrane is characterized by absolute pore rating of below 100 nm, below 90 nm, below 80 nm, below 70 nm, below 60 nm, below 50 nm, or even below 40 nm.

In some embodiments, an "absolute pore size rating" specifies the pore size at which a challenge organism of a particular size will be retained with at least 85% efficiency, or, in some embodiments at least 95% efficiency under defined test conditions e.g., test organism (or particle size), challenge pressure, concentration and detection method.

In some embodiments, an "absolute pore size rating" is as defined in the Examples section below.

In some embodiments, the thickness of the microporous CNT membrane is in the range of from 5 to 200 micrometers, or from 20 to 100 micrometers, or from 45 to 65 micrometers.

Systems

In some embodiment, there is provided a system comprising the disclosed article (e.g., membrane) in an embodiment thereof.

Exemplary systems include, without being limited thereto, bioreactor, either aerobic or anaerobic and filtration systems e.g., for separation or monitoring during water filtration or separation.

In some embodiment, the control unit configured to induce an electrical current along a length of the membrane, as described e.g., in the Examples section that follows.

In some embodiment, by "electrical current" it is meant to refer to alternating current (AC).

In some embodiment, by "electrical current" it is meant to refer to direct current (DC). In some embodiment, the electrical current is affected under electric potential implemented of e.g., 100 mV, 200 mV, 300 mV, 500 mV, 600 mV, 700 mV, 800 mV, 900 mV, 1000 mV, 1100 mV, 1200 mV, 1300 mV, 1400 mV, 1500 mV, 1600 mV, 1700 mV, 1800 mV, 1900 mV, 200 mV, 2100 mV, 2200 mV, 2300 mV, 2400 mV, 2500 mV, 2600 mV, 2700 mV, 2800 mV, 2900 mV, 3000 mV, 3100 mV, 3200 mV, 3300 mV, 3400 mV, 3500 mV, 3600 mV, 3700 mV, 3800 mV, 3900 mV, 4000 mV, 4100 mV, 4200 mV, 4300 mV, 4500 mV, 4600 mV, 4700 mV, 4800 mV, 4900 mV, 5000 mV, 5100 mV, 5200 mV, 5300 mV, 5400 mV, 5500 mV, 5600 mV, 5700 mV, 5800 mV, 5900 mV, 6000 mV, 6100 mV, 6200 mV, 6300 mV, 6400 mV, 6500 mV, 6600 mV, 6700 mV, 6800 mV, 6900 mV, 7000 mV, 7100 mV, 7200 mV, 7300 mV, 7400 mV, 7500 mV, 7600 mV, 7700 mV, 7800 mV, 7900 mV, 8000 mV, 8100 mV, 8200 mV, 8300 mV, 8400 mV, 8500 mV, 8600 mV, 8700 mV, 8800 mV, 8900 mV, 9000 mV, 9100 mV, 9200 mV, 9300 mV, 9400 mV, 9500 mV, 9600 mV, 9700 mV, 9800 mV, 9900 mV, or even 10000 mV, including any value and range there between.

In some embodiment, the electrical current is affected under electric potential implemented of at least 500 mV, 1000 mV, or at least 2000 mV.

In some embodiments, the frequency of the alternating current (AC) is in the range of 1 Hz to 10 kHz. In some embodiments, the frequency of AC is in the range of 1 Hz to 1 kHz. In some embodiments, the frequency of the AC is in the range of 1 Hz to 20 Hz. In some embodiments, the frequency of the AC is in the range of 1 Hz to 10 Hz. In some embodiments, the frequency of the AC is 1 Hz, 2 Hz, 3 Hz, 4 Hz, 5 Hz, 6 Hz, 7 Hz, 8 Hz, 9 Hz, 10 Hz, 11 Hz, 12 Hz, 13 Hz, 14 Hz, 15 Hz, 16 Hz, 17 Hz, 18 Hz, 19 Hz, or 20 Hz, including any value and range therebetween.

In some embodiments, the ranges of the frequency described above provide a superior performance of antibiofilm activity.

In some embodiments, the electric current is applied in a capacitive mode. In some embodiments, the electric current is accomplished through driving electrodes, with either or not external resistance or, alternatively, may be accomplished through capacitive charging (e.g., on its surface).

In some embodiment, the system comprises a control unit. In some embodiment, the control unit is configured to induce an electrical current along a length of the membrane.

In some embodiments, the length is a distance measured from the distal edges of the membrane.

FIGS. 9A-C present a schematic diagram of a membrane cell design (FIG. 9A), electric circuit along the membrane (resistive mode) design (FIG. 9B), and electric circuit across the membrane (capacitive mode) design (FIG. 9C).

Reference is made to FIG. 9B presenting a schematic diagram of a membrane cell design 100 which allows to provide electric circuit along the membrane (resistive mode).

Membrane cell 100 may have housing 105.

Housing 105 may have two part e.g., cell top 115 and cell bottom 117.

Housing 105 may have a liquid (e.g., water) inlet inner port (also referred to as "feed") 110. Liquid inlet port 110 may include a pipe of various shapes and sizes, connected to, attached to or integrally formed with the housing 105. Liquid inlet port 110 may allow unfiltered water to enter housing 105.

The term "port" as used herein throughout, may refer to a path for distributing liquid or gas, either on or above ground surface or underground. The pipe may include, without being limited thereto, a channels, a tube, a trough or other means for distribution. As used herein, the pipe may be adjacent or abutting to housing 105. The Pipe may be a funnel.

Housing 105 may have a first liquid outlet port 120 disposed in cell top 115. Housing 105 may have a second liquid outlet port 125 disposed in cell bottom 117. Liquid outlet ports 120 or 125 may be a pipe. Liquid outlet port 125 may be an opening of various shapes and sizes in housing 110. Ports 120 or 125 may be configured as a siphon.

Optionally, membrane cell 100 may be used in a filtration process in which suspended solids and solutes of high molecular weight are retained or exit via port 120 in the so-called "retentate", while water and low molecular weight solutes pass through the membrane in the permeate (filtrate) via port 125.

Housing 105 may have a CNT membrane 130 deposited therein. Embodiments of membrane 130 are described herein throughout.

Housing 105 may have a first electrode 135. First electrode 135 may be disposed on cell top 115, optionally, via an O-ring. Housing 105 may have a second electrode 150A. Housing 105 may have a third electrode 150B.

In a first exemplary configuration ("resistive mode"; FIG. 9B) second electrode 150A may allow to provide an electric circuit along membrane 130 e.g., via connecting an electric circuit between second electrode 150A to third electrode 150B. The electric circuit may contain a resistor 155.

Membrane cell 100 may have attached a function generator 160. Function generator 160 may have an amplifier.

Optionally, function generator 160 generates a signal power from an AC signal source, e.g., by using an auxiliary oscillator, providing a function whose amplitude and frequency are controlled.

Optionally, function generator 160 generates a function, constituting an output signal from an input signal Reference is further made to FIG. 9C showing a second exemplary configuration ("capacitive mode") of membrane cell 100 in which an electrical potential is applied between the first electrode 135 and third electrode 150B to provide an electric field across membrane 130.

The terms "top", "bottom", "over", "under" and the like are used for descriptive purposes and not necessarily for describing relative positions.

Membrane cell 100 may have a control unit 170.

The term "control unit" may refer to a computerized controller that is connected to various elements of the disclosed article (e.g., the filtration membrane), e.g., function generator 160.

Optionally, the "control unit" refers to a computerized controller that is connected to various elements of the article (e.g., the filtration membrane) either by wire or wirelessly, to transmit operating instructions to these elements and to receive feedback, as confirmation of instructions, sensor measurements, etc., from elements of the article.

Control unit 170 may allow switching from the first exemplary configuration to the second exemplary configuration, and vice versa.

Optionally, the disclosed system further comprises a computer program product.

Optionally, the computer program product comprises a computer-readable storage medium. The computer-readable storage medium may have program code embodied therewith. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified herein. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified herein throughout.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the drawings.

In one embodiment of the invention, there is provided a method for reducing the concentration of a contaminant in a fluid, comprising the step of contacting the fluid with the disclosed article (e.g., filtration membrane). In some embodiments the method allows to provide less environmentally deleterious or more environmentally acceptable aqueous-based materials, preferably in high yields.

The disclosed method is effective for treating one or more contaminant components, e.g., organic-based components, such as hydrocarbons, and/or organic-based components. Examples of organic-based and hydrocarbon-based contaminant components which may be processed in accordance with the present invention include, but are not limited to, petroleums (crude oils including topped crude oils), organic acids such as benzoic acid, ketones, aldehydes, aromatic components including phenols and the like, organic materials containing hetero atoms such as nitrogen, sulfur and halogen, e.g., chloride, and the like, dyes, polymeric materials, including, without limitation polymericcarbohydrate (e.g., polysaccharides), proteins, fatty acids and mixtures thereof. Other contaminants which may be treated in the present process include, for example, and without limitation, materials which are active components in or products of a manufacturing process, such as cyanide or hydrazine, or a process by-product, organic insecticides, herbicides, sewage contamination, and pesticides resulting from soil leaching due to continuous water usage in agriculture, e.g., the production of fruits and vegetables particularly in arid to semi-arid climates.

Anti-Biofilm Formation (ABF) Activity:

While studying the activity of the disclosed membrane as described herein, the present inventors have surprisingly uncovered that membrane exhibits high antifouling activity and can therefore be beneficially incorporated in filtration systems in which such an activity is desired.

Herein "anti-biofouling activity" or "antifouling activity" is referred to as an ability to inhibit (prevent), reduce or retard biofilm formation of an article's surface.

The term "biofilm", as used herein, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides.

In the context of the present embodiments, the living cells forming a biofilm can be cells of a unicellular microorganism (prokaryotes, archaea, bacteria, eukaryotes, protists, fungi, algae, euglena, protozoan, dinoflagellates, apicomplexa, trypanosomes, amoebae and the likes), or cells of multicellular organisms in which case the biofilm can be regarded as a colony of cells (like in the case of the unicellular organisms) or as a lower form of a tissue.

In the context of the present embodiments, the cells are of microorganism origins, and the biofilm is a biofilm of microorganisms, such as bacteria and fungi. The cells of a microorganism growing in a biofilm are physiologically distinct from cells in the "planktonic form" of the same organism, which by contrast, are single-cells that may float or swim in a liquid medium. Biofilms can go through several life-cycle steps which include initial attachment, irreversible attachment, one or more maturation stages, and dispersion. The phrase "anti-biofilm formation activity" refers to the capacity of a substance to affect the prevention of formation of a biofilm of bacterial, fungal and/or other cells, and/or to affect a reduction in the rate of buildup of a biofilm of bacterial, fungal and/or other cells, on a surface of a substrate.

In some embodiments, the biofilm comprises bacterial cells. In some embodiments, the bacterial cells are of bacteria selected from the group consisting of: all Gram-positive and Gram-negative bacteria.

In some embodiments, the Gram-negative biofilm-forming bacteria may be selected from the group of species such as, but not limited to, *Proteus, Enterobacter, Citrobacter, Shigella, Escherichia, Edwardsiella, Aeromonas, Plesiomonas, Moraxella, Alcaligenes*, and *Pseudomonas*.

In exemplary embodiments, a biofilm is formed of *Pseudomonas putida* bacterial cells.

As demonstrated hereinbelow, a membrane as described herein was shown to exhibit antibiofilm activity and can thus prevent, retard or reduce the formation or the mass of a biofilm. Therefore, CNT membrane as described herein can be efficiently incorporated within filtration systems containing same in which anti-biofilm formation activity is beneficial (e.g., is required or desired).

According to some embodiments of the present invention, the activity of preventing or reducing the formation of a biofilm on an article (e.g., filtration membrane, for example, on a surface thereof), may be achieved by applying electrical current in/on at least portion of the article. Embodiments of the electrical current are described hereinabove.

As used herein, the term "preventing" in the context of the formation of a biofilm, indicates that the formation of a biofilm is essentially nullified or is reduced by at least 20%, at least 30%, at least 40%, at least 50%, at least 60%, at least 70%, at least 80%, or at least 90%, including any value and range therebetween, of the appearance of the biofilm in a comparable situation lacking the presence of the disclosed membrane.

Alternatively, preventing means a reduction to at least e.g., 15%, 10%, or 5% of the appearance of the biofilm in a comparable situation lacking the presence of the disclosed membrane. Methods for determining a level of appearance of a biofilm are known in the art.

In some embodiments, inhibiting, reducing and/or retarding a formation of a biofilm as described herein is reflected by reducing biofilm formation on the article (e.g., filtration membrane) by at least 20%, at least 30%, at least 40%, at least 50%, at least 60%, at least 70%, at least 80%, or at least 90%, including any value therebetween, compared e.g., to the same filtration membrane without applying thereon the electrical current.

In some embodiments, an amount of biofilm formed on an article (e.g., filtration membrane) or a filtration system containing same with bacterial cells in the presence of a growth medium for 24 hours is lower than $10^5$ CFU. In some embodiments, it is lower than $10^4$ CFU, lower than $10^3$ CFU, lower than $10^2$ CFU or even lower.

Further according to as aspect of some embodiments of the present invention there is provided a method of inhibiting, reducing and/or retarding a formation of a biofilm in on an article (e.g., filtration membrane) or a filtration system containing same, which is affected by applying electrical current in/on at least portion of the article.

In some embodiments, articles in which prevention of biofilm formation are of high importance are usable in the context of these embodiments of the present invention.

As described herein throughout, such articles of manufacturing include, but are not limited to, processing devices, medical devices, packages and containers, agricultural devices, construction elements, water treatment systems and elements thereof, and organic waste treatment systems and elements thereof.

According to some embodiments of the present invention, the composition presented herein is packaged in a packaging material and identified in print, in or on the packaging material, for use in reducing or preventing the formation of a biofilm and/or disrupting a biofilm in or on a substrate.

In some embodiments, the disclosed CNT membrane (e.g., microporous CNT membrane) is sterilized and used for aseptic applications.

Alternatively, the disclosed CNM herein can be incorporated within any of the articles of manufacturing described herein, during manufacture of the article of manufacturing.

According to an aspect of some embodiments of the present invention, there is provided a composition of matter as described herein, which is identified for use in manufacturing an article containing the CNT laminate.

In some embodiments, such a composition is identified for use in manufacturing articles of manufacture which are characterized as capable of reducing, inhibiting and/or retarding biofilm formation, as described herein.

General:

As used herein the terms "about" or "approximately" refer to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Example 1

Preparation of CNT Laminates

CNT laminates for the procedures below were supplied by Tortech Nano Fibers (TNF). In exemplary procedures, fibers and ribbons of carbon nanotubes were fabricated using direct spinning from the chemical vapor deposition synthesis zone of a furnace using a liquid source of carbon and an iron nano-catalyst. The alignment of the nanotubes and the thickness of the coatings were controlled by the rotation speed and coating time. Different batches of fibers were fabricated by changing the flow rate of iron catalyst. A list of the laminates tested is presented in Table 1 showing CNT membranes tested and their pore rating based on calculation and their pore rating based on calculation.

TABLE 1

| Membrane | Thickness (μm) | Average Permeability@20° C. (LMH/bar)[a] | Nominal pore rating (nm)[b] |
|---|---|---|---|
| C-171 | 50 | 458 ± 77 | na |
| C-171 str | 45 | 379 ± 43 | 20 |
| C-171 actD | 50 | 281 ± 26 | 20 |
| C-162 str | 50 | 163 ± 23 | 23 |
| C-162 actD | 65 | 120 ± 11 | 14 |
| C-80 | 60 | 352 ± 60 | 23 |
| C-80 str | 25 | 330 ± 41 | 12 |
| C-80 actD | 51 | 240 ± 7 | 19 |

[a] Calculated according to Eq. 1-3 at 20° C.
[b] Calculated according to Eqs. 4-6 for 90% rejection. na: not analyzed.

In batch C171, the total carbon flow was 1.5 times more than batch C80, and in batch C162 and C176 the catalyst total flow was 1.33 times lower than batch C80. Most part of the study was carried out with C80 laminates. Three type of laminates were tested: (i) as is; (ii) stretched (str); (iii) acetone densified (act dens; actD). Laminates modifications by either stretching or acetone condensation were performed in order to increase laminate density and surface homogeneity. As is and stretched (10%) laminates were supplied by Tortech. Acetone densification was performed by soaking pristine laminates in acetone for 5 min which were immediately dried at 70° C. in a drying oven for 10 min. Prior to their use, all laminates were soaked in double distilled water (DDW) for about 12 h and then carefully washed with a 70% ethanol solution to reduce any endogenous contamination (aseptic conditions).

Permeability Tests:

Permeability tests were performed with DDW using 50 mL Amicon® stirred filtration cells (Millipore) with a variable pressure between 0-1 bar, at a 0.25 bar interval. Permeate flux was calculated according to Eq. (1). Water temperature was measured before and after every filtration and the permeation results were normalized to 20° C. according to Eq. (2):

$$J^T = \frac{Q}{A} \quad (1)$$

$$J^{20} = J^T \times \frac{\mu^T}{\mu^{20}} \quad (2)$$

where: Q—volumetric flow rate [m³/h]; A—filtration area [m²]; $J^T$ and $J^{20}$—permeate flux at temperature T and 20° C., respectively [L/m²·h]; μT and $\mu^{20}$—dynamic viscosity at temperate T and 20° C., respectively [cP].

Normalized permeability at 20° C. ($L_p^{20}$) was calculated from the slope of the plot of $J^{20}$ vs. ΔP according to Eq. (3):

$$J^{20} = J_o^{20} \Delta P \times L_p^{20} \quad (3)$$

where $L_p^{20}$ is expressed in L/m²·h·bar; $J_o^{20}$—intrinsic flux at ΔP=0 [L/m²·h]; ΔP—transmembrane pressure [bar].

Selectivity Tests

In exemplary procedures, selectivity tests aimed at defining the absolute pore rating of the membranes were performed with globular protein markers and fluorescent polystyrene beads. The tests were performed using 50 mL Amicon (Millipore) stirred cells described above, applying a pressure of 1 bar following ASTM E1343-90 with some modifications.

Rejection of Protein Markers:

In exemplary procedures, selectivity tests were mainly performed by measuring the rejection of a protein mix standard of known molecular size (AL0-3042, Phenomenex) supplemented with bovine serum albumin (BSA) and blue dextran (BD) (Sigma-Aldrich) and assayed by gel filtration chromatography (GFC). BD was used as void volume marker for the GFC. Markers solution was prepared in filtered (0.22 μm filter, Millipore) DDW. The components, concentration and calculated size of each marker in the whole mixture are shown in Table 2 showing the properties and concentrations of the MW markers used in the selectivity tests.

TABLE 2

| Compound | MW (Da) | $d_H$ (nm) | Concentration [mg/mL] |
|---|---|---|---|
| Blue Dextran* | 2,000,000 | 87.07 | 1 |
| Bovine Thyroglobulin | 670,000 | 11.05 | 1 |
| IgA | 300,000 | 8.47 | 0.5 |
| IgG | 150,000 | 6.74 | 0.5 |
| BSA | 66,000 | 5.14 | 1 |
| Ovalbumin | 44,000 | 4.5 | 0.5 |
| Myoglobin | 17,000 | 3.29 | 0.2 |

Prior to start of the experiments all tested membranes were profusely rinsed with double distilled water (DDW) and soaked in a 1 g/L BSA solution in order to prevent adsorption of the proteins markers onto the membranes. The samples collected from the Amicon cells were filtered once again using a 0.2 μm Teflon syringe filter (17 mm, National Scientific) and analyzed by GFC on UV-HPLC.

The hydrodynamic diameter ($d_H$) of the proteins, all globular, was calculated as spherical model as presented in Eq. (4):

$$d_H = 0.132 \times MW^{0.33} \quad (4)$$

and for blue dextran was calculated based on the model of a linear molecule as presented in Eq. (5):

$$d_H = 0.11 \times MW^{0.46} \quad (5)$$

where MW is the molecular weight in Da and $d_H$ is given in nm.

Rejection of Fluorescent Beads:

In additional exemplary procedures, membrane rejection in the size range of 40-900 nm was also tested using polystyrene fluorescent beads (Spherotech) with different fluorophores, each color representing a different size. The beads specifications are presented in Table 3 below, showing Characterization of the fluorescent beads used for rejection measurement.

TABLE 3

| Color | Diameter (nm) | Excitation (nm) | Emission (nm) |
|---|---|---|---|
| blue | 860 | 600 | 675 |
| pink | 510 | 570 | 630 |
| yellow | 160 | 400 | 480 |
| nile red | 40 | 500 | 580 |

Beads concentration in all stock suspensions was 1% w/v. The experimental setup consisted of two solutions, the first one contained three colors, blue (diluted 1:100), pink and yellow (both diluted 1:200). The second solution contained the Nile red color-diluted 1:200 also. The Nile red color was masked by the other colors so it had to be used separately. The final volume of each solution was 10 ml. Each membrane was tested with this solution using the Amicon stirred cells at a 1 bar pressure as described above. A sample of 150 μL was taken from the permeate of each membrane and placed in a FluoroNanc 96 wells white plate (Nunclon, Thermo Scientific). The fluorescence bands were measured by an Infinite M200 Pro multimode reader (Tecan). DDW was used as blank.

Absolute Pore Rating Determination:

the absolute pore rating for a spherical molecule was calculated from the Ferry-Renkin equation, Eq. (6):

$$R = \left[1 - 2\left(1 - \frac{d_H}{d_m}\right)^2 + \left(1 - \frac{d_H}{d_m}\right)^4\right] \left[2.104\left(\frac{d_H}{d_m}\right) - 2.09\left(\frac{d_H}{d_m}\right)^3 + 0.95\left(\frac{d_H}{d_m}\right)^5\right], d_H \leq d_M \quad (6)$$

where R [dimensionless] is the rejection of a spherical particle (either globular proteins or polystyrene beads) and $d_m$ [nm] is the membrane pore diameter (or absolute pore rating). The term on the right-hand side of Eq. (6) describes the rejection of spherical particles due to steric screening at membrane pore entrance; the second term is associated with hindered convection of particles inside membrane pores (R≡100% for any $d_H \geq d_m$). Nominal pore rating and molecular weight cut off (MWCO) were drawn at 90% rejection from the semi-logarithmic plot of rejection vs. hydrodynamic rate or molecular weight, respectively.

Chemical Resistance Tests

In order to evaluate the chemical resistance of the CNT membranes, experiments were carried out applying solutions of common chemicals used for chemical cleaning and cleaning in place (CIP) during typical membranes operation, but at harsher conditions (higher concentrations and/or longer exposure time): 2 N HCl, 2 N NaOH and a 0.5-2 g/L NaOCl. Exposure lasted for 24 hours and samples were taken at time 0, 1 and 24 hours. The effect of the chemical treatment on the CNT laminates was tracked by permeability measurement with double distilled water (DDW) and X-ray photoelectron spectroscopy (XPS) characterization (relative C and 0 content) to determine the possible changes in chemical composition. For the C-80 laminates, selectivity was also tested following the chemical resistance tests in order to estimate the potential effect on chemical cleaning on the overall membrane performance (permeability and selectivity).

In exemplary procedures, the exposure to the cleaning chemicals was performed as follows. Several coupons (replicates) of each laminate were soaked in the indicated solution for the indicated time in Petri dishes. Then coupons were sampled, thoroughly washed in DDW and tested for permeability, selectivity and XPS. Tests were repeated at least three times. Permeability was tested with DDW in the stirred cells mentioned above water under pressure of 1 bar (see below). Selectivity was performed using the protein markers as described hereinbelow.

Analytical Techniques

HR-SEM Microscopy and Tortuosity Estimation:

In exemplary procedures, laminates were sputter coated with carbon and visualized by using a Zeiss Ultra-Plus FEG-SEM. In order to measure the tortuosity the SEM images were taken at different layers of the CNT laminates by pealing the upper layer gently with carbon tape. Tortuosity was also measured by image analysis software (Olympus Stream).

Atomic Force Microscopy (AFM):

In exemplary procedures, surface topography, roughness, electrostatic forces and phase images of the CNT laminates were evaluated using UHV/VT AFM/STM system (Scienta Omicron) in constant force mode (50 nN). Silicon tip coated with gold (supplied from NT-MDT) was used for the measurements. The scans were performed at a rate of 0.5 Hz with a resonance frequency of 13 kHz, k=0.2 N/m, where k is the spring constant of the cantilever. The long range attractive/repulsive forces between the probe tip and CNT laminate surface were recorded by AFM up to distances of about 600 μm.

Contact Angle Analysis:

In exemplary procedures, the contact angle of the membrane surface was measured using a Drop Shape Analyzer (DSA100, Kruss). The measurements were carried out by dropping a 3-μL droplet of water on the membrane surface. The experiments were repeated at least in 10 different locations at the surface and the mean values are reported.

Zeta Potential Analysis:

In exemplary procedures, Zeta potential of CNT laminates was measured using surPASS-3 electrokinetic analyzer (Anton Paar) based on a streaming potential and streaming current measurement. Zeta potential was examined in a 0.001M KCl electrolyte solution in a pH range from 2 to 10 using 0.05 M KOH and 0.1 M HCl solutions.

Gel Filtration Chromatography:

In exemplary procedures, the samples of protein mix for selectivity tests were analyzed by GFC on an Agilent 1100 HPLC equipped with a diode array detector (Hewlett Packard). Monitoring was performed at 254, 280 and 620 nm. A Yarra SEC 3000 column (Phenomenex, 30 cm length, 3 μm pore size) was used under isocratic conditions at a flow rate of 1 ml/min. A solution of 0.1 M of phosphate buffer (pH=6.8) with 0.025% sodium azide was applied as eluent. The injection volume was 10 μL.

X-Ray Photoelectron Spectroscopy:

In exemplary procedures, surface composition of the CNT laminates was analyzed using a commercial XPS system (Thermo VG-Scientific—Sigma probe) with a monochromatic Al Kα at 1486.6 eV source and a hemispherical electron energy analyzer. A 100 W X-Ray primary beam size of 400 μm was used during data collection. XPS survey spectra were recorded then with a pass energy of 200 eV, from which the atomic surface chemical composition was determined. XPS survey scan done as a plot of the number of electrons (counts/s) versus the binding energy (eV). The atomic concentrations were calculated using elemental sensitivity factors without applying any standardization procedure. The core level binding energies of the different peaks were normalized by setting the binding energy for the C1s at 285.0 eV. In addition to the survey mode, high-resolution XPS mode (HR-XPS) was performed in order to evaluate chemical functionalities for the C1s line. The HR-XPS spectra were collected with a pass energy of 20 eV and analyzed with a deconvolution routine of the C1s line, which can decompose each spectrum into individual mixed Gaussian-Lorentzian peaks.

Hydrogen Peroxide Estimation:

the electrically generated hydrogen peroxide was measured using an Amplex Red Hydrogen Peroxide/Peroxidase Assay Kit (molecular probes). A modified micro cell (cuvette) was used to perform the experiments. The sides of the cuvette were pasted by CNT laminates and about 1 cm length of sheets was left in order to connect to the power source. 2 ml of NaCl 50 mM were used (without bacteria) for measurements of $H_2O_2$ at different electric potential (0, 1000 mV, 3000 mV, 4500 mV, 6000 mV). After 30 min, 50 μL of the sample solution were mixed with 50 μL of reagent solution according (Amplex) and tested by a 96 wells plate reader at an excitation of 530 nm and emission of 590 nm.

Example 2

Characterization of CNT Laminates

Morphology of CNT Laminates:

Detailed structural characterization of the C-80 laminates is presented in FIGS. 1A-I, FIG. 2 and in Table 4 below showing Characteristics of C-80 laminates including, flux pore rating, contact angle tortuosity, roughness, and Molecular weight cut-off (MWCO).

related to the densification of the laminates, which decreased tortuosity and in turn permeability. Indeed, for C-80 as which displayed the highest tortuosity resulted in the highest permeability (352±60 LMH) (see Table 4).

Figure 1A:
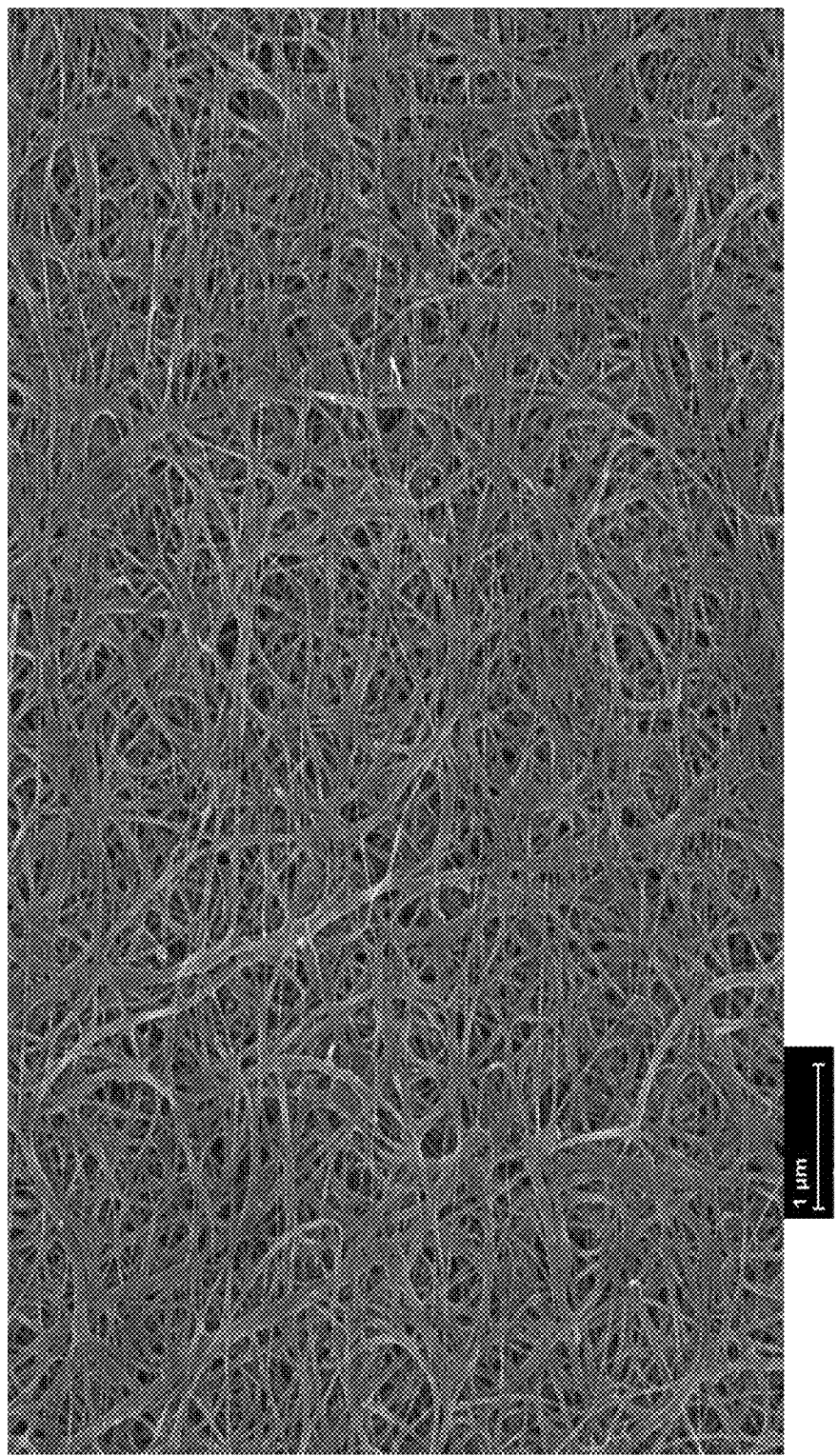
Figure 1B:
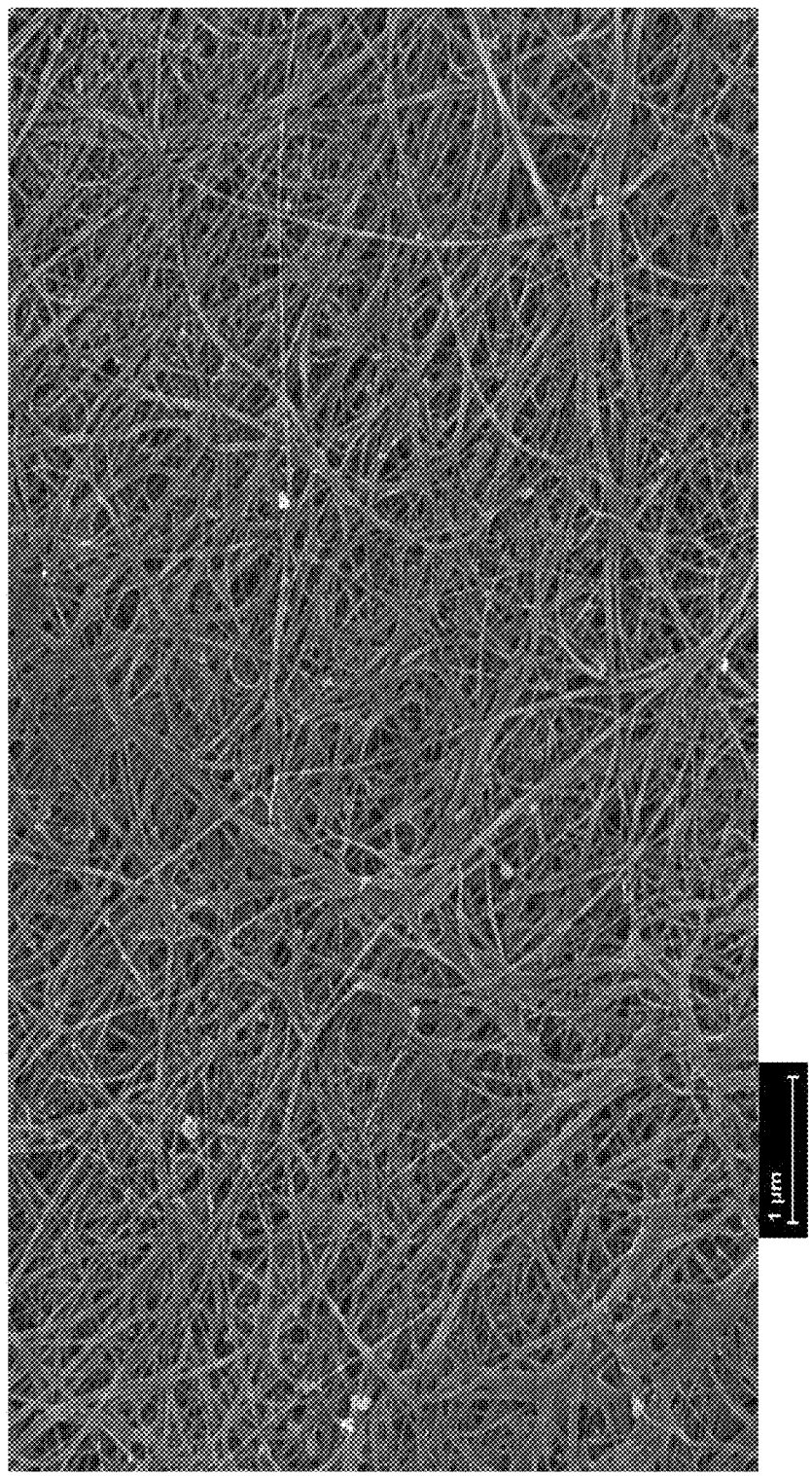
Figure 1C:
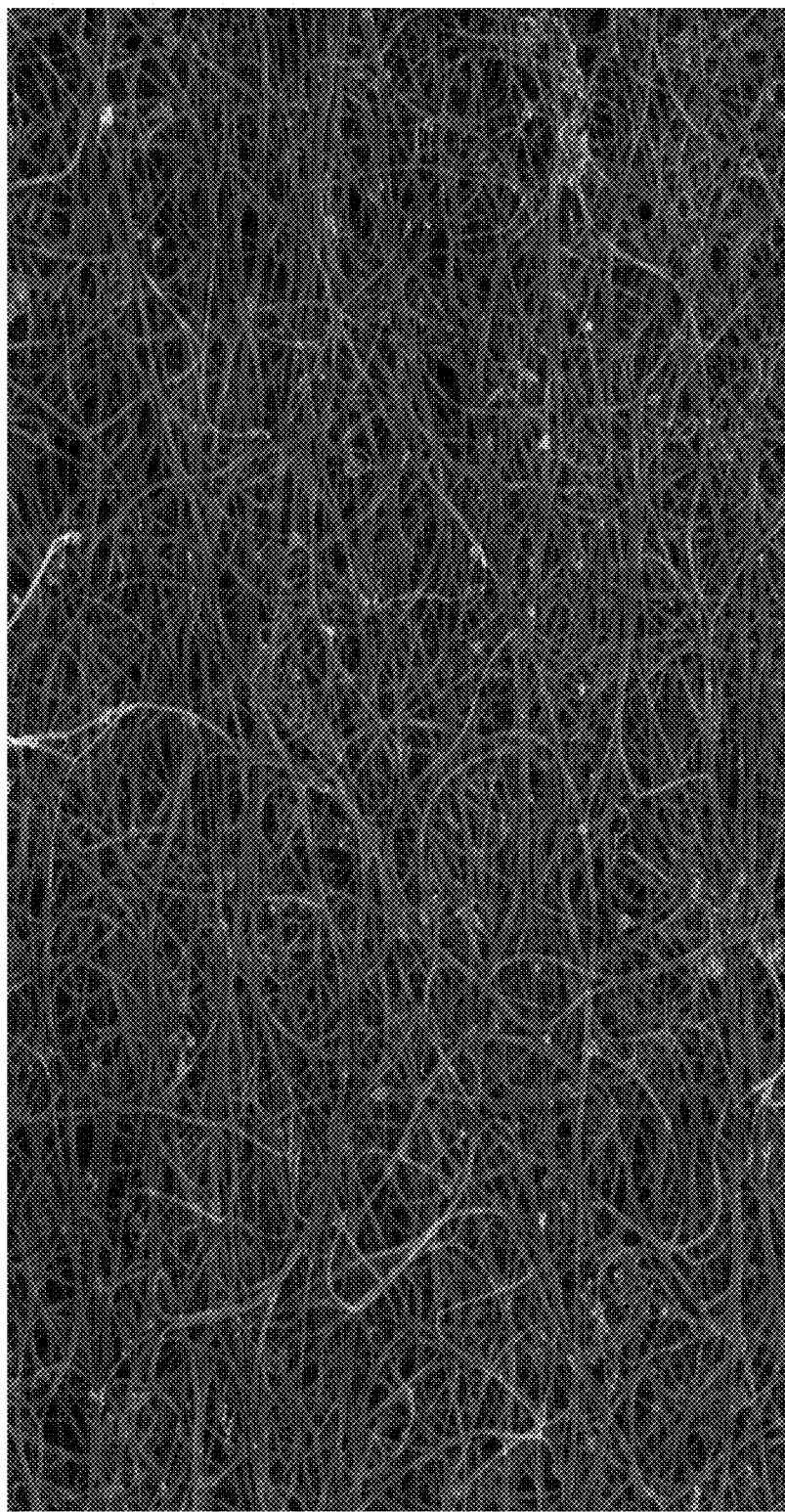
Figure 1D:
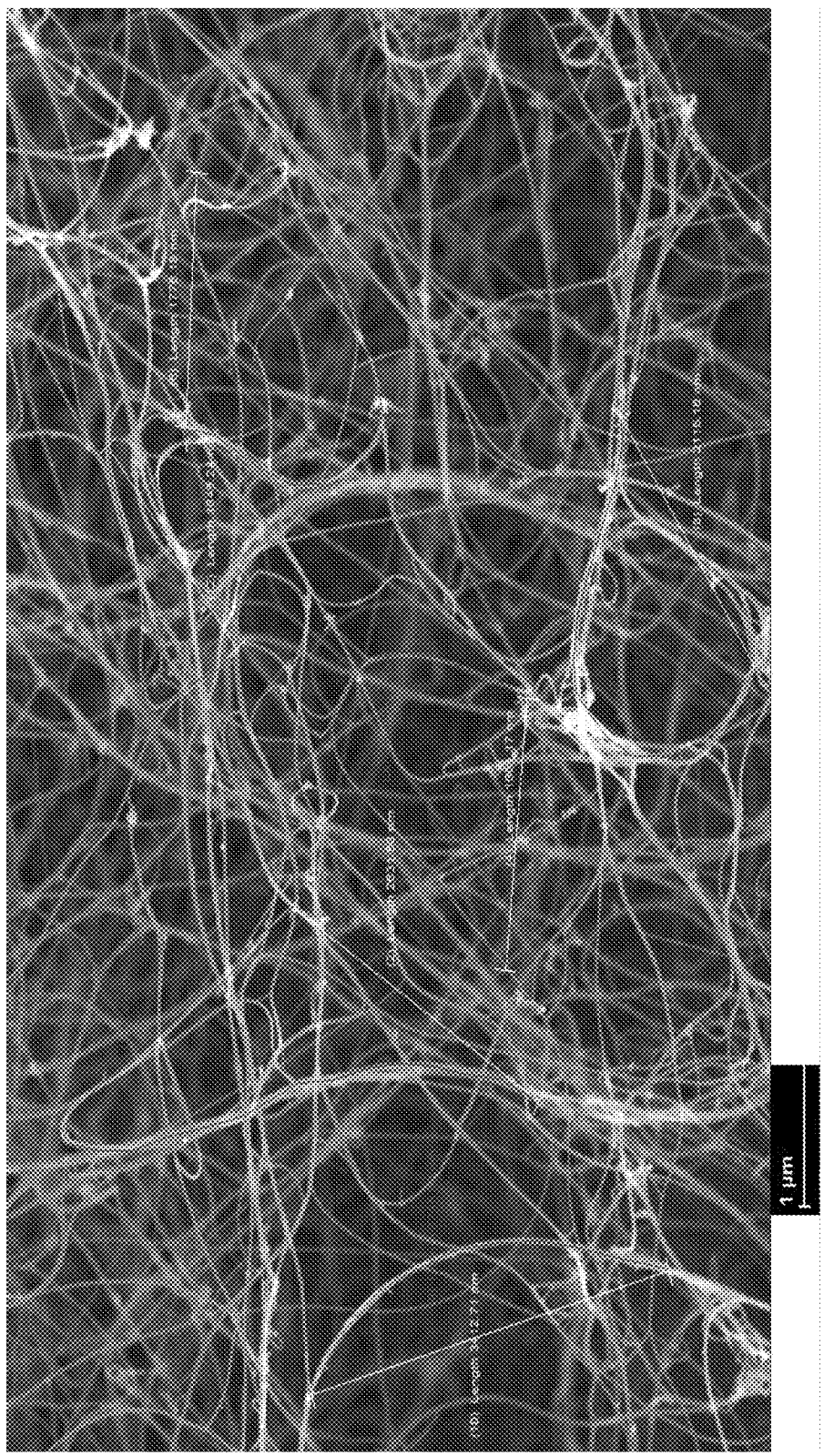
Figure 1E:
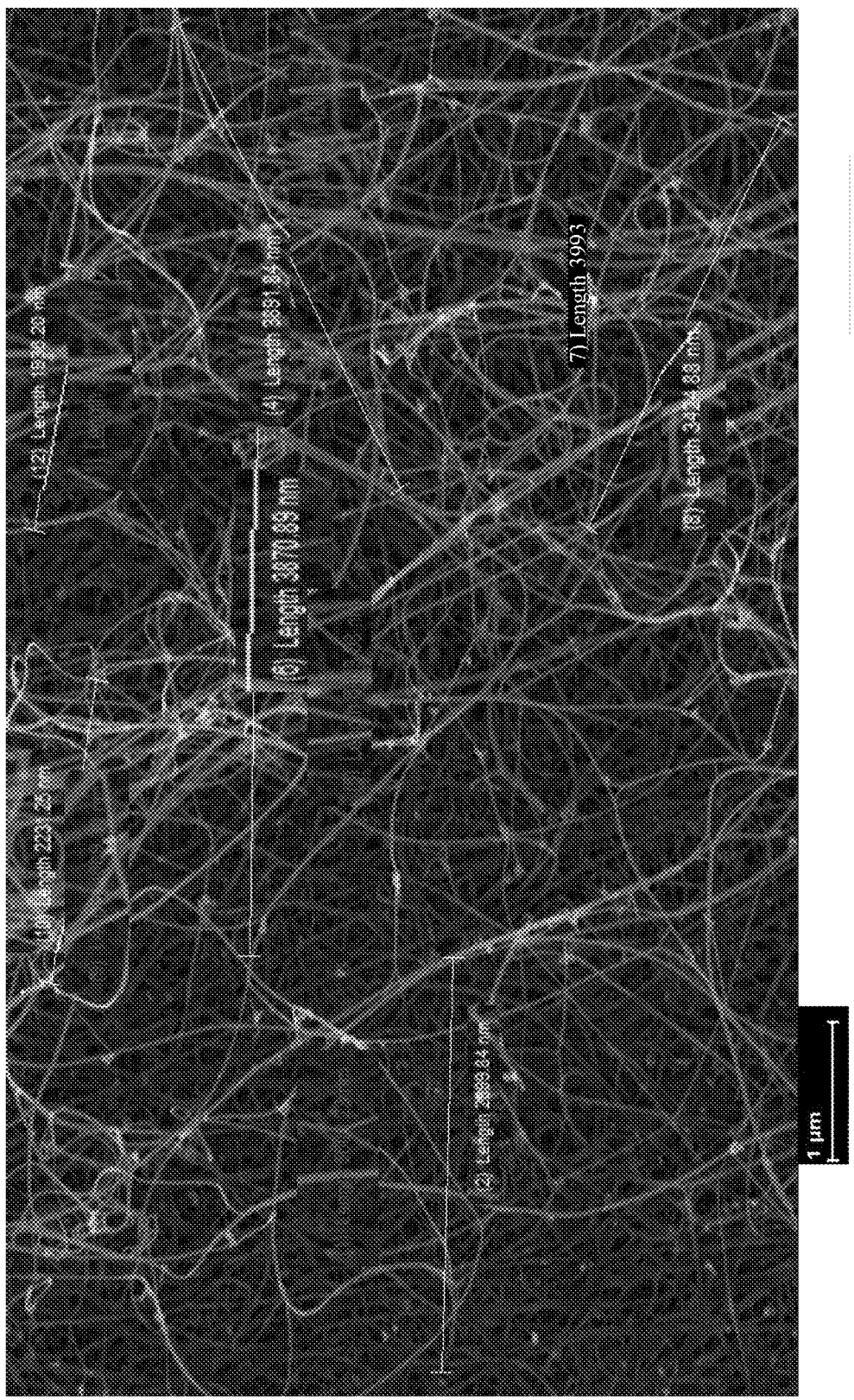
Figure 1F:
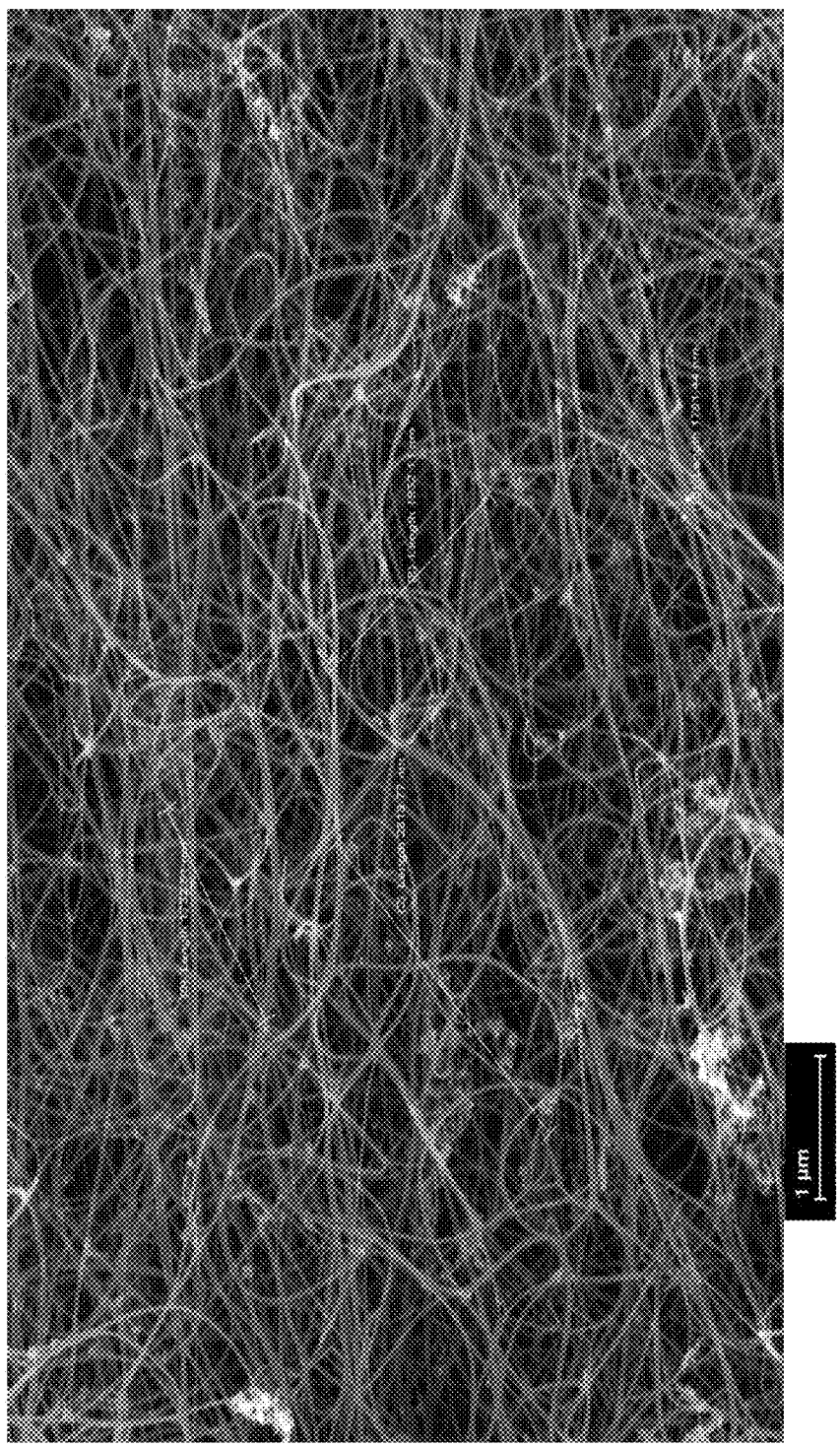
Figure 1G:
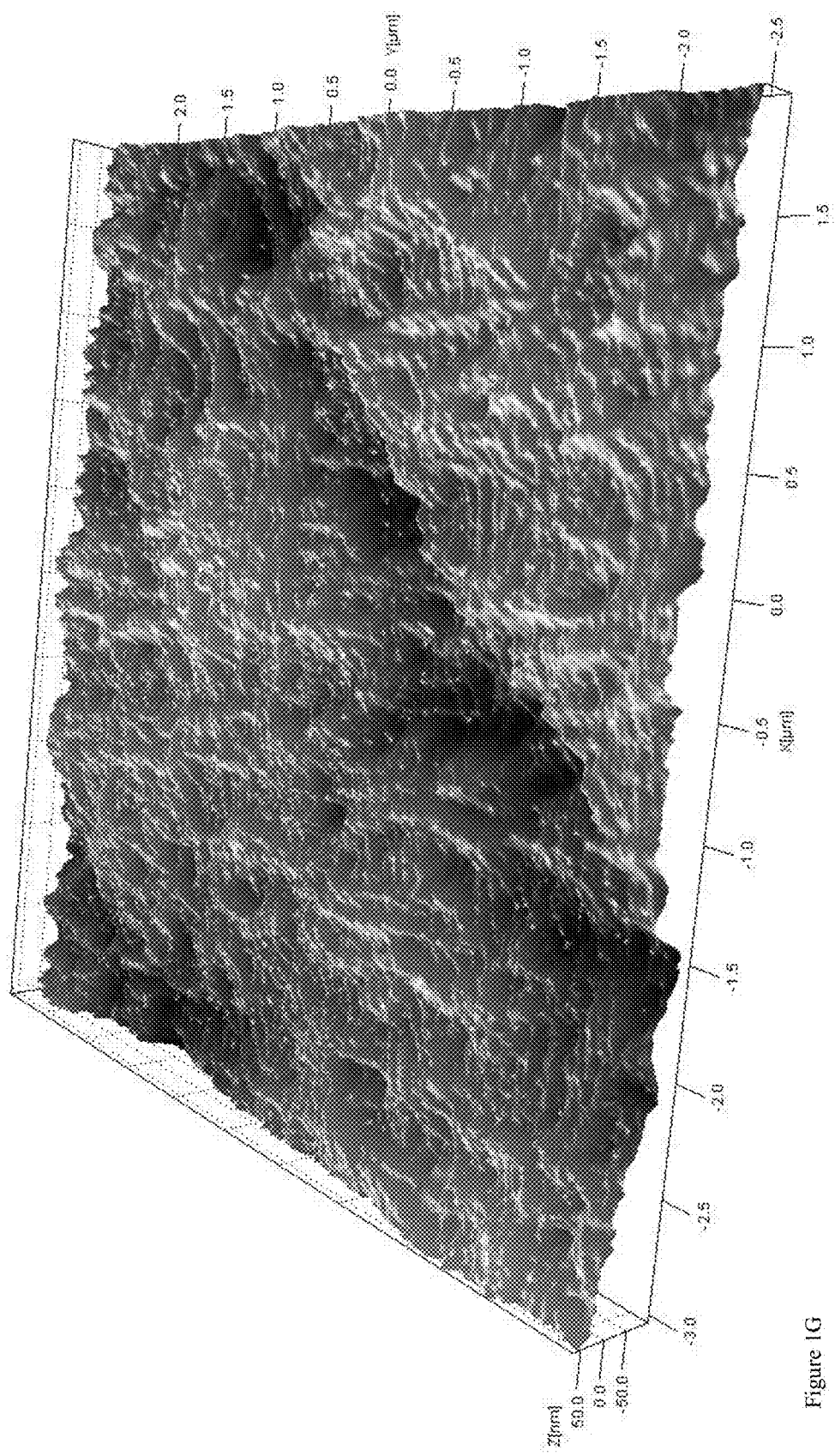
Figure 1H:
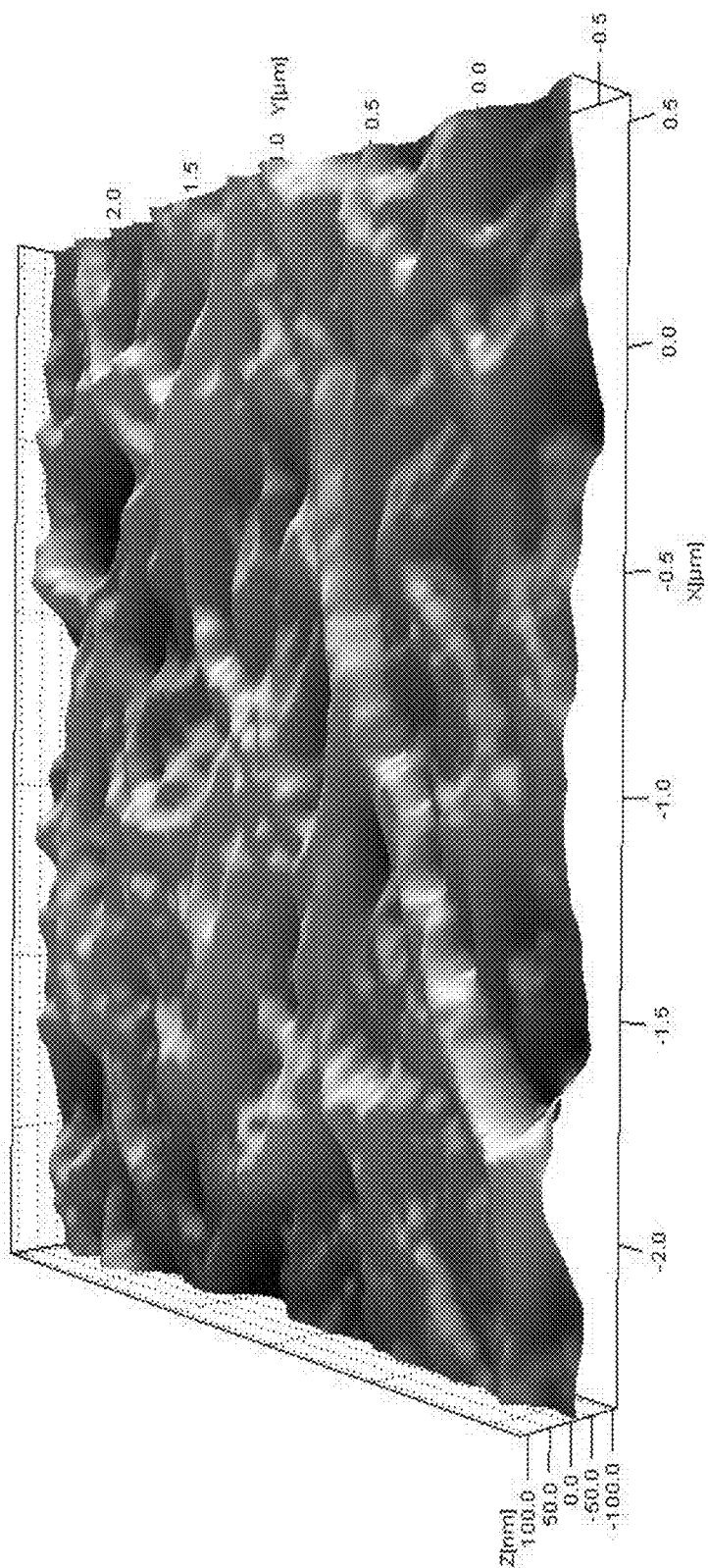

The AFM topography of CNT laminates is presented in FIG. 1G-I. It can be seen that all these CNT laminates exhibited a uniform structure. The measured electrostatic force curves of the three CNT laminates are shown in FIG. 3. The calculated repulsive forces of C-80, C-80 str and C-80 act dens at a distance of 2 μm were greater than 21 nN, 54 nN and 35 nN respectively and converged less than the 9 nN at 600 μm. Indeed, repulsive forces are very short-range forces and display an exponential or inverse power decaying profile with distance. The average roughness and root mean square (RMS) are shown in Table 4. In agreement with the repulsive forces, both roughness (34.2±3.0) and RMS (43.5±3.5) of C-80 str displayed the largest values. In general, the roughness of the CNT laminates was slightly higher than reported values for VA CNT membranes, as was the tortuosity factor.

Remarkably, AFM data inversely correlated contact angle and selectivity (see Table 4) and thickness (see Table 1) of the laminates. The lowest contact angle was observed for C-80% str (78.3±7.12°θ) corresponding to a highest roughness and better selectivity (absolute rating at 15 nm) and smallest thickness (25 μm), compared to C-80 (102.2±6.7°θ) and C-80 act. dens (118.1±9.1°θ). The more hydrophilic laminates, C-80 as is and act. dens., displayed lower selectivity (absolute rating at 29 and 25 nm, respectively) in

TABLE 4

| Laminate | Tortuosity factor ($l_0/l_e$) | $L_p^{20}$ ($J_o^{20}$) [LMH/bar]$^{a*}$ | Average Roughness (nm) | Mean square Root roughness (nm) | Contact angle (θ) | MWCO (kDa) |
|---|---|---|---|---|---|---|
| C-80 | 2.76 ± 1.37 | 352 ± 60 (101) | 18.7 ± 7.9 | 24.0 ± 10.2 | 102.2 ± 6.7 | 65 |
| C-80 10% str | 2.39 ± 1.45 | 330 ± 214 (59) | 34.2 ± 3.0 | 43.5 ± 3.5 | 78.3 ± 7.1 | 18 |
| C-80 act dens | 1.75 ± 0.50 | 240 ± 7 (47) | 22.6 ± 7.9 | 28.0 ± 9.1 | 118.1 ± 9.1 | 26 |

Values represent average ± standard deviation of at least 3 replicates (expect absolute rating): a) calculated according to Eqs. 1-3; b) calculated according to Eqs. 4-6.

HR-SEM micrographs of both top layer-surface (FIGS. 2A-C) and cross section (FIGS. 2D-F) of well aligned as is C80 laminates at different magnifications ranging from 5 kX to 300 kX are shown. As seen from these micrographs, dense CNT fibers entangled multi-directionally, consisting of curved tubes could be noticed. Comparative HR-SEM micrographs of C-80 as is, stretching modified and acetone modified laminates at a magnification of 30× are presented in FIGS. 1A-C. Hence, a thin section of the top layer was carefully peeled off from the laminates and imaged (FIGS. 1D-F). It shows a clear picture of the shape of CNT fibers. The curvature of CNTs, which can be quantitatively evaluated, is indicative of the tortuosity. The tortuosity factor ($l_o/l_e$), defined as the ratio of the length of the curved line between two points-$l_o$ (red lines in FIGS. 1D-F) to the linear distance between the two points-$l_e$ (white lines in FIGS. 1D-F). The tortuosity of the each layer was measured at least in 6 different places. The calculated tortuosity factor of unmodified laminates shows quite larger values (2.8±1.4) than the modified laminates, 2.4±1.5 for stretched and 1.8±0.5 for acetone densified (see Table 4). The tortuosity factor reported in the literature for CNT wall and VA CNT membranes, were quite less than the present CNT laminates. Tortuosity seems correlated to permeability, probably correspondence to a smaller roughness. Noticeable, the more hydrophilic C-80 as is (zeta potential=−43.5±4.9 mV at pH 7) displayed the highest permeability. The intrinsic hydrophobic nature of CNT laminates is attributed to the low surface energy of CNT, which could benefit the mitigation of membrane fouling in the cross-flow filtration mode. The adsorption of foulants on a low-energy surface is normally weak and can be easily rinsed-off by the shearing forces of the cross-flowing feed solution.

Water Permeability and Selectivity:

The normalized water permeability values of the different CNT laminates tested are shown in FIGS. 4A-C. A summary of permeability at 20° C. of the different CNT membranes is shown in Table 1 above.

As shown in the data presented all pristine membranes displayed very high permeability which was somewhat reduced upon modification by either stretching or acetone densification. Although the pristine membranes displayed higher permeability they also showed a higher variation denoting the lack of uniformity of the laminates, which was reduced by post-synthesis modification. Overall, a one to two orders of magnitude higher water permeability was observed in all the CNT laminates than the commercially available ultrafiltration (UF) membranes, with typical values are 20-40 LMH/bar.

As seen in the data presented, the linear fit does not crossed the axis intersection indicating that water permeates through these membranes even without applied pressure (i.e., intrinsic percolation). Intrinsic percolation or seepage phenomena in dense-array outer-wall CNT membranes are common. In order to hinder this behavior, two modifications were performed to the membranes i.e., 10% mechanical stretching and acetone densification (FIGS. 4B and 4C) respectively. The modified CNT membranes reduced the intrinsic percolation by 1-2 folds (see Table 5). Even though these modifications decreased the permeability compared to the unmodified laminates they enhanced selectivity (see below). Nevertheless, permeability of the modified laminates still remained at least one order of magnitude higher than commercial polymeric UF membranes, in line with published literature.

The selectivity of the C-80 membranes, characterized by absolute pore rating using a mixture of fluorescent polystyrene beads (40-860 nm) and globular protein markers (3-90 nm), are presented in Table 1. It can be seen that all the membranes displayed an absolute pore rating in the range of highly selective ultrafiltration membranes (15-30 nm). As an example, the plot for the unmodified C-80 membrane is presented in FIG. 5. As shown in the graph, C-80 membrane displays complete rejection of proteins larger than 150 kDa (IGg, $d_H$=6.7 nm) with an absolute rating of 29 nm calculated according to Ferry-Renkin equation. This pore size fits well the high resolution end of a UF membrane. When considering the permeability of the membranes ranging from 120-400 LMH/bar (see FIGS. 4A-C), the CNT laminates present an exceptional combination of high permeability and high selectivity, compared to any commercial UF membrane. This high selectivity regardless of the high permeability can be most probably regarded to adsorption and intrinsic tortuosity across the whole thickness of the nonwoven laminates (by average 25-50 μm), acting as self-supporting membranes, in line with previous reports.

This combination of features offers a unique opportunity of application of UF membranes, and especially at the harsh conditions such as wastewater treatment and purification (effluents filtration, MBR) taking into account the high chemical stability and temperature resistance.

When compared to composite flat sheet membrane the CNT laminates show two to four folds higher permeability. For instance, about 53 LMH/bar pure water flux were reported in PES/NH$_2$-MWCNT nanocomposite UF membrane.

Without being bound by any particular mechanism, it is assumed that as the densification increases, more CNT wall surface becomes available for water flow, thereby resulting in a greater flow velocity leading to higher permeability. A larger pore size in the range of microfiltration has higher flux than the CNT laminates.

It is noteworthy that the simplicity of fabrication and post-synthesis modification of the dense-array outer-wall CNT membranes presented here, added to support-free configuration that enhances chemical and temperature stability, make them especially suited for harsh application conditions.

Chemical Resistance of CNT Laminates

Chemical resistance tests were performed in order to evaluate the behavior of the membranes to chemical treatments applied for routine cleaning and CIP during membrane operation, but under extreme conditions (higher concentrations and/or longer exposure time). The relative permeability values of all membranes after the treatment with 2 N NaOH, 2 N HCl and 500-2000 mg/L of NaOCl are presented in Table 5 presenting post-treatment permeability of different CNT membranes following chemical resistance treatments.

TABLE 5

|  | Treatment | | | | | |
| --- | --- | --- | --- | --- | --- | --- |
|  | NaClO 0.5 g/L | | NaClO 1 g/L | | NaClO 2 g/L | |
|  | Time (h) | | | | | |
|  | 1 | 24 | 1 | 24 | 1 | 24 |
| C-171 | 0.97 ± 0.02 | 1.04 ± 0 | 0.88 ± 0.11 | 1.1 ± 0.02 | 1.01 ± 0.02 | 0.99 ± 0.01 |
| C-171 str | 1 ± 0.02 | 1.05 ± 0.02 | 0.99 ± 0.09 | 1.05 ± 0.02 | 0.97 ± 0.03 | 0.93 ± 0.03 |
| C-171 act dens | 0.98 ± 0.01 | 1.01 ± 0.01 | 0.99 ± 0.01 | 1.1 ± 0.01 | 0.95 ± 0.03 | 0.94 ± 0.02 |
| C-162 str | 0.98 ± 0.01 | 1.02 ± 0.02 | 0.96 ± 0.03 | 1.05 ± 0.01 | 1 ± 0.01 | 1.05 ± 0.05 |
| C-162 act dens | 1.04 ± 0.03 | 1.06 ± 0.01 | 1 ± 0.01 | 1.03 ± 0 | 1.08 ± 0.02 | 1.07 ± 0.02 |
| C-80 | 0.96 ± 0.03 | 1.01 ± 0.02 | 0.92 ± 0.03 | 0.98 ± 0.04 | 1.03 ± 0.02 | 1.05 ± 0.02 |
| C-80 str | 0.97 ± 0.03 | 1.10 ± 0.01 | 1 ± 0.04 | 1.12 ± 0.02 | 1 ± 0.03 | 0.94 ± 0.03 |
| C-80 act dens | 0.96 ± 0.01 | 1.02 ± 0.01 | 1.04 ± 0.01 | 1.08 ± 0.02 | 0.99 ± 0.01 | 1.05 ± 0.02 |

|  | Treatment | | | |
| --- | --- | --- | --- | --- |
|  | NaOH 2N | | HCl 2N | |
|  | Time (h) | | | |
|  | 1 | 24 | 1 | 24 |
| C-171 | 1 ± 0.02 | 1.06 ± 0.01 | 1.03 ± 0.04 | 1.03 ± 0.02 |
| C-171 str | 1.15 ± 0.02 | 1.16 ± 0.01 | 0.98 ± 0.03 | 1.01 ± 0.04 |
| C-171 act dens | 1.12 ± 0.01 | 1.11 ± 0.03 | 1.06 ± 0.02 | 1.22 ± 0.06 |
| C-162 str | 1.13 ± 0 | 1.10 ± 0.02 | 1.01 ± 0 | 1.01 ± 0.02 |
| C-162 act dens | 1.14 ± 0.02 | 1.12 ± 0.01 | 1.10 ± 0.05 | 1.09 ± 0 |
| C-80 | 1.17 ± 0.02 | 1.16 ± 0.01 | 1.15 ± 0.01 | 1.11 ± 0.03 |
| C-80 str | 1.14 ± 0.01 | 1.13 ± 0.01 | 1.06 ± 0.04 | 1.16 ± 0.02 |
| C-80 act dens | 0.91 ± 0.02 | 1.13 ± 0.02 | 1.01 ± 0.02 | 1.01 ± 0.02 |

*Data represent relative permeability with regards to the initial permeability (t = 0) before treatments (controls).

The results indicate that permeability of all the membranes was only slightly influenced (up to 5%) by long terms exposure to the concentrated chemicals. Some membranes exhibited a decrease in the permeability as a result of a specific treatment, for example C-171 str displayed a decrease in the permeability after the treatment with 2 g/L NaClO. In most of the cases though, an increase in the permeability was observed, especially after 24 h of exposure to the chemicals, as in the case of C-162 act dens after the treatment with 2 N HCl. Interestingly, the treatment of 2 N NaOH caused the steadiest increase of permeability to all the membranes (see Table 5).

A more comprehensive evaluation of chemical resistance was performed for the C-80 membranes. The relative permeability data are presented in the three bottom rows of Table 5, the relative change in pore rating before and after chemical resistance tests in FIG. 6 and the typical deconvolution of the XPS C1s lines of the unmodified C-80 membranes after 24 h exposure to chemicals in FIGS. 7A-D and in Table 6 (presenting surface atomic composition (in %) based on XPS survey measurements of unmodified CNT C-80 laminates after chemical resistance tests) and in Table 7 (summarizing data regarding HR-XPS C1s line of peak location (nm) and the relative ratio of the peak surface area).

As seem from the results presented, no significant changes in the permeability were found among the treatments, although some increase in the permeability was observed especially after 24 h of exposure to HCl and NaOH (see Table 5).

TABLE 6

| Elements | C | O | Fe | Si | Na | Cl | C/C + O |
|---|---|---|---|---|---|---|---|
| Control | 94.46 | 4.73 | 0.32 | 0.49 | — | — | 0.95 |
| 2NHCl | 95.97 | 3.73 | 0.30 | 0 | — | — | 0.97 |
| 2000 ppm NaOCl | 91.68 | 6.89 | 0.48 | 0 | 0.71 | 0.25 | 0.93 |
| 2N NaOH | 95.22 | 4.49 | 0.29 | — | — | — | 0.95 |

TABLE 7

| Sample | XPS data | Peak #A C- sp2 | Peak #B C sp3 and defects | Peak #C C—O | Peak #D Carbonates | Peak #E π- π* |
|---|---|---|---|---|---|---|
| C-80, #7 | Binding Energy (eV) | 284.1 | 285.5 | 286.7 | 288.3 | 290.4 |
| | Peak Area Ratio (%) | 73.8 | 13.5 | 6.0 | 2.5 | 4.2 |
| 2N HCl, #8 | Binding Energy (eV) | 284.0 | 285.2 | 286.9 | 289.7 | 290.4 |
| | Peak Area Ratio (%) | 73.5 | 13.2 | 6.4 | 3.0 | 3.9 |
| NaOCl, #9 | Binding Energy (eV) | 284.1 | 285.2 | 286.4 | 288.4 | 290.2 |
| | Peak Area Ratio (%) | 74.1 | 13.5 | 5.6 | 3.4 | 3.4 |
| NaOH, #10 | Binding Energy (eV) | 284.1 | 285.2 | 286.4 | 288.7 | 289.9 |
| | Peak Area Ratio (%) | 72.4 | 12.5 | 6.2 | 3.5 | 5.4 |

Regarding selectivity, in most of the cases the treatments improved the absolute pore rating that resulted in better rejection of the markers (see FIG. 6). Without being bound by any particular theory, this behavior might be explained by increased van der Waals interaction between CNT fibers upon treatment (similar to the acetone condensation that was made on part of the laminates) resulting in a higher rejection, thus increasing selectivity.

XPS is one of the crucial surface analytical techniques to provide useful information on the nature of the functional groups and also on the presence of structural defects on the CNT laminate surface. From the XPS results presented Table 6, it appears that in spite of small variations in the relative C/O-carbon to oxygen ratio (change was in the order of ±0.2), the laminates displayed a good resistance to oxidant chemicals as well as acid and base. For NaOCl treatment which displayed an only slight change in permeability, only slight change on C/O ratio was observed in XPS at 2000 mg/L. On the other hand, the NaOH treatment which resulted in the steadiest increase in the permeability, corresponded to almost no change in C/O ratio. The treatment with HCl had mild effect on the permeability and displayed a slight increase in the C/O ratio. These results reflect that in spite of the harsh conditions the laminates displayed a slight surface modification. For hydrochloric acid treatment, an $sp^2$ hybridized carbon enrichment was reported to take place at the surface, thus forming a protective barrier against chlorine degradation and fouling. Taking into account that whole laminates display some natural irregularities (assays were performed in 44.5 mm coupons, the size of a 50 mL Amicon stirred cells, although multiple replicates were analyzed for each case), it can be conclude that these surface changes are minor. Furthermore, one should consider than in practice membranes will be subjected to considerable milder conditions.

High Resolution-XPS has been conducted for evaluating chemical environment of C1s line of the C80 as is laminates after exposing membranes to different chemical treatments. Typical deconvolution curves of the HR-XPS C1s lines of the laminates after 24 h exposure to chemicals are shown in FIGS. 7A-D and the different peak attributions as summarized in Table 7. After deconvolution, the C1s line showed a main peak at 284.0 eV (peak#A) that was attributed to the graphitic structure ($sp^2$ hybridized). The peak at 285.1 eV (peak#B) was either attributed to $sp^3$-hybridized carbon or defects due to carbon atom that are no longer in the original tubular structure, whereas following peaks 286.4 eV (peak#C), and 288.4 eV (peak#D) are indicative of different oxygen based functionalities at the chemical environment of the carbon atoms. Finally the peak#E (at 290 eV) is related to π-π* transition loss peak. HR-XPS data are summarized in Table 7 with the different peak attributions and the proportional peak area ratios. After the membrane was exposed to 2N HCl no significant changes could be observed comparing to the reference sample. Similar results were observed for membranes after exposure to NaOCl or NaOH. XPS results and peak attribution are in good agreement.

Overall, results of the chemical resistance treatments indicate that these membranes are very resistant, even to harsh conditions. It should be noted that the fact that the laminates represent a monolithic membranes all made of CNTs present the advantage of uniform and high overall resistance (chemical and thermal). Although some slight sign of oxidation appear from the prolonged exposure to excessively high chemicals dose, one may expect these membranes to be very resistant to chemical cleaning and cleaning-in-place treatments that are common in the industry. These results further indicate that exposure to harsh chemical conditions did not modify the performance of the membranes, neither in terms of permeability nor in terms of selectivity.

Taken together, the filtration capabilities, hydraulic properties and chemical resistance of self-supported CNT laminates were characterized. The molecular weight cut-off of the membranes correspond to the selectivity range of tight OF membranes (absolute pore rating about 15-30 nm). The CNT membranes tested displayed outstanding properties comprising very high permeability of 120-400 LMH/bar, one order of magnitude higher for the same separation selectivity of existing commercial membranes. It appears that this high selectivity regardless of the high permeability may be due to hindered convection of particles, i.e., adsorption and tortuosity, across the whole thickness of the nonwoven laminates (by average 25-50 µm). Laminates displayed the added benefit of high chemical resistance to typical chemicals used for membrane cleaning in filtration, including HCl; NaOH and NaClO at long-term exposure and high concentration. This combination of features offers a unique opportunity of application in the UF range, and especially at the harsher conditions such as wastewater treatment and purification (effluents filtration, MBR). Moreover, these CNT laminates display intrinsic antibacterial properties and high electrical conductivity that can be applicable for biofouling control. These CNT membranes have the potential to tackle the present and future challenges in water purification.

Example 3

Antimicrobial Applications of CNT Membranes

Materials and Methods
Membranes

Self-supporting CNT membranes were supplied by Tortech Nano Fibers (TNF). Fibers and ribbons of CNT were fabricated by direct spinning from chemical vapor deposition (CVD) synthesis using a liquid source of carbon and an iron nanocatalyst. The molecular weight cut off (MWCO) the membranes is in the tight ultrafiltration range. Their structure provides the CNT membrane with high strength, increased thermal stability (up to 400° C.), wide chemical resistance, high permeability and high electric conductivity (~40,000 S/m). The electrical resistance of the membranes was measured with a LCR 4300 meter (Wayne Kerr Electronics), values reported are for wet conditions.
Microorganism A mutant strain of *Pseudomonas putida* S12 (ATCC 700801) was used as a model organism. A single Gram (−) species biofilm was used in order to simplify the test system and provide a means for easier tracking of biofilm development without the influence of an interaction between different bacterial populations. Bacteria were preserved in small stock vials with 25% glycerol at −80° C. as a pure culture. The content of the stock vials was thawed and plated on Luria Bertani (LB)-agar plates containing 50 µg/mL kanamycin (Sigma Aldrich) and incubated at 30° C. for 24 h. Then, one colony picked from the plate was subcultured at the same conditions at 150 rpm in LB broth (TOC≈20 mg/L) supplemented with 50 µg/mL kanamycin. The bacteria were harvested to an average optical density of approx. $OD_{600}$=0.7.

Example 4

Electrical Membrane Biofouling System (EMBS)

The Experimental System and Operation Conditions

The biofouling inhibition activity was tested in a flow-through electrical membrane biofouling system (EMBS). The EMBS consisted of a six channel-flow-through membrane cells with a set of electrodes each, operating in continuous mode with internal recirculation through two bioreactors, with every three flow cells connected to one recirculation reactor (FIG. 8 and FIGS. 9A-C).

All cells were equipped with two manometers and pressure transducers (inlet and outlet pressure) and a flow valve controller. The system was operated at a low linear flow velocity of about 0.02 m/s. The EMBS was operated with continuous recirculation throughout the bioreactors at a retention time of approx. 20 min, which is far below the doubling time of the model bacterium at such growth conditions. This was done to encourage and perpetuate biofilm formation. The feed consisted of a nutrient stream made of sterile LB medium diluted in place (1:250) with filtered tap water (0.8/0.2 µm filter, Pall) which was fed into a 40 mL recirculating reactor using a peristaltic pump (Cole-Parmer) (FIG. 8). Each reactor was equipped with a thermocouple for feed temperature monitoring. The total organic carbon (TOC) final concentration in the feed stream upon dilution was ~20 mg/L.

Prior to each experiment, the membranes were assembled in the aseptically cleaned flow cells and then washed with filtered water for an hour. Next, the system was inoculated to a bacterial concentration of $10^4$ CFU/mL and kept for 1 h in closed circulation. Following this, diluted LB began to be fed to the reactors and the system was operated in continuous mode with recirculation. Once bacteria were inoculated into the reactor, the electrical field was applied on each membrane as indicated. Due to the biofilm encouraging conditions (i.e. feed concentration and loading rate, inoculum concentration and suspended bacteria retention time), experiments duration was set to approximately 72 hours.

Experiments were performed in two modes: (i) in flow-through conditions, meaning no transmembrane pressure gradient and no permeation; (ii) in cross-flow filtration mode at a pressure of 10 psi (~69 kPa). Operational parameters were continuously monitored and controlled using LabVIEW (i.e. pressure, temperature and the electric potential).

At the end of the experiments the membranes were removed, thoroughly washed with a sterile saline solution, taken for further microscopic visualization and analysis and compared to the controls. All components of the system were aseptically cleaned with a 70% ethanol solution and distilled water. Images were taken from at least 3 random areas on the surface of the membrane and the results presented are representative. In experiments performed in full cross-flow mode with filtration, fouling development was monitored by measuring the normalized permeate flux decrease during the length of the flow experiment. The initial flux was measured just before inoculation (with only feed solution). The normalized flux was defined as the actual flux divided by the initial flux. Unless otherwise stated, experiments were repeated at least 3 times. Microscopic analyses were made at least in three random areas on the surface of the membrane and results presented are representative.
Electrical Set Up and Conditions The experiments were performed either using DC generated by a power supply (GW Instek, GPD-3303s) or AC polarizing electric field, generated by a dual channel arbitrary function generator-AFG (GW Instek, AFG-2225). A square wave pulse at offset named $mV_{pp}$ (millivolt peak to peak) or above (positive pulse)/below (negative pulse) offset was applied for AC. The duty ratio (percentage of pulsing time over one cycle) of the function was set to 50%. A wide range of conditions were investigated in terms of applied AC voltages from 300 to 6,000 mV with frequencies ranging from 10 Hz to 10 kHz. DC was applied in a voltage range of 600 mV to 3,000 mV.

Two electrical circuits were explored in both AC and DC as well. The first was in resistive mode (also named along) using an external resistance in the range of 10 to 200Ω and the second in capacitive mode (also named across) with a feed solution supplemented with 50 mM NaCl to enhance the electrical conductivity between electrodes. Adding an external resistance reduced the voltage drop along the membrane, which behaves as a resistor within the electric circuit in resistive mode. The voltage drop was measured by means of an oscilloscope.

The electrical current (I, mA) applied to the membranes was calculated as a function of the voltage (V, mV) and total resistance (R, Ω), I=V/R, where the total resistance, R, is the sum of the external or medium resistance and membrane resistance. The electrical energy expenditure (E, mW) was calculated as E=V×I×t, where t is the time of the run. As described above FIG. 8 shows a schematic diagram of a typical set up of the EMBS under different electrical circuits.

Example 5

Analytical Techniques

High Resolution-Scanning Electron Microscope (HR-SEM)

HR-SEM was performed in a Carl Zeiss Ultra-Plus FEG-SEM. Samples were fixed with glutaraldehyde 3% (v/v) and dehydrated using a cold ethanol gradient at 4° C. Prior to imaging, samples were sputter coated with carbon.

Confocal Laser Scanning Microscope (CLSM)

CLSM imaging was performed using either a Carl Zeiss CLSM (LSM 510 META) with a ×63 water-dipping objective. In order to visualize dead/live bacterial attachment, the membrane samples were stained with dead/live staining (Invitrogen-Molecular Probes): Syto 9 (S34854) at a concentration of 5 μM and Propidium Iodide (P4170) at a concentration of 30 μM.

Image analysis software, Imaris 7.7.2 (Bitplane) was used to analyze the dead/live stained CLSM images and quantify the amount of biofilm in terms of specific biovolume ($BF_v$, $\mu m^3$ per 100 $\mu m^2$); total biovolume was calculated as the sum of both fields. The theoretical number of bacteria ($TN_b$) within the 3-D structure of the biofilm was calculated estimating the volume of a single bacterium ($V_b$) as 0.20 $\mu m^3$, as follows: $TN_b=BF_v/V_b$ (cell/100 $\mu m^2$). $V_b$ was estimated according to the following equation: $V_b=\pi r^2(4/3r+l-2r)$, based on an average size of an individual cell of *P. putida* of 1.2±0.1 μm length (l) and 0.5 μm radius (r). All z-sections were processed and flattened into a single overlaying layer using Image J (7.7.2win 64). For each analysis the threshold value was adjusted to highlight the biofilm. The size of each image processed was 85 μm×85 μm.

Other Analytical Techniques

The zeta potential of bacterial suspensions was measured in a 10 mM KCl solution (ZetaSizer Nano-ZS Malvern). Total organic carbon of feed solution was measured in a TOC-$V_{CPX}$ analyzer (Shimadzu). Electrically generated hydrogen peroxide (was measured using an Amplex Red Hydrogen Peroxide/Peroxidase Assay Kit (ThermoFisher). Additional detailed protocol is presented in the supplementary information.

X-ray photoelectron spectroscopy (XPS) analysis was performed using a Thermo VG-Scientific—Sigma probe system with a monochromatic Al Kα at 1486.6 eV source and a hemispherical electron energy analyzer.

Example 6

Results

Influence of Electrical Current in Resistive Mode on Biofouling Control

The effect of AC, i.e., polarizing electric field, in resistive mode on the attachment of bacteria on CNT membranes and biofilm formation was first thoroughly studied in flow-through regime in order to find the most effective operational conditions.

The influence of AC frequencies in the range of 10 Hz to 10 kHz at 1800 $mV_{pp}$ (at offset with 50% duty cycle) is presented in FIG. 10. As the frequency increased antibiofouling (and cell inactivation) gradually increased as depicted by the decrease of total (and dead) number of bacterial cell attached, reaching the most significant reduction between 10 to 100 Hz and reaching an almost asymptotic value at 1 kHz.

Only sporadic single cells could be observed on the membranes in all range of frequencies studied in contrast to a relatively dense biofilm (11.4±1.2 μm) observed in the control membranes after 72 h of exposure. As can be further seen from the data presented in FIG. 10, due to the voltage drop (I×R) along the membrane when connecting it in resistive mode and being the solely resistance, a high (phase) and low (ground) potential sides were noticeable. At the lower frequencies (10 and 100 Hz), the bacterial attachment to the ground side of the CNT membrane was somewhat higher than the phase side, however, no differences between the ground and phase sides of the membrane were noticed in the kHz range.

In addition, increasing the frequency above 10 kHz decreased the amplitude of the electric wave and the antibiofouling effect and inactivation rate became less effective. The amplitude at a constant AC potential of an electric circuit, at which the total energy is constant, decreases with the increase of frequency in order to conserve the energy output. Further experiments were, thus, performed at a frequency of 1 kHz.

In order to reduce the voltage drop across the membrane and decrease energy expenditure, the effect of an external resistance connected to the ground side of the electric circuit at constant AC potential of 1800 mVpp at offset and 1 kHz, was then studied in the range from 0 Ω to 200Ω (the intrinsic CNT membrane resistance in the electrical circuit was roughly 0.53±0.12Ω). The results are presented in FIG. 11. The addition of an external resistance not only reduced potential drop along the membrane but also enhanced the prevention of bacterial attachment on the membranes applying the same potential. Indeed, an almost 4-fold decrease of cells attachment (1452.5±240.0 to 345.7±26.8 total cells/100 μm²) was obtained increasing the external resistance from 0 to 200Ω. However, inactivation rate decreased with increasing resistance (41.4±7.3% to 19.1±2.8%, respectively), most obviously due to the decreases of current by increasing resistance. The attachment of cells was dominant in the control with most of them in living state (93.2±5.5%). Further experiments were performed with an external resistance of 100Ω.

To further evaluate the antibiofouling/inactivation capabilities of the AC in resistive mode, a wave pulse shift was tested above (+0.45, positive potential) and below (−0.45, negative potential) offset and compared with offset. A constant AC potential at 1 kHz frequency and 100Ω external resistance was applied, meaning −900 to +900 mV at offset (1800 mV$_{pp}$), 0 to 1800 mV above offset and −1800 to 0 mV below offset (FIG. 12). Shifting the wave pulse above offset reduced bacterial attachment about 2-folds, from 512.4±32.6 at offset to 228.7±017.4 total cells/100 μm$^2$ above offset while increased cell inactivation about 4 times (13.6±4.2 to 56.2±9.6%, respectively). Remarkably, shifting the wave pulse below offset resulted somewhat less effective, yielding 427.1±35.2 attached bacteria per 100 μm$^2$ and 7.3±0.6% inactivation. Again, compared to a relatively dense biofilm layer on the control membranes (thickness of 9.1±1.2 μm), corresponding to total attached cells number of 4972.6±313.1 per 100 μm$^2$ (see FIG. 12), only sporadic single cells were detected under the electrical field. Further experiments were carried out with wave pulse above offset.

Finally, the influence of the AC voltage in resistive mode on antibiofouling/inactivation capabilities on the CNT membranes was studied in the range of 300-1500 mV at the most efficient conditions, namely frequency of 1 kHz, external resistance of 100Ω and wave pulse above the offset (FIG. 13). As clearly seen, increasing the intensity of the electrical field gradually reduced the attachment of bacterial cells practically completely with a concomitant inactivation of attached bacteria, reaching 95.3±2.5 at 1500 mV. This behavior can be related to direct oxidation and/or generation of secondary oxidizing species, such as hydrogen peroxide or active chlorine. Due to the presence of the external resistance connected to the membrane and potential above offset both ends of the membrane displayed similar attachment in all the cases.

For comparison, cathodic DC in resistive mode in the presence of 100Ω external resistance was tested as a means to control fouling on the conducting CNT self-supporting membranes in the voltage range of 600-1500 mV (see Table 8 presenting the effect of cathodic DC voltage on biofilm control in resistive mode with 100Ω external resistance in flow-through regime (growing conditions). Increasing the cathodic potential resulted in an increased antibiofouling effect (~8 fold at 600 mV and −25 fold at 900 mV to about 300 fold at 1500 mV) along with inactivation of attached bacteria (2.4, 22.8 and 29.3%, respectively) relative to the control.

TABLE 8

| Voltage (mV) | Attached bacteria (cell/100 μm$^2$) | | Cell inactivation (%) |
|---|---|---|---|
| | Live | Dead | |
| Control | 4067.9 ± 270.2 | 46.6 ± 2.3 | 1.1 ± 0.0 |
| 600 | 533.2 ± 5.6 | 12.9 ± 0.9 | 2.4 ± 0.1 |
| 900 | 124.5 ± 20.1 | 36.7 ± 7.0 | 23.1 ± 6.0 |
| 1500 | 10.0 ± 1.8 | 4.1 ± 1.0 | 29.4 ± 6.8 |

*Values represent average ± standard deviation of at least 3 replicates of Imaris quantification of biofilm attached on the CNT membranes after 72 h incubation.

Although a similar trend was seen in resistive mode between cathodic DC and AC, it has to be noted that at the same electrical conditions, a higher efficiency was noticed for AC, especially the higher inactivation (compare FIGS. 13A-E and Table 8). Indeed, AC at 300 mV prevented the attachment effectively as DC at 900 mV whereas ~95% of the attached bacteria were inactivated at 1500 mV in AC compared to ~29% in DC. The combination of electrostatic and either direct or indirect oxidation both are favorable in the AC electric field due to the polarizing current. All in all these results emphasize the advantage of the polarizing current both on preventing cell attachment and enhancing inactivation.

Influence of Electrical Current in Capacitive Mode on Biofouling Control:

The influence of polarized AC and DC electric fields through capacitive mode was tested under flow-through conditions using growth medium solution supplemented with 50 mM NaCl.

The effect of AC in capacitive mode is presented in FIGS. 14A-B. The whole cell potential range studied was between 0 to 4500 mV, 50% duty cycle, above offset (positive pulse). In absence of electrical potential, i.e., control, a relatively dense 3-D biofilm was developed on the membrane's surface (10.3±1.3 μm) and most attached bacteria (5536.7±560.1 cell/100 μm$^2$) were in living state (98.3±0.5%). With the increase of the applied electrical potential the number of attached bacteria appeared mostly as sporadic individual cells in monolayer distribution whose number decreased exponentially at an average rate of 0.9% per mV as the relative rate of inactivation did (0.8%/mV).

The increase of dead cells numbers as a result of the increase of the applied potential suggests bacterial inactivation due to oxidation. For example, when applying 1000 mV the bacteria cells were attached in monolayer (470.9±44.1 cell/100 μm$^2$) and most of them were viable (83.5±1.0%). At a potential of 3000 mV, 310.4±50.4 cell/100 μm$^2$ were found attached to the membrane surface however most of them were inactivated (71.2470.7±5.2%) and at 4500 mV only a limited number of bacteria were found attached (39.0±0.6 cell/100 μm$^2$), among which 80.1±5.6% were found inactivated (see FIGS. 14A-B). HRSEM micrographs displayed a similar trend in which a decline in the number of bacteria attached was observed as the applied electrical potential increased (FIGS. 14A-B). Damaged cells could be seen at 4500 mV possibly due to direct oxidation, as indicated above.

For comparative purposes, the effect of DC electrical potential form 900 up to 3000 mV in capacitive mode in either cathodic or anodic configuration, as indicated, was then studied (see Table 9 presenting the effect of DC voltage on biofilm control in capacitive mode in flow-through regime (growing conditions).

TABLE 9

| Voltage (mV) | Attached bacteria (cell/100 μm$^2$) | | Cell inactivation (%) |
|---|---|---|---|
| | Live | Dead | |
| Control | 2491.5 ± 219.6 | 232.7 ± 29.5 | 8.5 ± 0.3 |
| 900 (A) | 1574.5 ± 133.5 | 607.4 ± 28.9 | 27.9 ± 2.6 |
| 900 (C) | 34.8 ± 7.5 | 1.1 ± 1.0 | 3.2 ± 2.9 |
| 1500 (C) | 7.7 ± 1.2 | 0.9 ± 0.5 | 10.5 ± 3.7 |
| 3000 (C) | 3.2 ± 1.5 | 1.3 ± 1.0 | 24.0 ± 11.0 |

*Values represent average±standard deviation of at least 3 replicates of Imaris quantification of biofilm attached on the membranes after 72 h incubation.
(A): anodic current;
(C): cathodic current.

Again, in the absence of applied electrical potential (control) a dense biofilm could be seen at the membrane surface with a thickness of 11.5±1.5 μm. A relatively less dense biofilm could be seen when a relatively low anodic potential of 900 mV was applied with a thickness of 7.4±0.9 μm. In contrast, when cathodic potentials (900-3000 mV) were applied, an almost complete prevention of bacterial attachment was ob served. Quantification of the number of bacteria attached on the membrane surface depicts a significant decline with increasing cathodic potential indicating electrostatic repulsion (see Table 9). At difference of the trend found with AC, only a slight inactivation effect could be observed with DC (few dead cells were inactivated) with increase of the cathodic potential, confirming lack of oxidation of attached cells.

To summarize this part, although both AC and cathodic DC displayed similar antibiofouling activity in capacitive mode the inactivation rate of AC was markedly superior. Even though anodic DC and AC displayed close related inactivation potential, the former was not effective as the attachment was still dominant. The higher potentials needed for both currents in capacitive mode in comparison to resistive, highlight the reliance of the capacitive system on the electrical conductivity of the medium.

Influence of Polarized Electrical Potential on Biofouling Control in Crossflow Filtration Mode To evaluate the influence of AC electric field on the antibiofouling activity of CNT self-supporting membranes in filtration mode, both growing (fed with diluted LB-medium) and non-growing conditions (fed with saline solution) were performed. Polarizing current was applied in resistive mode in the voltage range of 0 to 4500 mV at 1 kHz frequency, 100Ω external resistance and square wave pulse above offset (+0.45). For reference, 1500 mV DC both for anodic and cathodic at capacitive mode were tested.

The results in growing conditions are presented in Table 10 showing the effect of electrical potential on biofilm control in cross-flow regime (growing conditions). A very dense and developed biofilm (mean thickness of approximately 22 μm) was observed in the control membrane, almost two-fold thicker than that observed in the flow-through controls. This disparity may be attributed to the permeate drag force towards the membrane which in conjunction with intensive biofilm-forming conditions applied counter rested the bacterial rejection of the electrical field (see discussion below).

TABLE 10

| Voltage (mV) | Attached bacteria (cell/100 μm²) | | Cell inactivation (%) |
|---|---|---|---|
| | Live | Dead | |
| Control (resistive) | 9624.2 ± 280.9 | 191.4 ± 17.2 | 1.95 ± 0.2 |
| AC-900 | 6726.7 ± 335.6 | 218.2 ± 17.9 | 3.14 ± 0.2 |
| AC-1500 | 3852.6 ± 89.2 | 1892.6 ± 97.6 | 32.94 ± 1.4 |
| AC-3000 | 3054.6 ± 90.6 | 2596.9 ± 181.1 | 45.92 ± 2.4 |
| AC-4500 | 2097.9 ± 85.7 | 2318.1 ± 107.3 | 52.49 ± 0.4 |
| Control (Capacitive) | 9122.7 ± 214.6 | 152.7 ± 22.1 | 1.65 ± 0.3 |
| DC-1500 (C) | 5594.0 ± 268.6 | 379.4 ± 42.5 | 6.36 ± 0.7 |
| DC-1500 (A) | 7459.3 ± 1005.8 | 1950.1 ± 120.1 | 20.85 ± 2.1 |

*Values represent average ± standard deviation of at least 3 replicates of Imaris quantification of biofilm attached on the membranes after 72 h incubation. AC was applied in resistive mode with 100 Ω external resistance at 1 kHz frequency, square wave above offset (+0.45) in different voltage.
(C) DC capacitive cathodic mode,
(A) DC capacitive, anodic mode.

Although in the presence of the electrical field a reduced biofouling layer was observed, which decreased with the increase of the electrical potential, still a defined biofilm rather than sporadic deposition of single cells was observed which was also depicted by negligible effect on the permeation rate of the membrane compared to the control. Nevertheless, inactivation of attached cells increased as function of the electrical potential applied for AC and anodic DC (see Table 10). Again, AC potential resulted somewhat more effective than anodic or cathodic DC potentials.

In order to analyze more in detail the effect of the permeate drag force in presence of the electrical field, a set of cross-flow filtration experiments of 12 h duration was performed in non-growing conditions with sterile saline after inoculation with $10^7$ CFU/mL $P.$ $putida$. As expected, no significant inactivation of bacteria was observed in the control with no current applied (96.5±2.7% remained viable) whereas as the electrical potential increased both the total number of bacteria attached and residual viable bacteria decreased gradually (see Table 11 showing the effect of AC voltage on biofilm control in resistive mode with 100Ω external resistance in cross-flow regime (non-growing conditions)). Almost no observed impact on cell viability (94.8±4.2) was seen when applying an AC potential of 1000 mV and lower, which correspond to a value below hydrolysis potential of water.

TABLE 11

| Voltage (mV) | Attached bacteria (cell/100 μm²) | | Residual viable bacteria (%) |
|---|---|---|---|
| | Live | Dead | |
| Control | 432.0 ± 15.9 | 16.4 ± 13.2 | 96.5 ± 2.7 |
| 1000 | 410.7 ± 39.5 | 21.9 ± 17.5 | 94.8 ± 4.2 |
| 3000 | 80.8 ± 19.6 | 128.5 ± 8.7 | 38.3 ± 6.2 |
| 4500 | 24.3 ± 3.4 | 99.2 ± 25.6 | 20.2 ± 4.7 |
| 6000 | 4.8 ± 2.0 | 21.8 ± 7.0 | 18.2 ± 7.0 |

*Values represent average ± standard deviation of at least 3 replicates of Imaris quantification of biofilm attached on the membranes after 12 h filtration. AC was applied in resistive mode with 100 Ω external resistance at 1 kHz frequency, square wave above offset (+0.45).

These results suggest that inactivation resulted in a bactericidal effect that can be attributed to either direct oxidation or formation of hydrogen peroxide as well as to other oxidizing species. In in vitro tests performed in pure solution in 5 cm³ spectrophotometer cuvettes, hydrogen peroxide formation rate at electrical conditions similar to those applied in the filtration experiments increased linearly with $lnV_{AC}$ with a slope of 3.2 μM (FIG. 15), which depicts a low $H_2O_2$ accumulation potential. Hence, although possibilities for indirect oxidation for inactivation cannot be ruled out, $H_2O_2$ may not be a decisive factor. The permeability data of the cross-flow filtration under non-growing condition is presented in FIG. 16. The normalized permeability data of the membranes under the electrical field was in good correlation with the microscopic analyses of the surface of the membrane. Indeed, while the normalized permeation rate of the control was reduced by approx. 60% after 12 h of run, the intensification of the electric potential applied along the membranes gradually hindered permeate reduction achieving only 17% reduction at 6000 mV.

FIG. 17 presents a table summarizing a Comparison of biofouling control between literature and present disclosure.

Theoretical Estimation of Electrostatic and Drag Forces on Bacterial Attachment:

Without being bound by any particular mechanism, in order to describe the deposition of bacterial cells on the membrane surface in the presence of the electrical field, DLVO interactions were considered in combination with bulk and interfacial hydrodynamic interactions. The sum of the bulk and interfacial forces at a given separation distance provides an estimate of the attractive or repulsive force a bacterium might experience. The following forces were taken into consideration: attractive van der Waals ($F_{vdW}$), modified electrostatic double layer ($F_{ES}$), cross-flow lift ($F_L$)

and permeation drag ($F_D$). The net interfacial force ($F_T$), i.e., the net force between the charged membrane and bacteria, was determined from the following equation:

$$F_T = F_D + F_L + F_{ES} + F_{vdW}$$

Due to calculation constraints only DC field could be numerically resolved. As flow velocity was kept constant and relatively low (1.85 cm/s, low Reynolds numbers 416) the calculated shear rate (74.4 l/s) and lift forces ($2.12 \times 10^{-5}$ nN) were negligible in comparison to the attractive permeate drag force (0.0918 nN at a filtration pressure of approx. 10 psi).

In flow-through mode, i.e., in the absence of permeate drag force, as the cathodic potential applied on the membrane was increased (from 0.5-3.0V) the calculated primary maximum's distance increased accordingly. In all cases, the overall repulsive forces were in the range of 0.85-1 nN, able to prevent, theoretically, attachment of bacteria or particle to the surface. At this distance, attractive vdW forces are negligible in comparison to the electrostatic repulsive forces (~10-3 nN). At lower distances from the membrane, attractive van der Waals interactions become more dominant, depending on the applied potential and eventually leading to adhesion between the bacteria and the charged membrane. These results are in agreement with the low experimental concentrations of bacteria adhered to the membrane surface when a 3V DC cathodic potential was applied (~7%). Electrochemical reactions at cathodic DC potentials >1.23V which may enhance bacterial detachment were not considered in the theoretical force calculations.

In cross-flow filtration mode, permeate flux adds a dominant drag force leading to the decrease of the net interfacial force, approaching null and negative values at distances of 2.5-5.4 nm according to the applied potential. The permeate drag force not only changes the distance of the primary maximum but also decreases the overall repulsive force value. Indeed, the influence of the directing drag force imposed by the permeate flux in cross-flow mode compared to transport of cell towards the surface by random flow pattern in flow-through mode can be drawn from the experimental bacterial attachment data of the control membranes, i.e., 0V ($9275.4 \pm 236.7$ and $2724.2 \pm 249$ cell/100 $\mu m^2$, respectively).

Further experimental data depicted bacterial attachment to the membranes surface even when a cathodic potential of 1.5V was applied ($5973.4 \pm 311.1$ cell/100 $\mu m^2$), although bacterial concentration decreased with the increasing of applied potential as expected (Table 10, bottom lines). The difference between the experimental and theoretical results of repulsive forces may due to the estimation of the permeate force, where the hydrodynamic correction factor may change the permeate drag force significantly. In addition, all calculation refers to inert particles, i.e., bacteria with no motility abilities, while 'real' bacteria can react with the surrounding environment (e.g., motility, pili) and 'swim' towards the membrane surface.

Comparing both AC and DC, AC was found more effective both in terms of biofouling reduction compared to cathodic DC and in terms of cell inactivation compared to anodic DC, either in resistive or capacitive modes. Hence, the electrostatic repulsion combined with direct oxidation (electron transfer) seems the dominant mechanism in polarizing current, involving the advantages of anodic oxidation and cathodic electrostatic repulsion. Both AC and DC cathodic electric fields, either in resistive or capacitive modes, suppressed bacterial attachment to higher extent than previous studies. However, an exact comparison is not possible because of the different experimental set-ups and conditions.

The influence of electric currents on prevention of bacterial attachment can be summarized as follows: in capacitive mode AC ≥DC cathodic >>DC anodic and in resistive mode AC >DC cathodic >>DC anodic. Polarization of membrane with electric field imposed a strong negative charge to the CNT membrane in AC and cathodic DC, which resulted in a repulsive electrostatic interaction with negatively charged bacteria cells.

The thicknesses of the double layer and, in consequence, the influence of the electrostatic repulsion on the bacterial attachment are dependent on the ionic strength. When increasing the ionic strength, interaction energy between negatively polarized CNT and bacteria are repulsive at shorter distance and become attractive at distances larger than 5 nm. The shielding of electrostatic repulsion can slightly increase bacterial attachment at lower potential. These observations may suggest a higher dependency of capacitive circuits in preventing bacterial attachment on the ionic strength of the medium treated, as well as distance between poles, i.e., feed channel, compared to resistive circuits with external resistance.

Regarding inactivation the mechanism is more complex when comparing AC and DC. Efficient prevention of bacterial attachment and inactivation were found at increasing frequencies with an optimum 1 kHz-10 kHz. Moreover, a slight increase of inactivation was observed when amplitude shifted above offset. Furthermore, $H_2O_2$ generation was very low under AC polarized electric field (6.37 µM at 6000 mV). Thus, also indirect oxidation cannot be ruled out, inactivation might be due to direct electron transfer, disrupting the integrity of the bacteria membrane which leads to decrease in viability.

The net reduced extent of prevention of bacterial attachment and inactivation found in filtration mode is mainly attributed to the permeate drag force.

Electrochemical Impedance Spectroscopy Analysis

Bode plots and complex plane impedance plots of EIS data generated under different solution concentrations and different applied constant voltages are presented in FIGS. 18A-L and 19A-F for resistance and capacitance modes, respectively.

When no supplemental electrolyte was added to the diluted LB medium (0 mM NaCl), a distinct behavior of a pure inductance with only an imaginary impedance component was evident at higher frequencies (100 kHz<f<1 kHz) and a pure resistance behavior was observed at the lower frequency range (<1 kHz). At a frequency of 1 kHz the CNT membrane was AC-frequency independent and purely behaved as a resistor with a zero-imaginary impedance. At frequencies >1 kHz and even higher upon increase in NaCl concentrations, a current-voltage phase separation occurred in the positive region indicating an inductive behavior.

When medium was supplemented with electrolyte (50 and 150 mM NaCl), a new intermediate frequency range was evident (1 kHz>f>10 kHz) with a decrease of VD, indicating that the total impedance of the fabric not only originated from the resistive reactance, but also from a capacitive (when phase angle was negative) or an inductive reactance (when phase angle was positive), or both. The existence of a capacitance behavior around 1 kHz, observed mainly at high salt concentrations, was followed by a dramatic increase in absolute impedance of the system at frequencies >10 kHz due to inductance reactance, as manifested in positive phase shift values, alongside negative imaginary impedance components. The capacitive mode configuration is discussed in FIGS. 19A-F).

To test whether CNT degradation takes places upon oxidation in resistive mode, XPS analysis was carried out. The composition, C1s high resolution spectra and deconvolution lines denote minor changes before and after run, implying minor deterioration of the CNT structure.

In order to assess Ohmic effect and its possible implication on membrane oxidation, temperature development on the membranes connected in resistive mode was measured (FIGS. 20A-E showing the heat generation measured by infrared thermometer during electric field application).

TABLE 12

| Voltage applied (V) | Temperature (° C.) | | | |
|---|---|---|---|---|
| | with 100 Ω resistor | | without resistor | |
| | AC | DC | AC | DC |
| 0.9 | 24 | 26 | 24 | 27 |
| 1.5 | 25 | 26 | 25 | 38 |
| 3.0 | 25 | 26 | 31 | 48 |
| 4.5 | 26 | 26 | 41 | 52 |
| 6.0 | 27 | 27 | 50 | 65 |

No measurable temperature change as function of voltage was found was found on the membranes surface in either AC or DC with external resistor, depicting negligible heat generation (heat dissipation most probably took place at the external resistor). Moreover, minor changes in conductivity of membrane subjected to electric field for 72 h was noticed compared with the control membranes, regardless of the voltage applied (FIG. 21).

Taken together, the contribution of low voltage electric potential (negative, positive, alternating) under flow conditions with respect to prevention of attachment, detachment and inactivation bacteria in growing conditions on charged CNT membranes was demonstrated.

Self-supporting, highly conductive CNT membranes, appear as an effective tool to prevent initial bacterial attachment in growing and non-growing condition by low electrical potential. The energy consumption of the conductive CNT membranes is very low; for example applying 3000 mV per square meter of membranes will consume $27 \times 10^{-3}$ kWh/m$^2$ in resistive mode with 100Ω external resistance. Both electrostatic and bactericidal effects seem to be involved in preventing initial attachment and inactivation as well.

In terms of prevention of attachment and inactivation, similar trends were observed under cross-flow filtration as in flow-through mode. The population of bacteria in real pre-treated feedwater will be at least two orders of magnitude lower of that tested here and crossflow velocity about one order of magnitude higher enhancing repulsive lift and shear rate forces.

Thus, biofouling control by AC is expected to be feasible adapting the electric field to the bacterial population and nutrients present in the feedwater. AC polarizing electric field is better than the DC electric field since it has both prevention of attachment and inactivation as well. Electric circuit through resistive mode also prevents the initial bacterial attachment and inactivates the live cells remained on the surface. Although the strength of the electrical field needs to be optimized to counteract the permeate drag forces, electrically polarized CNT membranes offer a viable antibiofouling strategy that has the potential to significantly hinder biofouling and facilitate membrane care during filtration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A carbon nanotubes (CNT) membrane, wherein said CNT membrane comprises at least one porous laminate of CNT fibers, the porous laminate comprises a plurality of CNT layers, wherein said CNT membrane is characterized by: electrical conductivity of at least $10^3$ S/m, water permeability coefficient ($L_p$) in the range of 200 to 700 lmh/bar, and a density of from 0.1 gr/cm$^3$ to 0.8 gr/cm$^3$;
   wherein said porous laminate is characterized by one or more from:
   (a) comprising pores having a median size of 15 nm to 150 nm;
   (b) tortuosity factor of at least 1.7;
   (c) a length to thickness ratio of 800 to 1200;
   (d) a tensile strength of at least 0.10 GPa and wherein said CNT membrane is in a form of a self-supporting membrane being substantially devoid of a supporting substrate or of a polymer.

2. The CNT membrane of claim 1, characterized by at least two from (a) to (c).

3. The CNT membrane of claim 1, wherein said at least one porous laminate is characterized by a thickness of 20 to 100 μm.

4. The CNT membrane of claim 1, wherein said at least one porous laminate is characterized by a root-mean-square (RMS) surface roughness of at least 20 nm.

5. The CNT membrane of claim 1, wherein said at least one porous laminate is characterized by a static water contact angle of at least 70°.

6. The CNT membrane of claim 1, wherein said at least one porous laminate is characterized by thermal stability of up to at least 400° C.

7. The CNT membrane of claim 1, wherein said porous laminate has attached on at least one surface thereof one or more chemical functional groups.

8. A method of inhibiting, reducing and/or retarding a biofilm formation on a surface of the CNT membrane of claim 1, the method comprising applying electrical current to at least portion of the CNT membrane.

9. The method of claim 8, being affected under electric potential implemented on the CNT membrane of at least 1000 mV, optionally, wherein said electrical current is an alternating current (AC), optionally wherein said AC has a frequency in the range of 1 Hz to 10 kHz.

10. The method of claim 8, wherein said electrical current is a direct current (DC).

11. The CNT membrane of claim 1, wherein said porous laminate is characterized by an absolute pore size rating of below 100 nm, or of below 40 nm.

\* \* \* \* \*